United States Patent [19]
Pittet et al.

[11] Patent Number: 4,727,197
[45] Date of Patent: Feb. 23, 1988

[54] PROCESS FOR PREPARING NATURAL BENZALDEHYDE AND ACETALDEHYDE NATURAL BENZALDEHYDE AND ACETALDEHYDE COMPOSITIONS, PRODUCTS PRODUCED THEREBY AND ORGANOLEPTIC UTILITIES THEREFOR

[75] Inventors: Alan O. Pittet, Atlantic Highlands; Ranya Muralidhara, Fair Haven; Arthur L. Liberman, Highlands, all of N.J.

[73] Assignee: International Flavors & Fragrances Inc., New York, N.Y.

[21] Appl. No.: 11,828

[22] Filed: Feb. 6, 1987

Related U.S. Application Data

[60] Division of Ser. No. 896,174, Aug. 13, 1986, Pat. No. 4,683,342, which is a continuation-in-part of Ser. No. 780,298, Sep. 26, 1985, Pat. No. 4,617,419.

[51] Int. Cl.[4] .............................................. C07C 45/51
[52] U.S. Cl. ..................... 568/433; 568/458; 568/464
[58] Field of Search .................. 568/433, 458, 464

[56] References Cited
U.S. PATENT DOCUMENTS
4,673,766 6/1987 Buck et al. ..................... 568/433

OTHER PUBLICATIONS
Reeves et al, "TAPPI", vol. 48 (Feb. 1985) No. 2, p. 121.
Bedoukian, "Perfumery and Flavoring Synthesis" 2nd.rev.ed., Elsevier Pub. Co. pp. 91, 92 and 97.

*Primary Examiner*—Werren B. Lone
*Attorney, Agent, or Firm*—Arthur L. Liberman

[57] ABSTRACT

Described is a process for preparing natural benzaldehyde and acetaldehyde and compositions of matter containing natural benzaldehyde and acetaldehyde as well as products produced thereby and organoleptic utilities thereof, which process comprises the step of contacting with base naturally occurring cinnamaldehyde or a natural product rich in cinnamaldehyde such as Ceylon oil of cinnamon, Ceylon cinnamon bark, Saigon cinnamon bark, cassia oil, Ceylon cinnamon quills, cinnamon leaf oil, oil of cinnamon Madagascar or the like according to the reaction:

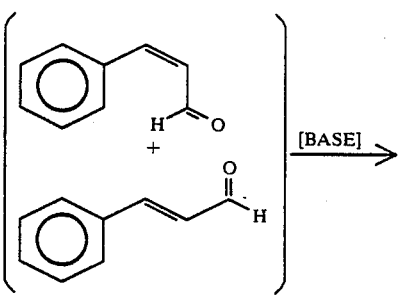

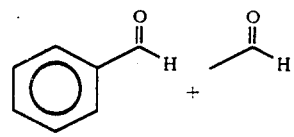

the reaction taking place in aqueous media and in the presence of a food grade or natural nonionic emulsifier, preferably a nonionic sorbitan derivative emulsifying agent and in the absence of any other reagents.

4 Claims, 30 Drawing Figures

GC-IR SPECTRUM FOR EXAMPLE I.

GC-IR SPECTRUM FOR EXAMPLE II.

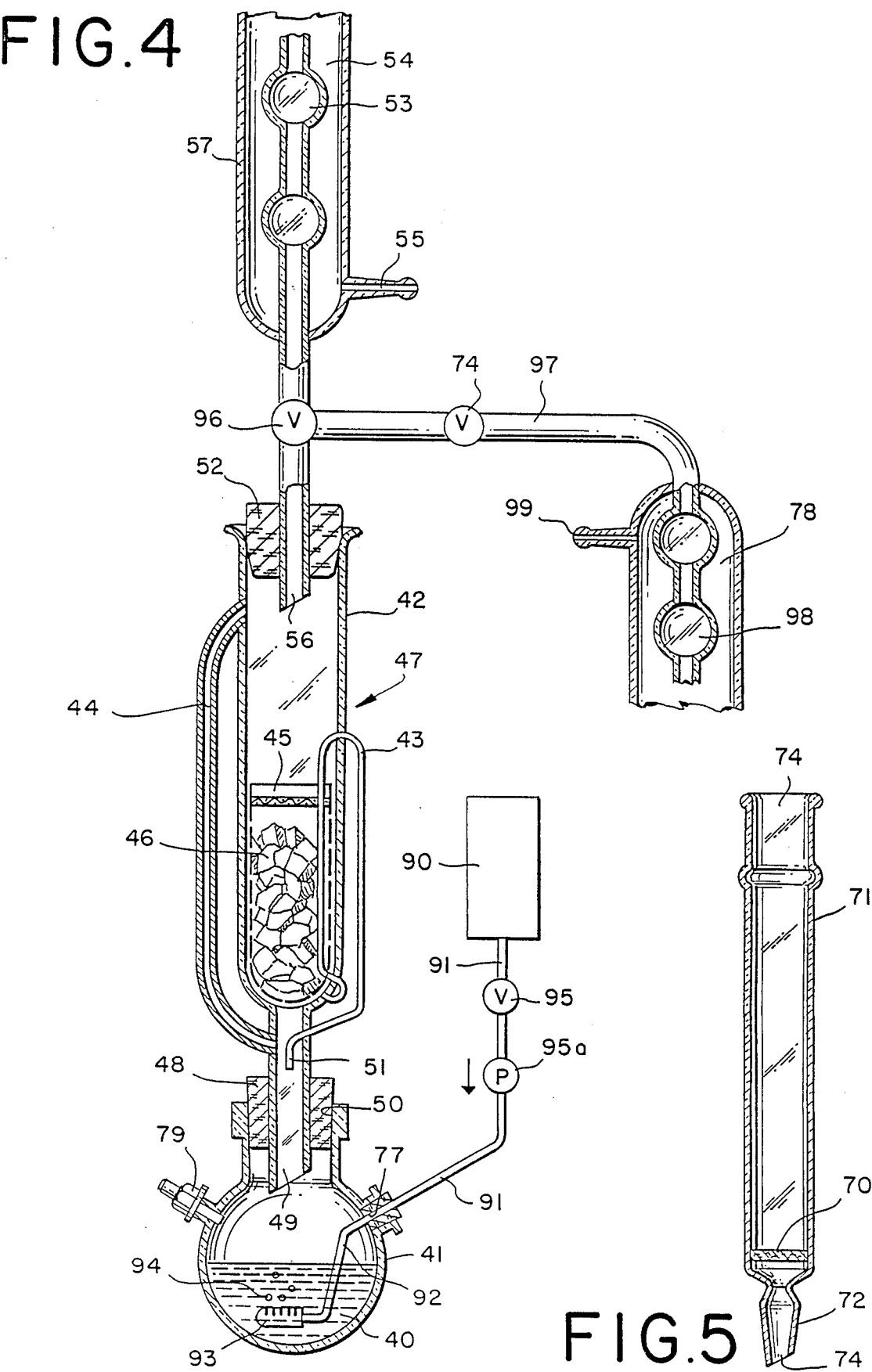

GLC PROFILE FOR EXAMPLE VI

GLC PROFILE FOR EXAMPLE VI.

GLC PROFILE FOR EXAMPLE VI.

GLC PROFILE FOR EXAMPLE VI.

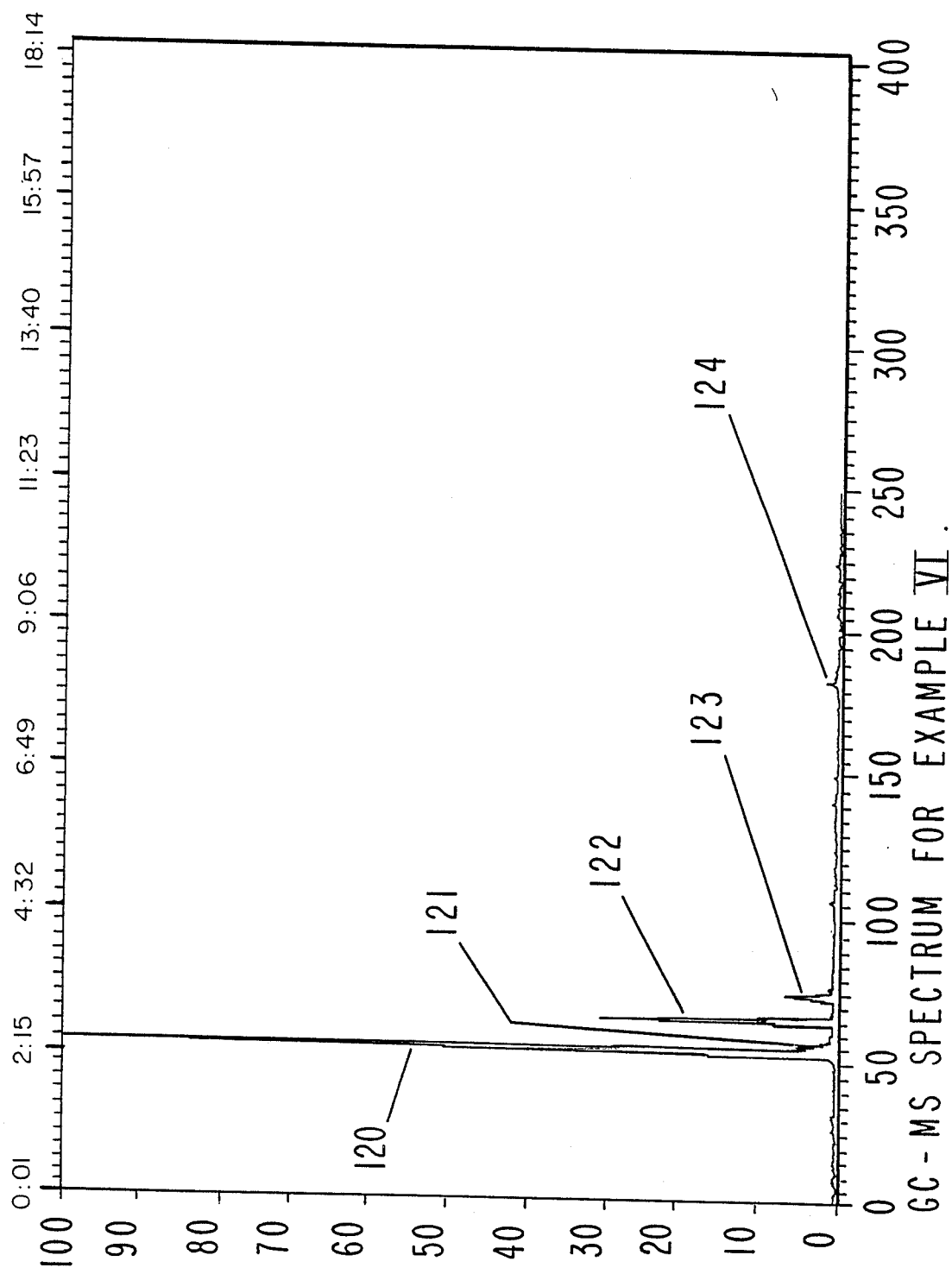
FIG. 12 GC-MS SPECTRUM FOR EXAMPLE VI.

FIG. 15 — GLC PROFILE FOR EXAMPLE XXIV.

GLC PROFILE FOR EXAMPLE XXIV.
(REDISTILLATION FRACTION 54)

FIG. 18 GLC PROFILE FOR EXAMPLE XXIV (REDISTILLATION FOR FRACTION 58).

GLC PROFILE FOR EXAMPLE XXIV
CASSIA OIL

GLC PROFILE FOR EXAMPLE XXIV
STEAM-DISTILLED CASSIA OIL

GLC PROFILE FOR EXAMPLE XXV CRUDE

GLC PROFILE FOR FRACTION I OF EXAMPLE XXV VACCUM DISTILLATION

GLC PROFILE FOR FRACTION 9 OF EXAMPLE XXV
VACUUM DISTILLATION

GLC PROFILE FOR EXAMPLE XXVI
(METHYL SILICONE COLUMN)

GLC PROFILE FOR EXAMPLE XXVI, CRUDE (CARBOWAX 20M COLUMN).

GLC PROFILE FOR EXAMPLE XXXVIII CRUDE

GLC PROFILE FOR EXAMPLE XXXIX
CRUDE

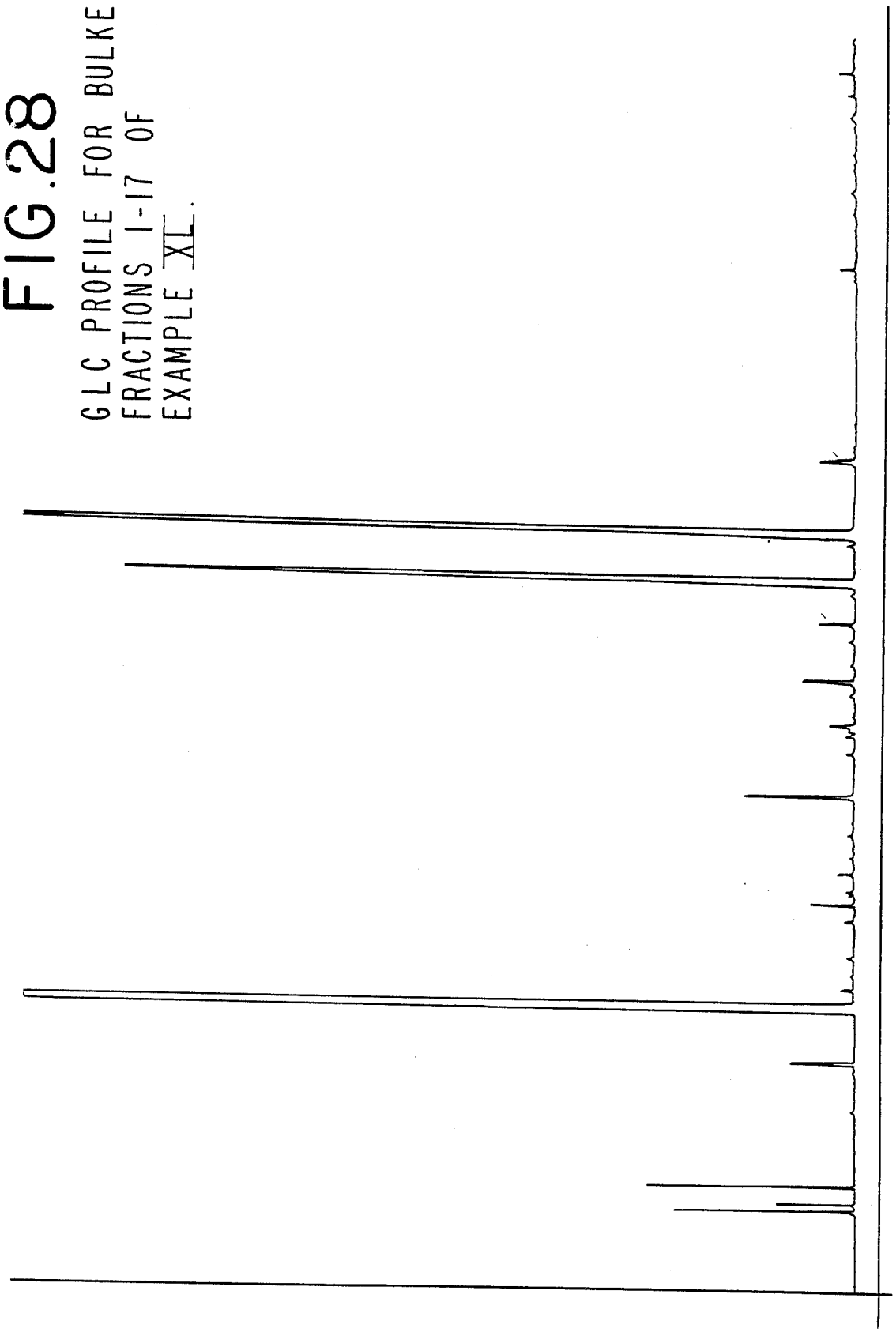
FIG. 28 GLC PROFILE FOR BULKED FRACTIONS 1-17 OF EXAMPLE XL.

PROCESS FOR PREPARING NATURAL BENZALDEHYDE AND ACETALDEHYDE NATURAL BENZALDEHYDE AND ACETALDEHYDE COMPOSITIONS, PRODUCTS PRODUCED THEREBY AND ORGANOLEPTIC UTILITIES THEREFOR

This is a divisional of application Ser. No. 896,174, filed 8/13/86, U.S. Pat. No. 4,683,342, which, in turn, is a continuation-in-part of application for U.S. Pat. No. 780,298 filed on 9/26/85, now U.S. Pat. No. 4,617,419 issued on Oct. 14, 1986.

BACKGROUND OF THE INVENTION

A major use of natural benzaldehyde is an ingredient in "natural" cherry flavor and other flavors for augmenting or enhancing the aroma or taste of consumable materials including foodstuffs, chewing gums, medicinal products, toothpastes, chewing tobacco, smoking tobacco and smoking tobacco articles.

A major use of natural acetaldehyde is as an ingredient in "natural" orange flavor and other flavors for augmenting or enhancing the aroma or taste of consumable materials including foodstuffs, chewing gums, medicinal products, toothpastes and chewing tobacco.

Natural benzaldehyde has been used in natural cherry flavors in the form of apricot kernel derivative as is taught in U.S. Pat. No. 1,416,128 issued on May 16, 1922. An undesirable feature of the known processes for preparing natural benzaldehyde from apricot kernels or reground press cake is that along with the benzaldehyde, toxic hydrocyanic acid is produced which must be separated completely from the benzaldehyde and from the rest of the oil prior to use. Other techniques for producing natural benzaldehyde are known but these techniques produce it in such yields as to cause the resulting process to be uneconomical. For example, Hockenhull, et al, Biochem. J., 50, 605–9, (1952) (Title: "Oxidation of Phenylacetic Acid by *Penicillium chrysogenum*" discloses production of benzaldehyde starting with phenylacetic acid through either benzyl alcohol or mandelic acid via the sequences:

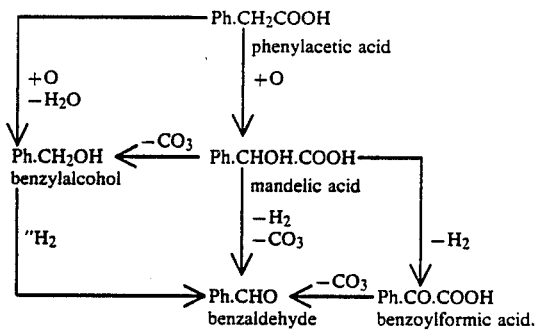

Towers, et al, Can. J. Zool. 1972, 50(7), 1047–50 ("Defensive secretion:biosynthesis of hydrogen cyanide and benzaldehyde from phenylalanine by a millipede") discloses a biosynthetic pathway for the production of benzaldehyde from dietary phenylalanine in *Oxidus gracilis*, thusly:

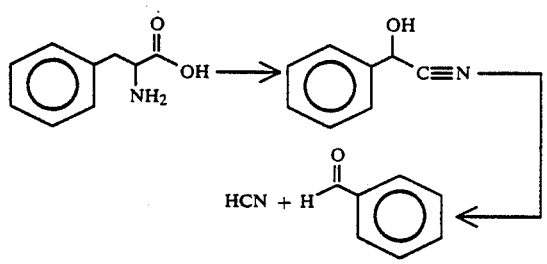

Halpin, et al, Biochemistry, 1981, Volume 20, pages 1525–1533 (Title: "Carbon-13 Nuclear Magnetic Resonance Studies of Mandelate Metabolism in Whole Bacterial Cells and in Isolated, in Vivo Cross-Linked Enzyme Complexes") discloses the biochemical pathway from mandelate ion to benzaldehyde thusly:

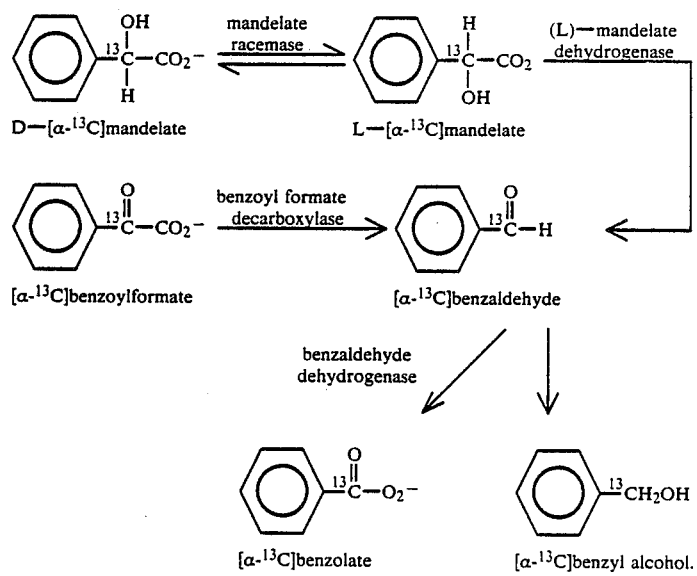

Reeves, et al, TAPPI 48(2), pages 121–5, (1965) (Title: "Reaction Products Formed Upon the Alkaline Peroxide Oxidation of Lignin-Related Model Compounds") discloses the effect of alkaline hydrogen peroxide oxidation on cinnamaldehyde whereby the cinnamaldehyde is split at the double bond with the formation of the corresponding benzaldehyde and benzoic acid according to the reaction:

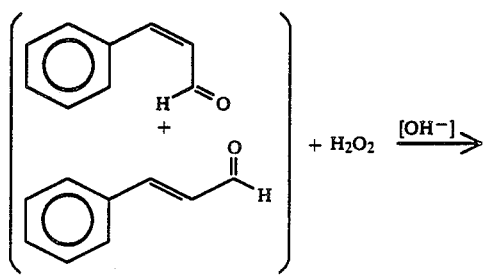

At page 124, column 1, paragraph 1, Reeves, et al theorizes that a "reverse aldol reaction" is not responsible for the formation of veratraldehyde due to the fact that acetaldehyde the other product of the potential "reverse aldol reaction" was not obtained. Therefore, our discovery of the "retro-aldol" reaction taking place, to wit:

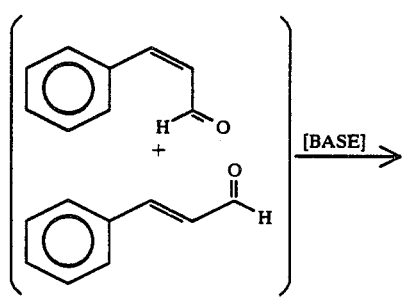
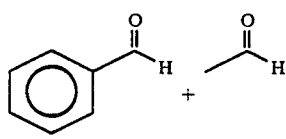

was unexpected and unobvious. The "retro-aldol" reaction, to wit:

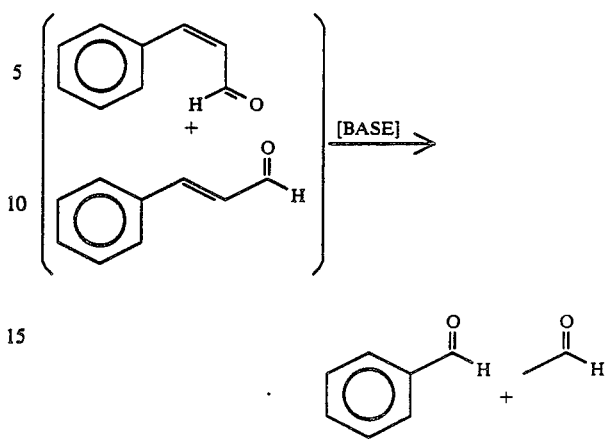

Indeed, took place due to the different reaction conditions from those proposed and set forth in Reeves, et al; different insofar as temperature of reaction and time of reaction are concerned; longer times of reaction and higher temperatures of reaction being the conditions in our "retro-aldol" reaction as opposed to shorter times of reaction and lower temperatures insofar as the Reeves, et al reaction is concerned.

In our own invention, no reagents other than naturally occurring cinnamaldehyde, base, water and non-ionic emulsifier are utilized to carry out the "retro-aldol" reaction of our invention, to wit:

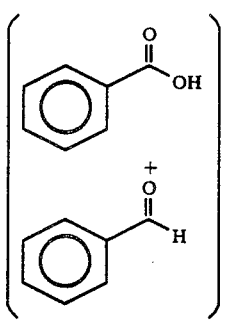
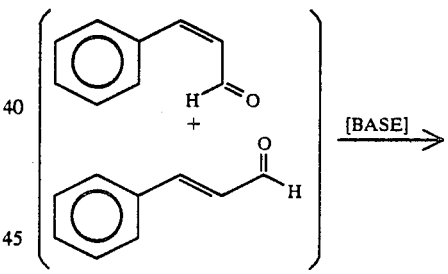

The process of our invention thus gives rise to unobvious, unexpected and advantageous results and represents an advance in the art in the production of "natural" benzaldehyde taken alone or in combination with "natural" cinnamaldehyde; and, further, in the production of "natural" acetaldehyde.

SUMMARY OF THE INVENTION

Our invention is directed to the production of "natural" benzaldehyde and/or "natural" acetaldehyde taken alone or in admixture with "natural" cinnamaldehyde according to a reaction where "natural" cinnamaldehyde is subject to a "retro-aldol" reaction, thusly:

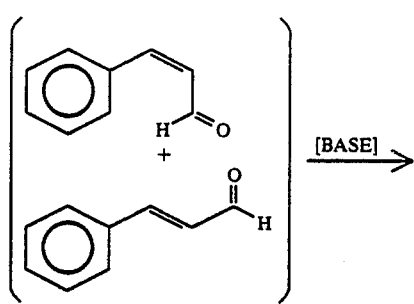 [BASE] →

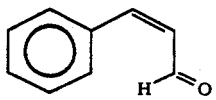

The cinnamaldehyde reaction may occur in either the "cis" form having the structure:

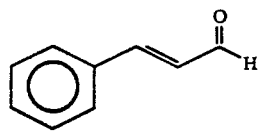

and/or the "trans" form having the structure:

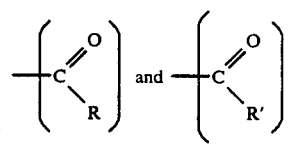

The cinnamaldehyde may be in recovered form from natural sources as by distillation or extraction or the cinnamaldehyde may exist in its natural state immediately prior to the reaction, thusly:
  (I) Oil of Cinnamon Ceylon;
  (II) Ceylon Cinnamon Bark (*Cinnamomum zeylanicum* Nees ex Blume (fam.Lauraceae));
  (III) The Bark of Saigon Cinnamon (*Cinnamomum loureirii* Nees (fam.Lauraceae));
  (IV) The Bark of Cassia cinnamon (ex *Cinnamomum cassia* (Nees)) Nees ex Blume (fam. Lauraceae);
  (V) The Bark of Saigon cinnamon;
  (VI) Oil of Cinnamon Bark Ceylon;
  (VII) "Quills" from Ceylon cinnamon (including "fines", "Barcelona" and "Hamburg");
  (VIII) Ceylon cinnamon quillings and featherings;
  (IX) Ceylon cinnamon chips;
  (X) Ceylon cinnamon bark oil;
  (XI) Oil of cinnamon Seychelles;
  (XII) Oil of cinnamon Madagascar;
  (XIII) Leaves of Cassia;
  (XIV) Cassia Bark (*Cassia lignea* in ground or powdered form);
  (XV) Oil of Cassia.

Thus, the cinnamaldehyde source may be treated with a base such as sodium bicarbonate, potassium bicarbonate, sodium carbonate, potassium carbonate, lithium carbonate, lithium bicarbonate, magnesium hydroxide, calcium hydroxide, calcium carbonate, proline having the structure:

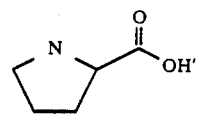

choline having the structure:

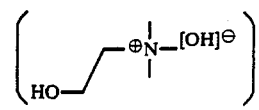

or a natural choline source such as natural lecithin having the structure:

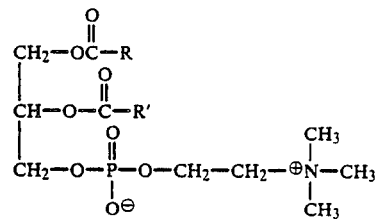

in the presence of base (wherein the residues:

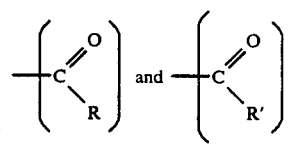

represent palimitoyl, stearoyl, oleyl, linoleyl, linolenyl and $C_{20}$–$C_{22}$ acid residues) [examples of naturally occurring lecithin are soybean lecithin (reference: "Soybeans, Volume II, (Interscience Publishing Company, New York 1951), pages 593–647 and natural phosphatide lecithin] whereby a "retro-aldol" reaction takes place, thusly:

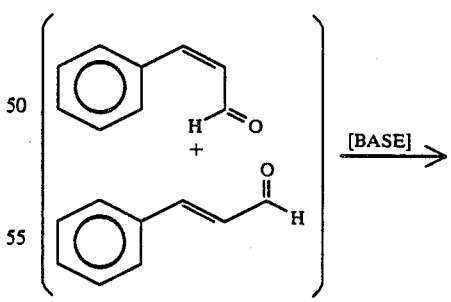
[BASE] →

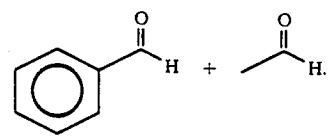

The reaction takes place in the presence of water and a food grade or natural nonionic emulsifier, preferably a nonionic sorbitan derivative emulsifier having one of the structures:

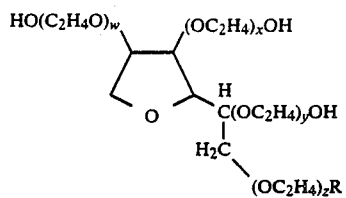

and/or a material or mixture of materials having the structure (s):

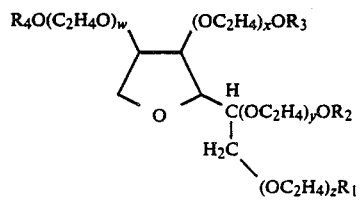

and/or a mixture of materials having the structures:

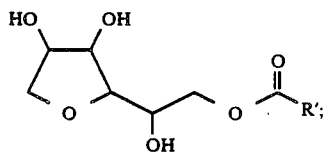

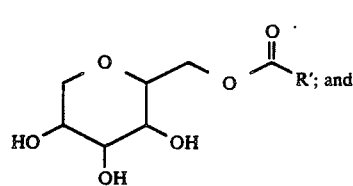

and/or a mixture of materials having the structures:

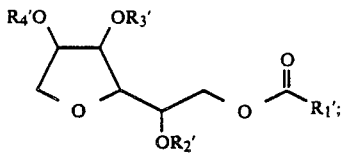

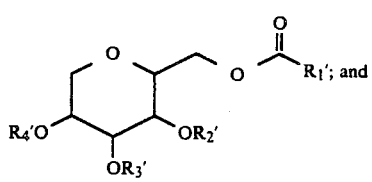

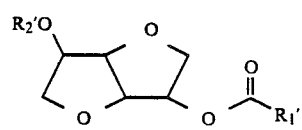

wherein R and R' represent a fatty acid moiety selected from the group consisting of laurate, palmitate, stearate, oleate or tallate; wherein one, two, three or four of $R_1$, $R_2$, $R_3$ and $R_4$ represents the same or different laurate, palmitate, stearate, oleate or tallate and the other of $R_1$, $R_2$, $R_3$ and $R_4$ represents hydrogen; wherein one, two, three or four of $R_1'$, $R_2'$, $R_3'$ and $R_4'$ represents laurate, palmitate, stearate, oleate or tallate and the other of $R_1'$, $R_2'$, $R_3'$ and $R_4'$ represents hydrogen and wherein $W+X+Y+Z$ is in the range of from 4 up to 80 exemplified by the commercial substances identified as TWEEN 20, TWEEN 40, TWEEN 60, TWEEN 80, SPAN 20, SPAN 40, SPAN 60, SPAN 80, T-MAZ 65K ® and T-MAZ 60K ® (T-MAZ being a registered trademark of Mazer Chemicals Inc., 3938 Porett Drive, Gurnee, Ill. 60031) which are defined as follows:

(i) TWEEN 20 has the structure:

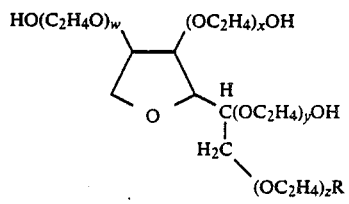

wherein $W+X+Y+Z=20$ and wherein R represents 55% monolaurate and the balance of the R moiety is myristate, palmitate and stearate;

(ii) TWEEN 80 has the structure:

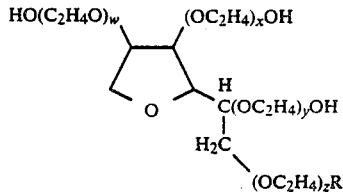

wherein $W+X+Y+Z=20$ and wherein the R moiety is 75% monooleate and the balance is linoleate, palmitate and stearate;

(iii) TWEEN 40 has the structure:

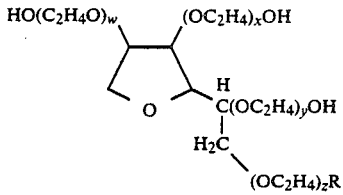

with $W+X+Y+Z=20$ and wherein R represents 90% monopalmitate and 10% stearate;

(iv) TWEEN 60 has the structure:

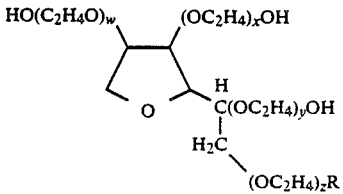

wherein $W+X+Y+Z$ is 20 and the R moiety is 55% monostearate and 45% palmitate;

(v) SPAN 20 is a mixture of the compounds having the structures:

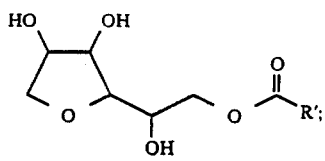

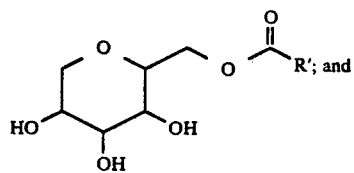

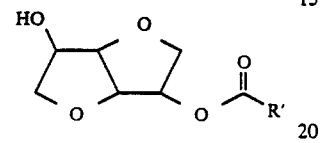

wherein the R' moiety represents laurate;
(vi) SPAN 80 is a mixture of the compounds having the structures:

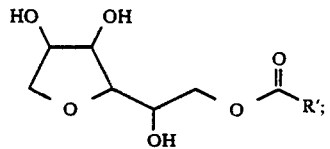

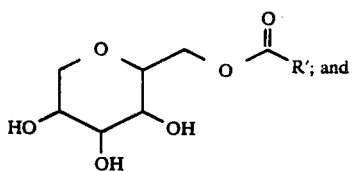

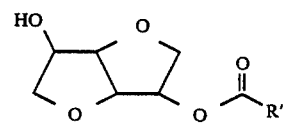

wherein the R' moiety is the monooleate residue;
(vii) SPAN 40 is a mixture of the compounds having the structures:

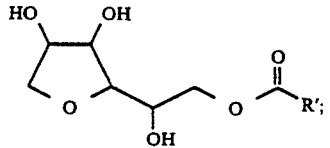

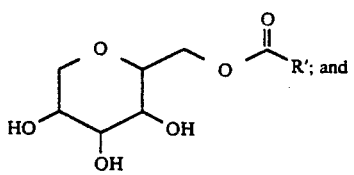

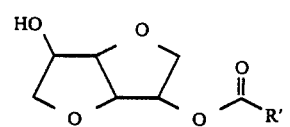

wherein the R' moiety is the monopalmitate residue;

(viii) SPAN 60 is a mixture of the compounds having the structures:

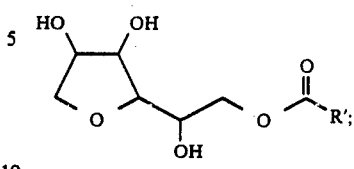

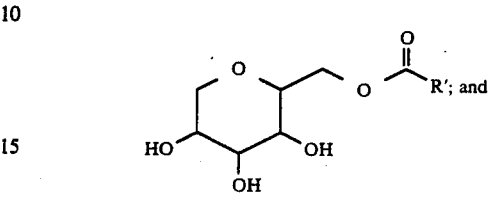

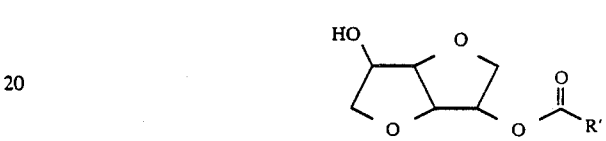

wherein the R' moiety represents the monostearate residue; T-MAZ 65K ® (registered trademark of Mazer Chemicals, Inc. of Gurnee, Ill.) is a mixture of compounds defined according to the structure:

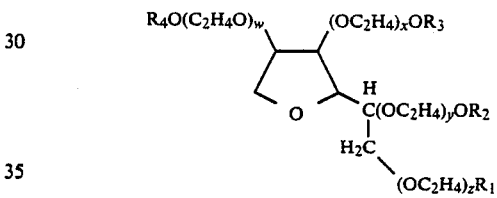

wherein $X+W+Y+Z$ is 20 and three of $R_1$, $R_2$, $R_3$ and $R_4$ represents stearate and the other of $R_1$, $R_2$, $R_3$ and $R_4$ is hydrogen; and T-MAZ 60K ® (a registered trademark of Mazer Chemicals, Inc. of Gurnee, Ill.) is a mixture of compounds defined according to the structure:

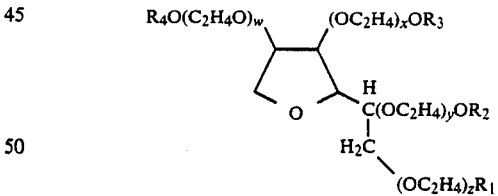

wherein $X+W+Y+Z$ is 20 and one of $R_1$, $R_2$, $R_3$ and $R_4$ is stearate and the other of $R_1$, $R_2$, $R_3$ and $R_4$ is hydrogen.

A requirement of our invention is that no reagents be present which would cause the reaction to give rise to a composition containing benzaldehyde or acetaldehyde which cannot be described as "natural". Thus, the use of substances such as hydrogen peroxide and/or sodium hydroxide in the reaction mass would give rise to a material not contemplated within the scope of our invention.

Thus, our invention specifically is intended to exclude processes such as those of the prior art, for example, Reeves, et al, Reeves, et al, TAPPI, 48(2), 121–5, (1965) which discloses the reaction:

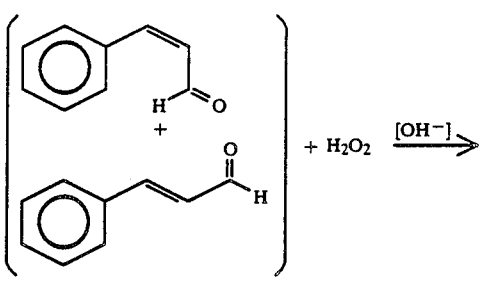

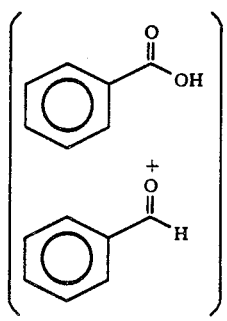

The reaction of our invention, to wit:

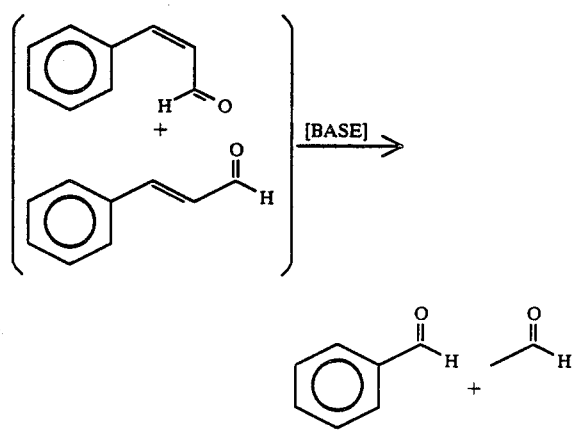

may be carried out in a standard reaction vessel preferably at reflux conditions (preferably when the cinnamaldehyde-bearing reactant is in the liquid phase, e.g., cinnamon oil or cassia oil); or it may be carried out using solid-liquid phase reaction equipment, e.g., "Soxhlet"-type equipment (preferably when the cinnamaldehyde-bearing reactant is in the solid phase). Thus, the reaction of our invention may be carried out with the aid of a "Soxhlet" extraction vessel with a portion of the reaction taking place in the "Soxhlet" thimble and a portion of the reaction taking place in a standard reaction vessel as more specifically described, infra. This is the case when, for example, pulverized cinnamon bark of one of the above types is intimately admixed with limestone or a natural lecithin and the resulting solid mixture is placed in the "Soxhlet" thimble.

In any case, the reaction may take place in the presence of (i) water or (ii) aqueous mixtures of $C_1-C_5$ alcohols and water. Examples of $C_1-C_5$ alcohols are methanol, ethyl alcohol, isopropyl alcohol, n-propyl alcohol, n-butanol, secondary butanol, tertiary butanol, n-amyl alcohol, t-amyl alcohol and isobutanol. The weight ratio of alcohol:water when an alcoholic solution is used, may vary, and is preferably from about 6 parts alcohol:4 parts water (by weight) up to about 1 part alcohol:about 10 parts water (by weight).

The reaction is carried out at temperatures such that acetaldehyde and benzaldehyde are removed from the reaction mass as they are formed thereby favoring the "retro-aldol" reaction. Hence, temperatures substantially greater than the boiling point of acetaldehyde are to be used. The boiling point of acetaldehyde is 21° C. at atmospheric pressure. Pressures are from about 0.2 atmospheres up to about 10 atmospheres may be used in carrying out this reaction. Thus, for example, refluxing water (containing nonionic sorbitan derivative emulsifier as defined, supra) at 1 atmosphere gives rise to a reaction temperature in the range of from about 90° C. up to about 100° C. whereas refluxing 50:50 ethanol:water at atmospheric pressure gives rise to a reaction temperature of about 80° C.

The reaction may be facilitated by means of bubbling or sparging steam into the reaction mass previously containing base, a natural cinnamaldehyde source and nonionic sorbitan derivative emulsifier as defined, supra.

The reaction temperature may thus vary from about 40° C. up to about 150° C. The reaction pressure may thus vary from about 0.2 atmospheres up to about 10 atmospheres. The reaction time may vary from about 5 hours up to about 80 hours. The longer the reaction time, the greater the degree of "completion" of the reaction (giving rise to a greater ratio of benzaldehyde:cinnamaldehyde in the final product). The shorter the period of reaction time the higher the temperature required in order to substantially "complete" the reaction (whereby the weight percent of benzaldehyde in the reaction mass is greater than about 40%).

Thus, within the meaning of our specification, the term "completion" of reaction means the formation in the reaction mass of at least a 10% yield of "natural" benzaldehyde and a 10% yield of acetaldehyde up to about a 95% of "natural" benzaldehyde and a 95% yield of "natural" acetaldehyde. Carrying out our process in order to yield less than 10% benzaldehyde or acetaldehyde or greater than 95% yield of benzaldehyde or acetaldehyde becomes uneconomical and is not contemplated within the scope of our invention.

When using as a source of cinnamaldehyde having one or both of the structures:

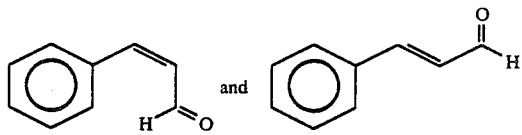

cinnamon oil or oil of cassia oil, the cinnamon oil or oil of cassia is admixed with water or a mixture of water and a $C_1-C_5$ lower alkanol as well as a food grade or natural nonionic emulsifier, preferably a nonionic sorbitan derivative emulsifier as defined, supra, e.g., TWEEN 20, TWEEN 40, TWEEN 60, TWEEN 80, SPAN 20, SPAN 40, SPAN 60, SPAN 80, T-MAZ 60K ® or T-MAZ 65K ®, base, e.g., sodium carbonate, sodium bicarbonate, potassium carbonate, potassium bicarbonate, lithium carbonate, lithium bicarbonate, calcium hydroxide, calcium carbonate, magnesium hydroxide, magnesium carbonate, proline having the structure:

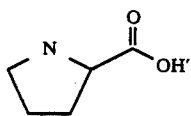

choline having the structure:

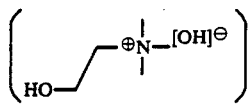

or a lecithin-base mixture with the lecithin having the structure:

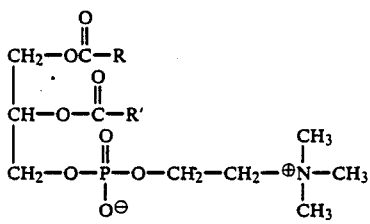

wherein the moieties:

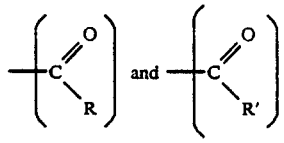

are defined, supra, the reaction mixture is then refluxed or heated for a period of between about 5 hours and about 80 hours. During the reaction, it is desirable to remove the benzaldehyde-rich reaction product as it is formed. Hence, the benzaldehyde-rich reaction product may be removed overhead through a packed vertical reflux column connected to a cooling heat exchanger as illustrated in FIGS. 7A, 7B, or 7C, infra or as illustrated in FIG. 13, infra. The distillate thus obtained exists in an emulsion which is subject to fractional steam distillation in order to yield products on fractional condensation of the steam distillation products; an upper aqueous phase and a lower more dense benzaldehyde-rich phase which can be separated from each other using a phase splitter; or the benzaldehyde-rich phase is separated from the aqueous phase, for example, by solvent extraction using such solvents as diethyl ether, dimethyl ether, hydrocarbons or methylene dichloride, and the benzaldehyde-rich phase may then be fractionally distilled.

The acetaldehyde may be separated from the benzaldehyde by means of the use of a high efficiency fractionation column and cooling heat exchanger. As will be seen in FIGS. 7A, or FIG. 13 the acetaldehyde may be separated by trapping said acetaldehyde in a "cold trap".

Thus, at the end of the reaction or at the end of the desired time period for proceeding with the reaction, the "natural" benzaldehyde and "natural" acetaldehyde are fractionally steam distilled yielding mixtures rich in natural benzaldehyde and/or acetaldehyde. The benzaldehyde-rich fraction may also contain a considerable proportion of unreacted cinnamaldehyde. This resulting product may, if desired, be again reacted in the presence of base, water and emulsifier and then again, fractionally steam distilled in order to enrich the benzaldehyde stream. From a practical standpoint such a mixture of cinnamaldehyde and benzaldehyde produced according to the first fractional steam distillation is usually adequate for use in food flavors, for example, or in tobacco flavors, for example.

Normally, but not necessarily, the acetaldehyde is prepared free of aromatic aldehydes for use in food flavors.

From a practical standpoint, the mixtures of acetaldehyde, benzaldehyde and cinnamaldehyde thus produced have unobvious, unexpected and advantageous properties for augmenting or enhancing the aroma or taste of consumable materials including but not limited to foodstuffs, chewing gums, medicinal products, toothpastes, chewing tobaccos, smoking tobacco and smoking tobacco articles, particularly almond, orange and cherry flavored foodstuffs and medicinal products.

The range of mole ratio base to cinnamaldehyde (contained in the cinnamaldehyde-bearing natural substance, e.g., cassia oil, cinnamon bark, cinnamon leaf and the like) may vary from about 0.1:1 up to about 4:1. This mole ratio is based upon the following:

(a) Whether the reaction is carried out on a solid containing the cinnamaldehyde such as pulverized cinnamon bark or in admixture a the base such as magnesium hydroxide (in which case the higher end of the range of mole ratios is applicable); or whether the reaction is a liquid phase reaction carried out in the presence of a base such as choline, proline or aqueous sodium bicarbonate with cinnamon oil and (i) water or (ii) an aqueous alcohol mixture (in which case the mole ratio of base:cinnamaldehyde is at the lower end of the abovementioned range);

(b) The nature of the total energy input to the reaction; based upon heat input and time of reaction as well as temperature and pressure of reaction (thus, a relatively long time of reaction (e.g., 80 hours) will give rise to a higher "yield" of benzaldehyde and acetaldehyde in the reaction product and a lower concentration of cinnamaldehyde in the reaction product). Depending upon the flavorist's requirements, it may be desirable to create an ultimate composition containing, for example, greater than 80% benzaldehyde or a 50:50 mixture or benzaldehyde and cinnamaldehyde or substantially pure acetaldehyde (having present therewith minor quantities of other low boiling components such as crotonaldehyde and acetic acid); and (c) The particle size (where applicable) of the solid source of cinnamaldehyde, e.g., pulverized cinnamon bark or pulverized high cinnamaldehyde-containing cinnamon leaf). A small particle size will give rise to a faster conversion of cinnamaldehyde (contained in the solid cinnamaldehyde-bearing source to benzaldehyde and acetaldehyde.

With respect to the amount of natural or food grade nonionic emulsifier, preferably sorbitan derivative nonionic emulsifier, e.g., TWEEN 20, TWEEN 40, TWEEN 60, TWEEN 80, SPAN 40, SPAN 60, SPAN 20, SPAN 80, T-MAZ 60K ®, or T-MAZ 65K ®, it is preferred that between about 1% up to about 6% by weight of the reaction mass be emulsifier and about 70 up to 90% by weight of the reaction mass be water, with lower quantities of water being used (down to a minimum of 50% of the reaction mass) when mixtures of water and alcohol are used in the reaction mass.

In all cases our invention is capable of yielding in a controllable fashion desired ratios of benzaldehyde and acetaldehyde to cinnamaldehyde depending upon the reaction conditions employed.

Nevertheless, careful analysis of the reaction products produced using the foregoing parameters yields very small amounts of "natural" byproducts, e.g., compounds having the structures:

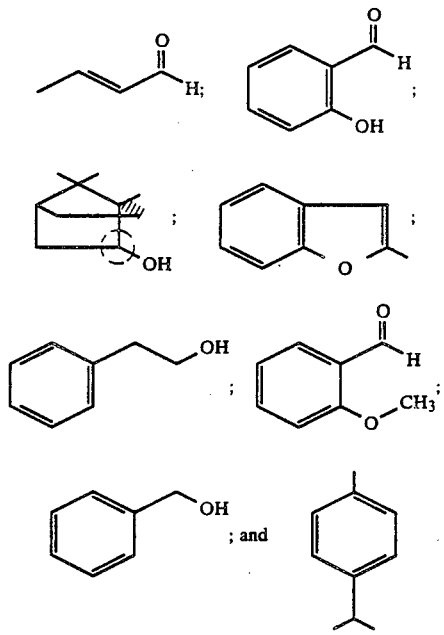

as will be shown in the description of the analysis of the steam distillation product in Example XXVI, infra.

The reaction product containing the cinnamaldehyde, benzaldehyde and acetaldehyde produced according to the reaction:

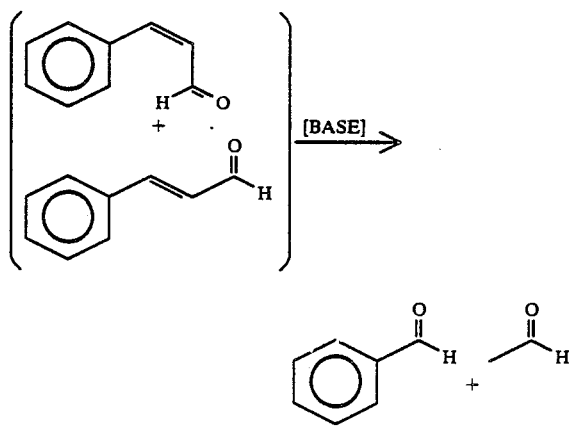

may be considered as a "natural" product. This "natural" product may be used "as is" or it may preferably be physically purified by such methods as fractional steam distillation and/or preparative chromatography. The resulting "natural" products will have novel utilities in augmenting or enhancing the aroma or taste of consumable materials including but not limited to foodstuffs, chewing gums, medicinal products, toothpastes, chewing tobaccos and smoking tobaccos particularly cherry flavored, orange flavored, almond flavored foodstuffs and medicinal products. Accordingly, for example, compositions of matter containing mole ratios of from about 10:90 up to about 99.9:0.1 of benzaldehyde:cinnamaldehyde in their natural state prepared according to the reaction:

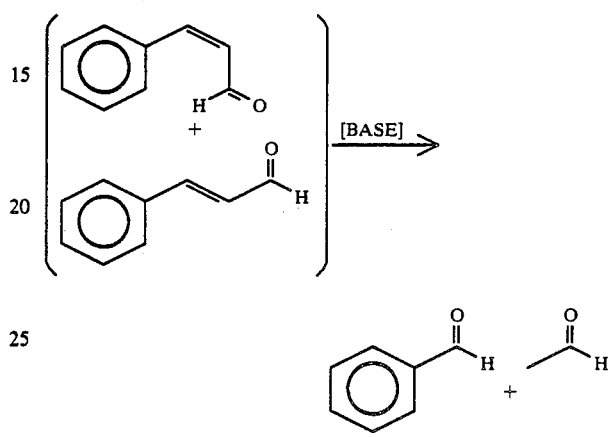

may be utilized in such consumable materials, e.g., foodstuffs as, for example, macaroon cookies, maraschino cherries, cherry flavored beverages such as carbonated cherry drinks, and the like.

Furthermore, substantially pure acetaldehyde containing minor amounts of impurities may be utilized in such consumable materials, e.g., foodstuffs such as orange drinks.

Collectively, these aforementioned benzaldehyde, cinnamaldehyde and acetaldehyde-containing products of our invention are hereinafter called "aldehyde-containing compositions".

The novel products of our invention may be utilized in foodstuffs and beverages in an amount of from about 0.5 ppm up to about 3% by weight of the resulting foodstuff or beverage. The materials can be used in such high percentages because of the manner in which they are produced; that is, free of any nitrile-containing substances as would be present if the aldehyde-containing products were produced from such materials as apricot kernels.

As used herein, the term "foodstuff" includes both solid and liquid ingestible materials which usually do, but need not, have nutritional value. Thus, foodstuffs includes soups, convenience foods, beverages, dairy products, candies, vegetable cereals, soft drinks, snacks and the like.

A used herein, the term "medicinal products" includes both solids and liquids which are ingestible nontoxic materials which have medicinal value such as cough syrups, cough drops and chewing medicinal tablets.

The term "chewing gum" is intended herein to be a foodstuff composition comprising a substantially water-insoluble, chewable plastic gum base such as chicle, or substitutes therefor, including jelutong, guttakay, rubber or certain comestible natrual·or synthetic resins or waxes. Incorporated with the gum base in admixture therewith may be plasticizers or softening agents, e.g., glycerine and a flavoring composition which incorporates one or more of the aldehyde-containing compositions of our invention and, in addition, sweetening agents which may be sugars, including sucrose or dextrose and/or artificial sweeteners such as cyclamates or saccharin. Other optional ingredients may be present.

The term "augment" in its various forms is used herein to mean the supplying, modifying or imparting of a flavor or aroma characteristic note or nuance to an otherwise bland, relatively tasteless or non-odorous substance or modifying an existing flavor or aroma characteristic where the natural flavor is deficient in some regard, or supplementing the existing flavor or aroma impression to modify its quality, character, taste or aroma.

The term "enhance" is used herein to mean the intensification of a flavor or aroma characteristic or note without the modification of the quality thereof. Thus, "enhancement" of a flavor or aroma means that the enhancement agent does not add any additional flavor note or nuance.

Substances suitable for use herein as co-ingredients or flavoring adjuvants are well known in the art for such use, being extensively described in the relevant literature. It is required that any such material be "ingestibly acceptable" and thus non-toxic or otherwise non-deleterious, particularly from an organoleptic standpoint whereby the ultimate flavor and/or aroma of the consumable material used does not cause the consumable material to have unacceptable aroma and taste nuances.

It is a further requirement that such material be organoleptically compatible with the foodstuff with which it is used so that the flavor and aroma nuances of such material, taken together with the flavor and aroma nuances of the foodstuff (as a whole) give rise to a harmoniously aesthetically pleasing aroma and taste profile. Such material, in general, may be characterized as flavoring adjuvants or vehicles comprising broadly, stabilizers, thickeners, surface active agents, conditioners, other flavorants and flavor intensifiers.

Stabilizer compounds include preservatives, e.g., sodium chloride; antioxidants, e.g., calcium and sodium ascorbate, ascorbic acid, butylated hydroxyanisole (mixture of 2- and 3-tertiary-butyl-4-hydroxyanisole), butylated hydroxy toluene (2,6-di-tertiary-butyl-4-methyl phenol), propyl gallate and the like and sequestrants, e.g., citric acid.

Thickener compounds include carriers, binders, protective colloids, suspending agents, emulsifiers and the like, e.g., agar agar, carrageenan, cellulose and cellulose derivatives such as carboxymethyl) cellulose and methyl cellulose; natural and synthetic gums such as gum arabic, gum tragacanth, gelatin, proteinaceous materials; lipids; carbohydrates; starches, pectins and emulsifiers, e.g., mono- and diglycerides of fatty acids, skim milk powder, hexoses, pentoses, disaccharides, e.g., sucrose, corn syrup and the like.

Surface active agents include emulsifying agents, e.g., fatty acids such as capric acid, caprylic acid, palmitic acid, myristic acid and the like, mono- and diglycerides of fatty acids, lecithin, defoaming and flavor dispersing agents such as sorbitan monostearate, potassium stearate, hydrogenated tallow alcohol and the like.

Conditioners include compounds such as bleaching and maturing agents, e.g., benzoyl peroxide, calcium peroxide, hydrogen peroxide and the like, starch modifiers such as peracetic acid, sodium chlorite, sodium hypochlorite, propylene oxide, succinic anhydride and the like, buffers and neutralizing agents, e.g., sodium acetate ammonium bicarbonate, ammonium phosphate, citric acid, lactic acid, vinegar and the like, colorants, e.g., carminic acid, cochineal, tumeric and curcumin and the like, firming agents such as aluminum sodium sulfate, calcium chloride and calcium glyconate, texturizers, anti-caking agents, e.g., aluminum calcium sulfate and tribasic calcium phosphate, enzymes, yeast foods, e.g., calcium lactate and calcium sulfate, nutrient supplements, e.g., iron salts such as ferric phosphate, ferrous gluconate and the like, riboflavin, vitamins, zinc sources such as zinc chloride, zinc sulfate and the like.

Other flavorants and flavor intensifiers include organic acids, e.g., acetic acid, formic acid, 2-hexenoic acid, benzoic acid, n-butyric acid, caproic acid, caprylic acid, cinnamic acid, isobutyric acid, isovaleric acid, alpha-methyl-butyric acid, propionic acid, valeric acid, 2-methyl-2-pentenoic acid, and 2-methyl-cis-3-pentenoic acid; ketones and aldehydes other than the benzaldehyde and cinnamaldehyde of our invention, e.g., acetaldehyde, acetophenone, acetone, acetyl methyl carbinol, acrolein, n-butanal, crotonal, diacetyl, beta,-betadimethyl-acrolein, n-hexanal, 2-hexanal, cis-3-hexenal, 2-heptenal, 4-(p-hydroxphenyl)-2-butanone, alpha-ionone, beta-ionone, 2-methyl-3-butanone, 2-pentanone, 2-pentenal and propanal; alchols such as 1-butanol, benzyl alcohol, 1-borneol, trans-2-buten-1-ol, ethanol, geraniol, 1-hexanol, 2-heptanol, trans-2-hexenol-1, cis-3-hexen-1-ol, 3-methyl-3-buten-1-ol, 1-pentanol, 1-penten-3-ol, p-hydroxyphenyl-2-ethanol, isoamyl alcohol, isofenchyl alcohol, phenyl-2-ethanol, alpha-terpineol, cis-terpineol hydrate, esters, such as butyl acetate ethyl acetate, ethyl acetoacetate; ethyl benzoate, ethyl butyrate, ethyl cinnamate, ethyl crotonate, ethyl formate, ethyl isobutyrate, ethyl isovalerate, ethyl alpha-methylbutyrate, ethyl propionate, ethyl salicylate, trans-2-hexenyl acetate, hexyl acetate, 2-hexenyl butyrate, hexyl butyrate, isoamyl acetate, isopropyl butyrate, methyl acetate, methyl butyrate, methyl caproate, methyl isobutyrate, methyl-2-methyl-butyrate, propyl acetate, amyl acetate, amyl butyrate, benzyl salicylate, dimethyl anthranilate, ethyl methylphenylglycidate ethyl succinate isobutyl cinnamate and terpenyl acetate; essential oils such as jasmin absolute, rose absolute, orris absolute, lemon essential oil, Bulgarian rose, yara yara, natural raspberry oil and vanilla; lactones, sulfides, e.g., methyl sulfide and other materials such as maltol, acetoin and acetals (e.g., 1,1-diethoxyethane, 1,1-dimethoxyethane and dimethoxymethane.

The specific flavoring adjuvant selected for use may be either solid or liquid depending upon the desired physical form of the ultimate product, i.e., foodstuff, whether simulated or natural, and should, in any event, be capable of providing an environment in which the cyclic chemical compounds can be dispersed or admixed to provide a homogeneous medium. In addition, selection of one or more flavoring adjuvants, as well as the quantities thereof will depend upon the precise organoleptic character desired in the finished product. Thus, in the case of flavoring compositions, ingredient selection will vary in accordance with the foodstuff to which the flavor and aroma are to be imparted. In contradistinction, in the preparation of solid products, e.g., simulated foodstuffs, ingredients capable of providing normally solid compositions should be selected such as varioua cellulose derivatives.

As will be appreciated by those skilled in the art, the amount of aldehyde-containing composition employed in a particular instance can vary over a relatively wide range whereby its desired organoleptic effects (having reference to the nature of the product) are achieved. Thus, correspondingly greater amounts would be necessary in those instances wherein the ultimate food composition to be flavored is relatively bland to the taste, whereas relatively minor quantities may suffice for purposes of enhancing the composition merely deficient in natural flavor or aroma. The primary requirement is that the amount selected (to be effective) be sufficient to augment or enhance the organoleptic characteristics of the parent composition (whether foodstuff per se or flavoring composition).

The use of insufficient quantities of aldehyde-containing composition of our invention, will, of course, substantially vitiate any possibility of obtaining the desired results while excess quantities prove needlessly costly and in extreme cases, may disrupt the flavor-aroma balance, thus proving self-defeating. Accordingly, the terminology "effective amount" and "sufficient amount" is to be accorded a significance in the context of the present invention consistent with the obtention of desired flavoring effects.

Thus, and with respect to ultimate food composition, it is found that quantities of aldehyde-containing composition of our invention ranging from a small but effective amount, e.g., 0.5 ppm up to 3% by weight based on total composition are suitable as stated, supra. Concentrations in excess of the maximum quantity stated are not normally recommended, since they fail to provide commensurate enhancement of organoleptic properties. In those instances where the aldehyde-containing composition of our invention is added to the foodstuff as an integral component of a flavoring composition, it is, of course, essential that the total quantity of flavoring composition employed be sufficient to yield an effective amount of aldehyde-containing composition.

Food flavoring compositions prepared in accordance with the present invention preferably contain the aldehyde-containing composition of our invention ranging from about 0.1% up to about 100% by weight based on the total weight of said flavoring composition.

The compositions described herein can be prepared according to conventional techniques well known as typified by cake batters and fruit drinks and can be formulated by merely admixing the involved ingredients within the proportions stated in a suitable blender to obtain the desired consistency, homogeneity of dispersion, etc. Alternatively, flavoring compositions in the form of particulate solids can be conveniently prepared by mixing the aldehyde-containing composition of our invention with, for example, gum arabic, gum tragacanth, carrageenan and the like, and thereafter spray-drying the resultant mixture whereby to obtain the particulate solid product. Pre-prepared flavor mixes in powder form, e.g., a fruit flavored powdered mix, are obtained by mixing the dried solid components, e.g., starch, sugar and the like and benzaldehyde/cinnamaldehyde composition in a dry blender until the requisite degree of uniformity is achieved.

The novel aldehyde composition-containing substances produced according to the novel process of our invention may be used "as is" as stated, supra or may be used in conjunction with other flavor adjuvants including but not limited to:
Heliotropin;
Terpinenol-4;
Anisaldehyde;
Phenyl acetaldehyde;
Benzyl formate;
Benzyl acetate;
Cis-3-hexenyl benzoate;
Methyl Hexanoate;
Hexanal;
Eucalyptol;
Eugenol;
Ethyl acetate;
Ethyl butyrate;
Turpentine gum oil;
Limonene;
Gum camphor;
Isobornyl acetate;
Borneol;
Cinnamic aldehyde;
Cuminic aldehyde;
Furfural;
Methyl cinnamate;
Cassia oil;
Vanillin;
Maltol;
Parahydroxybenzylacetone;
Dimethyl sulfide;
Alpha-ionone;
Acetic acid;
Isobutyl acetate;
Acetone;
Butyric acid;
Formic acid;
Valeric acid;
Amyl acetate;
Amyl butyrate;
Anethol;
Benzyl salicylate;
Diacetyl;
Dimethyl anthranilate;
Ethyl methylphenylglycidate;
Ethyl succinate;
Ethyl valerate;
Geraniol;
Cis-3-hexen-1-ol;
2-Hexenyl acetate;
2-Hexenyl butyrate;
Hexyl butyrate;
4-(p-Hydroxyphenyl)-2-butanone;
Beta-ionone;
Isobutyl cinnamate;
Jasmine;
Lemon essential oil;
Methy butyrate;
Methyl capronate;
Methyl disulfide;
Methyl p-naphthyl ketone;
Orris butter;
Rose absolute;
Terpenyl acetate;
Gamma-undecalactone;
Vanilla;
Alcohol;
Oil of Cubeb;
Phellandrene;
Beta-phellandrene;
Oil of Coriander;
Oil of Pimento Leaf;
Oil of Patchouli;

Alpha-Pinene;
Beta-Pinene;
Beta-caryophyllene;
Dihydrocarveol;
Piperonal;
Piperine;
Chavicine;
Piperidine;
Oil of Black Pepper;
Black Pepper Oleoresin;
Capsicum;
Oil of Nutmeg;
Cardamon oil;
Clove Oil;
Spearmint Oil; and
Oil of Peppermint.

An additional aspect of our invention provides an organoleptically improved smoking tobacco product and additives therefor, as well as methods of making the same which overcome specific problems heretofore encountered in which specific desired sweet and fruity flavor characteristics of natural tobacco are created or enhanced and may be readily controlled and maintained at the desired uniform level regardless of variations in the tobacco components of the blend.

This invention further provides improved tobacco additives and methods whereby various desirable sweet and fruity flavoring characteristics may be imparted to smoking tobacco products and may be readily varied and controlled to produce the desired uniform flavoring characteristics.

In carrying out this aspect of our invention, we add to smoking tobacco materials or a suitable substitute therefor (e.g., dried lettuce leaves) or we add to filters for smoking tobacco articles (e.g., cellulose acetate filters) an aroma and flavor additive containing as an active ingredient the benzaldehyde/cinnamaldehyde composition of our invention.

In addition to the benzaldehyde/cinnamaldehyde composition of our invention other flavoring and aroma additives may be added to the smoking tobacco material or substituted therefor either separately or in admixture with the benzaldehyde/cinnamaldehyde composition of our invention as follows:

I. SYNTHETIC MATERIALS

Beta-ethyl-cinnamaldehyde;
Eugenol;
Dipentene;
Beta-Damascenone;
Maltol;
Ethyl maltol;
Delta undecalactone;
Delta decalactone;
Amyl acetate;
Ethyl butyrate;
Ethyl valerate;
Ethyl acetate;
2-Hexenol;
1,2-Methyl-5-isopropyl-1,3-nonadiene-8-one;
2,6-Dimethyl-2,6-undecadiene-10-one;
2-Methyl-5-isopropyl acetophenone;
2-Hydroxy-2,5,5,8a-tetramethyl-1-(2-hydroxyethyl)-decahydronaphthalene;
Dodecahydro-3a,6,6,9a-tetramethyl naptho-[2,1-b]-furan;
4-Hydroxy hexanoic acid, gamma lactone;
Polyisoprenoid hydrocarbons defined in Example V of U.S. Pat. No. 3,589,372 issued on June 29, 1971.

II. Natural Oils

Celery seed oil;
Coffee extract;
Bergamot Oil;
Cocoa extract;
Nutmeg oil;
Origanum oil.

An aroma and flavoring concentrate containing the benzaldehyde/cinnamaldehyde composition of our invention and, if desired, one or more of the above indicated additional flavoring materials may be added to the smoking tobacco material, to the filter or to the leaf or paper wrapper. The smoking tobacco material may be shredded, cured, cased and blended tobacco material or reconstituted tobacco material or tobacco substituents (e.g., lettuce leaves) or mixtures thereof. The proportions of flavoring additives may be varied in accordance with taste but insofar as enhancement or the imparting of natural and/or sweet notes, we have found that satisfactory results are obtained if the proportion by weight of the sum total of the benzaldehyde/cinnamaldehyde composition of our invention to smoking tobacco material is between 5 and 100 ppm (0.0005–0.01%) of the active ingredients to the smoking tobacco material. We have further found that satisfactory results are obtained if the proportion by weight of the sum total of benzaldehyde/cinnamaldehyde composition of our invention used to flavoring material is between 50 and 1000 ppm (0.005–0.1%).

Any convenient method for incorporating the benzaldehyde/cinnamaldehyde composition of our invention in the tobacco product may be employed. Thus, the benzaldehyde/cinnamaldehyde composition of our invention taken alone or along with other flavoring additives may be dissolved in a suitable solvent such as ethanol, pentane, diethyl ether and or other volatile organic solvents and the resulting solution may ither be spread on the cured, cased and blended tobacco material or the tobacco material may be dipped into such solution. Under certain circumstances, a solution of the benzaldehyde/cinnamaldehyde composition of our invention taken alone or taken further together with other flavoring additives as set forth above, may be applied by means of a suitable applicator such as a brush or roller on the paper or leaf wrapper for the smoking product, or it may be applied to the filter by either spraying, or dipping or coating.

Furthermore, it will be apparent that only a portion of the tobacco or substituted therefor need be treated and the thus treated tobacco may be blended with other tobaccos before the ultimate tobacco product is formed.

In such cases, the tobacco treated may have the benzaldehyde/cinnamaldehyde composition of our invention in excess of the amounts or concentrations above indicated so that when blended with other tobaccos, the final product will have the percentage within the indicated range.

In accordance with one specific example of our invention, an aged, cured and shredded domestic burley tobacco is spread with a 20% ethyl alcohol solution of a mixture containing 75% benzaldehyde and 25% cinnamaldehyde prepared by carrying out a reaction in apparatus of the type set forth in FIG. 7B using an $NaHCO_3$ catalyst, water and a TWEEN 80 (described, supra) emulsifying agent, followed by fractional steam distillation.

The amount of benzaldehyde/cinnamaldehyde composition is 20 ppms on a dry basis. Thereafter, the alcohol is removed by evaporation and the tobacco is manufactured into cigarettes by the usual techniques. The cigarette when treated as indicated has a desired and pleasing sweet and fruity aroma with faint aesthetically pleasing cherry nuances which is detectable in the main and side streams when the cigarette is smoked. The aroma is described as being sweeter, rich, less harsh, more tobacco-like and having fruity notes.

While our invention is particularly useful in the manufacture of smoking tobacco, such as cigarette tobacco, cigar tobacco and pipe tobacco, other tobacco products formed from sheeted tobacco dust or fines may also be used. Likewise, the benzaldehyde/cinnamaldehyde compositions of our invention can be incorporated with materials such as filter tip materials, seam paste, packaging materials and the like which are used along with tobacco to form a product adapted for smoking. Furthermore, the benzaldehyde/cinnamaldehyde compositions of our invention can be added certain tobacco substitutes of natural or synthetic origin (e.g., dried lettuce leaves) and, accordingly, by the term "tobacco" as used throughout this specification is meant any composition intended for human consumption by smoking or otherwise, whether composed of tobacco plant parts or substitute materials or both.

BRIEF DESCRIPTION OF THE DRAWINGS

FIG. 4 is a cut-away cross sectional elevation view of a Soxhlet apparatus used for carrying out the reaction:

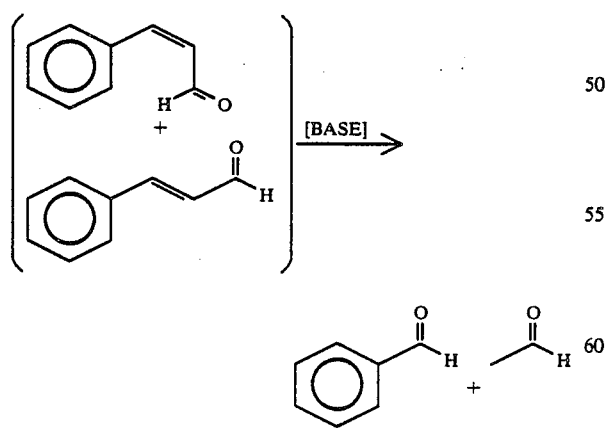

when the cinnamaldehyde is present in a solid material such as pulverized cinnamon bark and when the basic catalyst is a solid such as magnesium hydroxide or calcium hydroxide.

FIG. 5 is a simplified Soxhlet reaction apparatus fitting for carrying out the reaction:

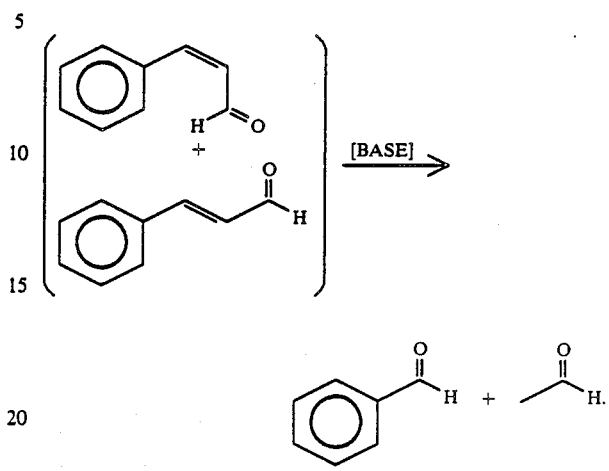

Figure 6:
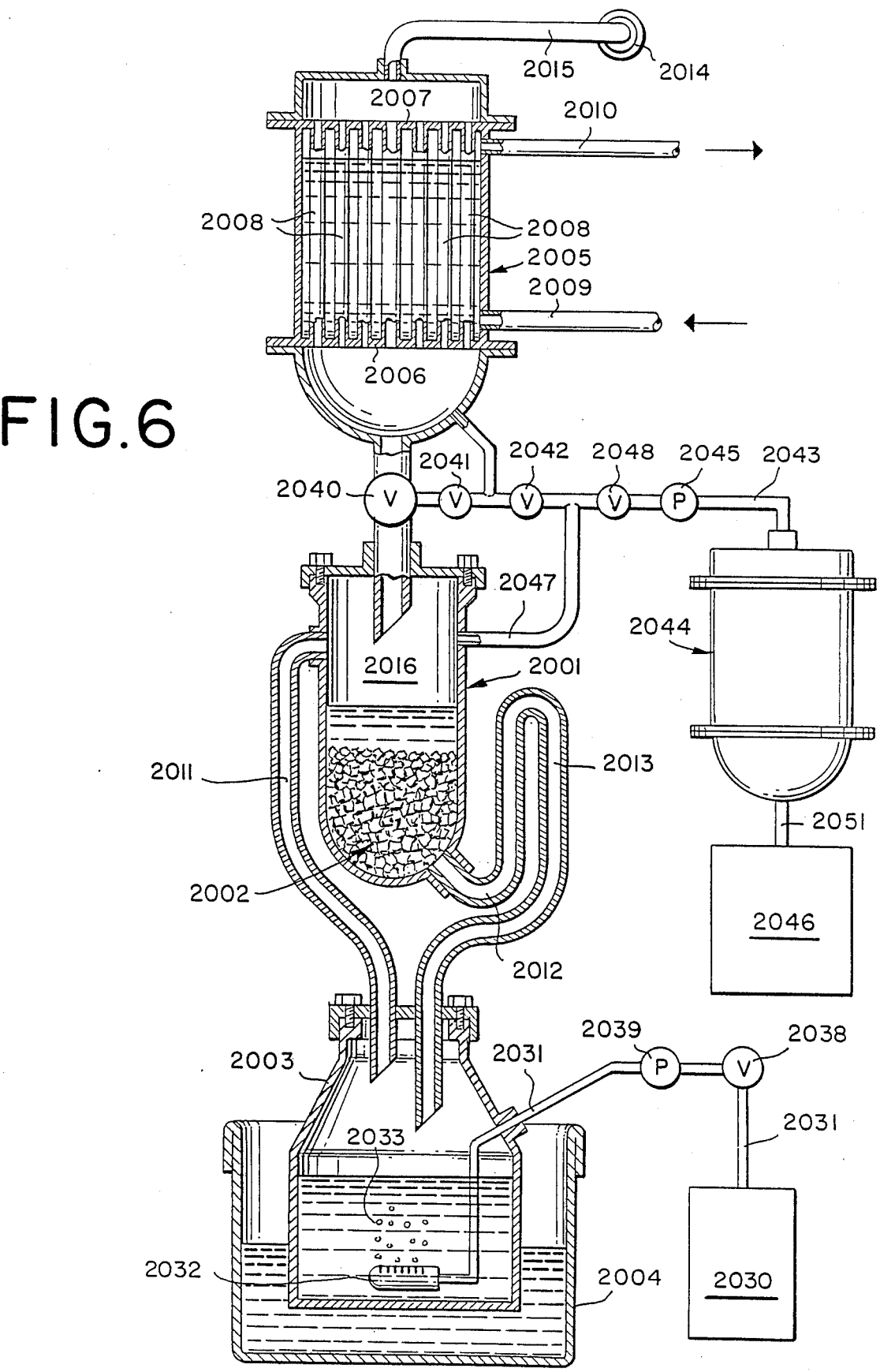

FIG. 6 is a diagram of a solid-liquid phase reaction apparatus useful in carrying out the retro-aldol reaction, to wit:

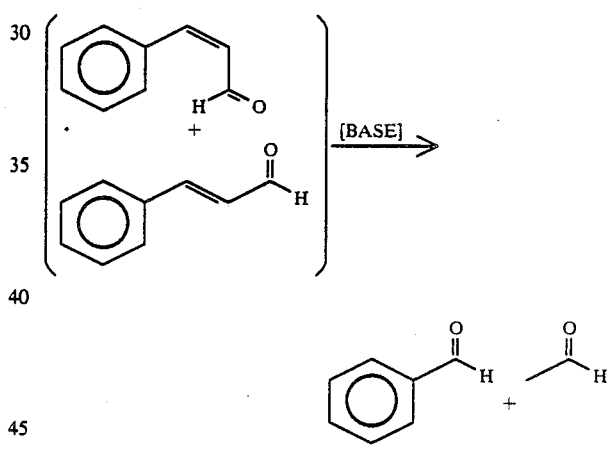

when the cinnamaldehyde having the structure:

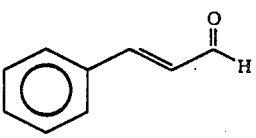

or or a mixture thereof is in existence in a natural solid material such as cinnamon bark.

Figures 7A, 7B:
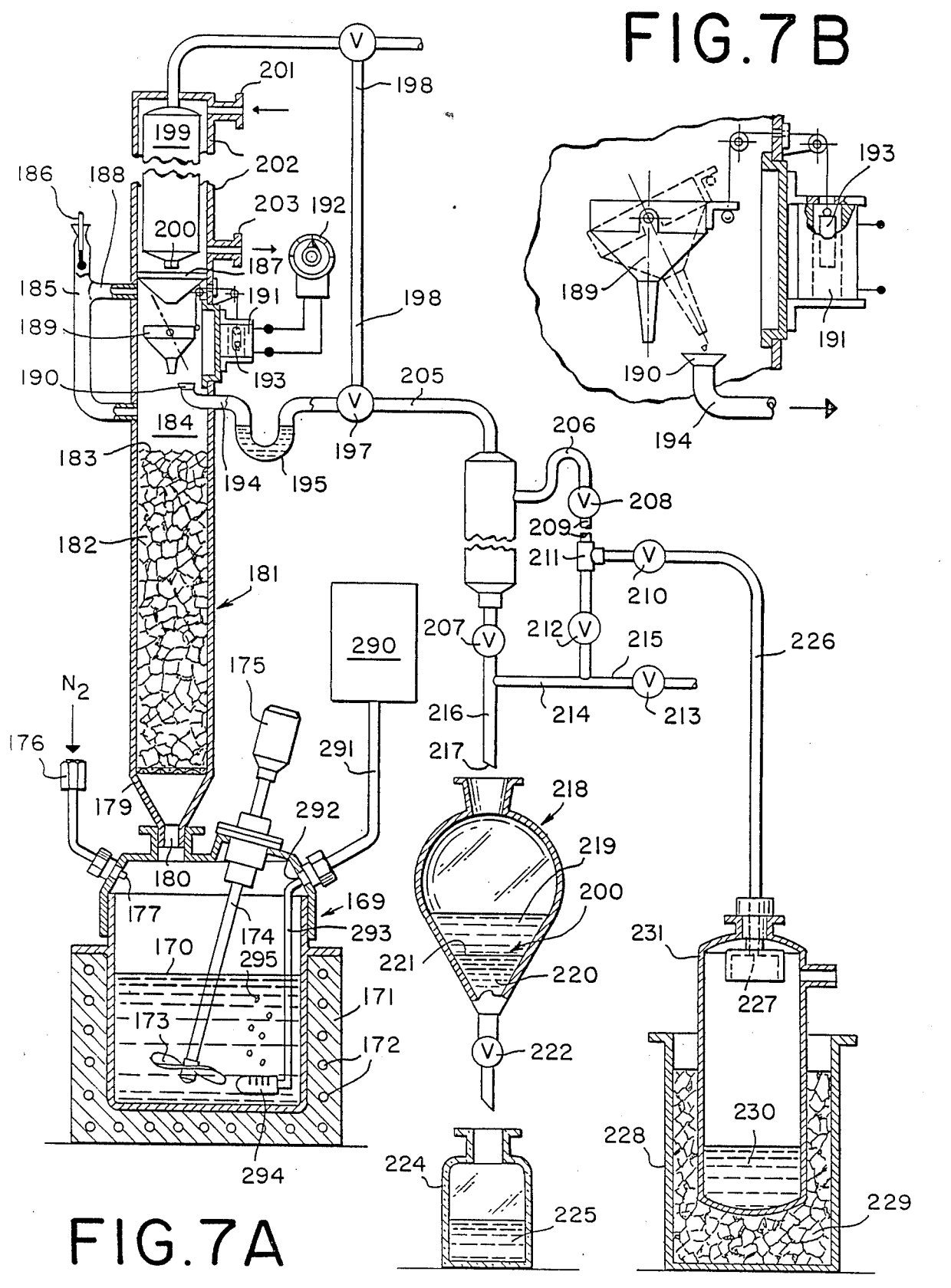

FIG. 7A is a diagram of a liquid-liquid phase apparatus for carrying out the reaction:

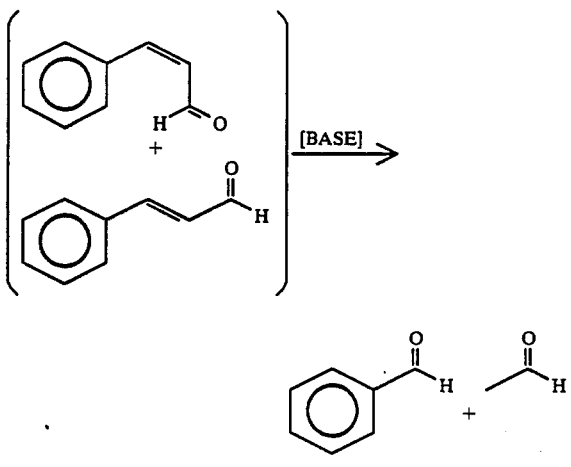

and recovering the natural benzaldehyde-containing composition and the natural acetaldehyde-containing composition of our invention (as employed in Example VI, infra).

FIG. 7B is a diagram of a section of the apparatus of FIG. 7A showing the magnetic coil-actuated recovery-return mechanism of the apparatus useful in the practice of our invention.

Figure 7C:
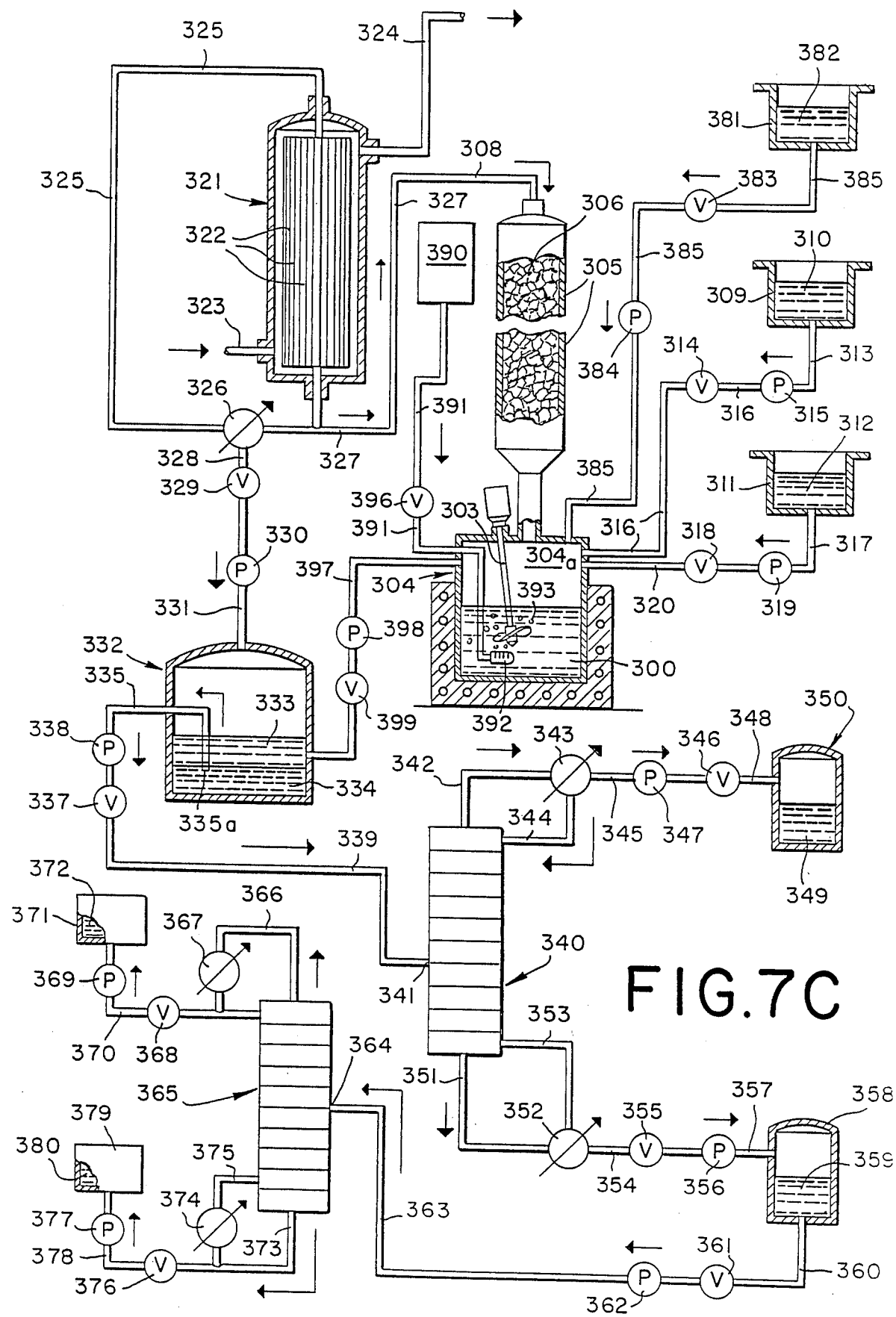

FIG. 7C is a diagram of a continuous liquid-liquid phase reaction-recovery apparatus for carrying the reaction:

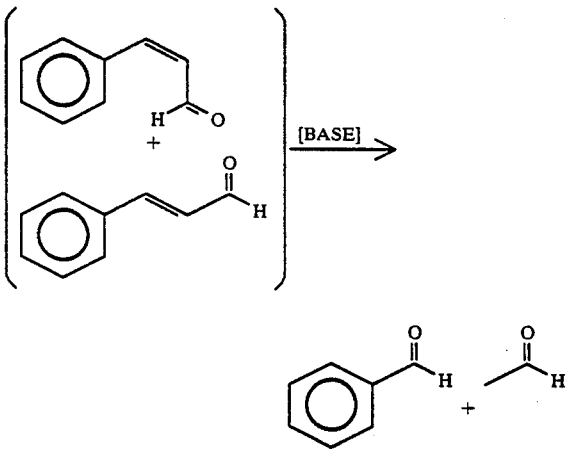

and recovering the natural benzaldehyde-containing composition and natural acetaldehyde-containing composition of our invention.

Figure 8:
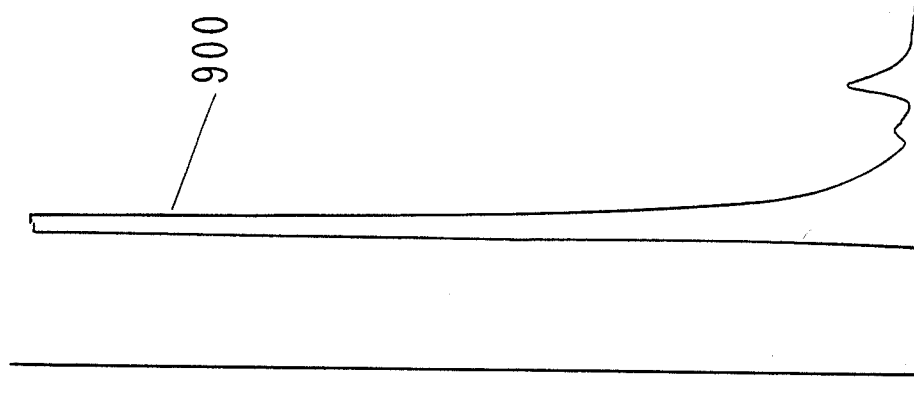

FIG. 8 is the GLC profile of the reaction product produced according to Example VI containing benzaldehyde and cinnamaldehyde.

Figure 9:
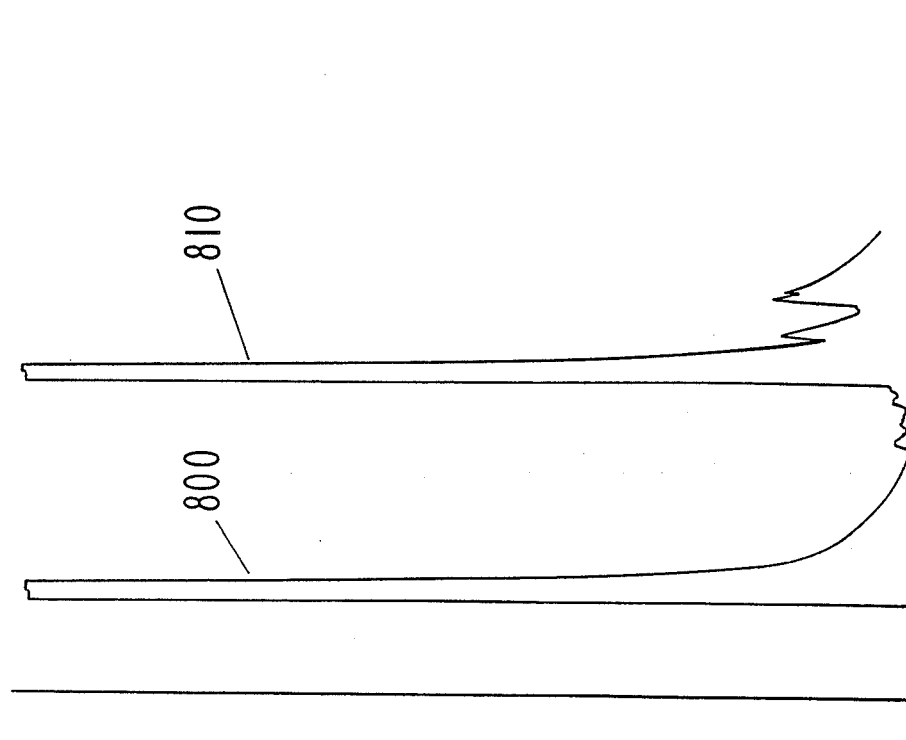

FIG. 9 is the GLC profile of a first distillation product of the reaction product of Example VI rich in benzaldehyde.

Figure 10:
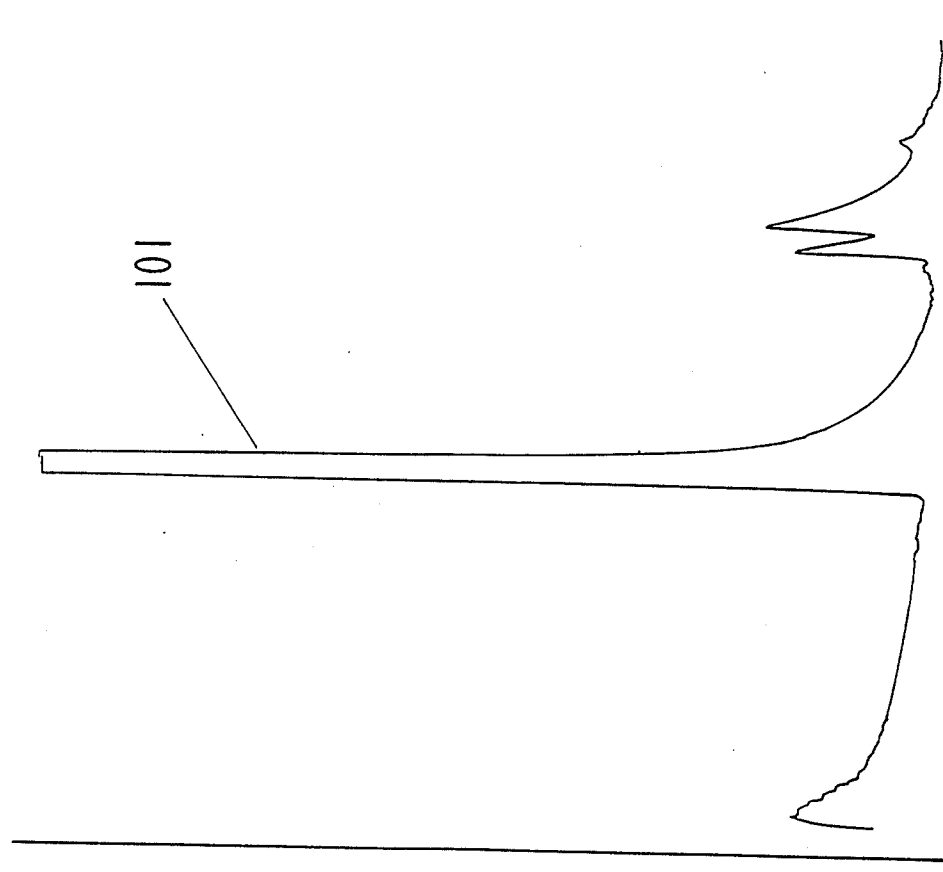

FIG. 10 is the GLC profile of a second distillation product of the reaction product of Example VI rich in benzaldehyde.

Figure 11:
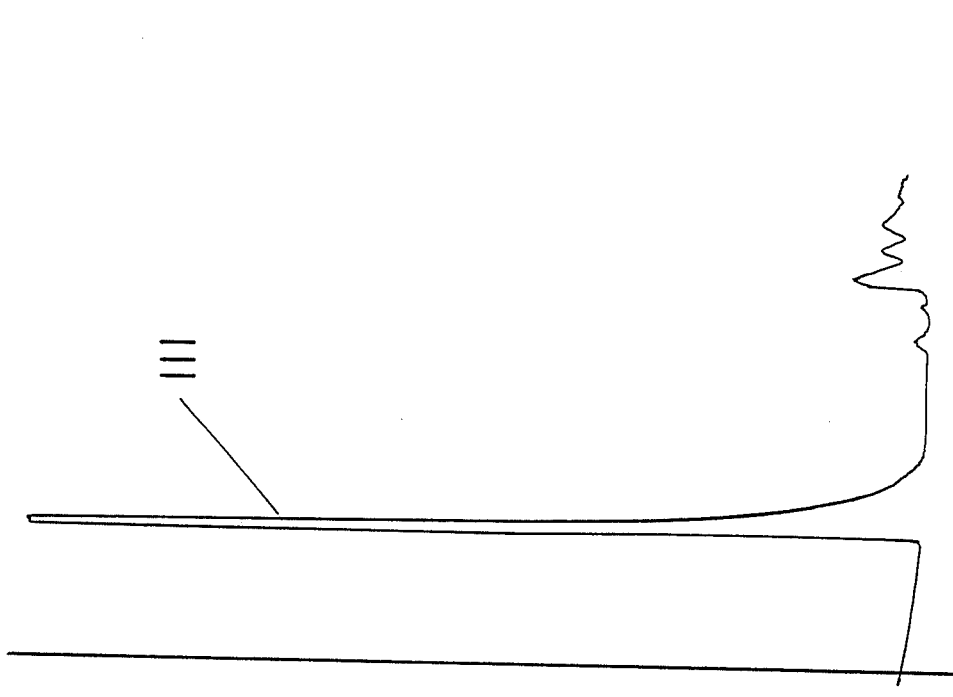

FIG. 11 is the GLC profile of a third distillation product of the reaction product of Example VI rich in benzaldehyde.

FIG. 12 is a total ion current spectrum of a GC-MS analysis of acetaldehyde-rich product recovered in cold trap 231 of the apparatus of FIG. 7A.

Figure 13:
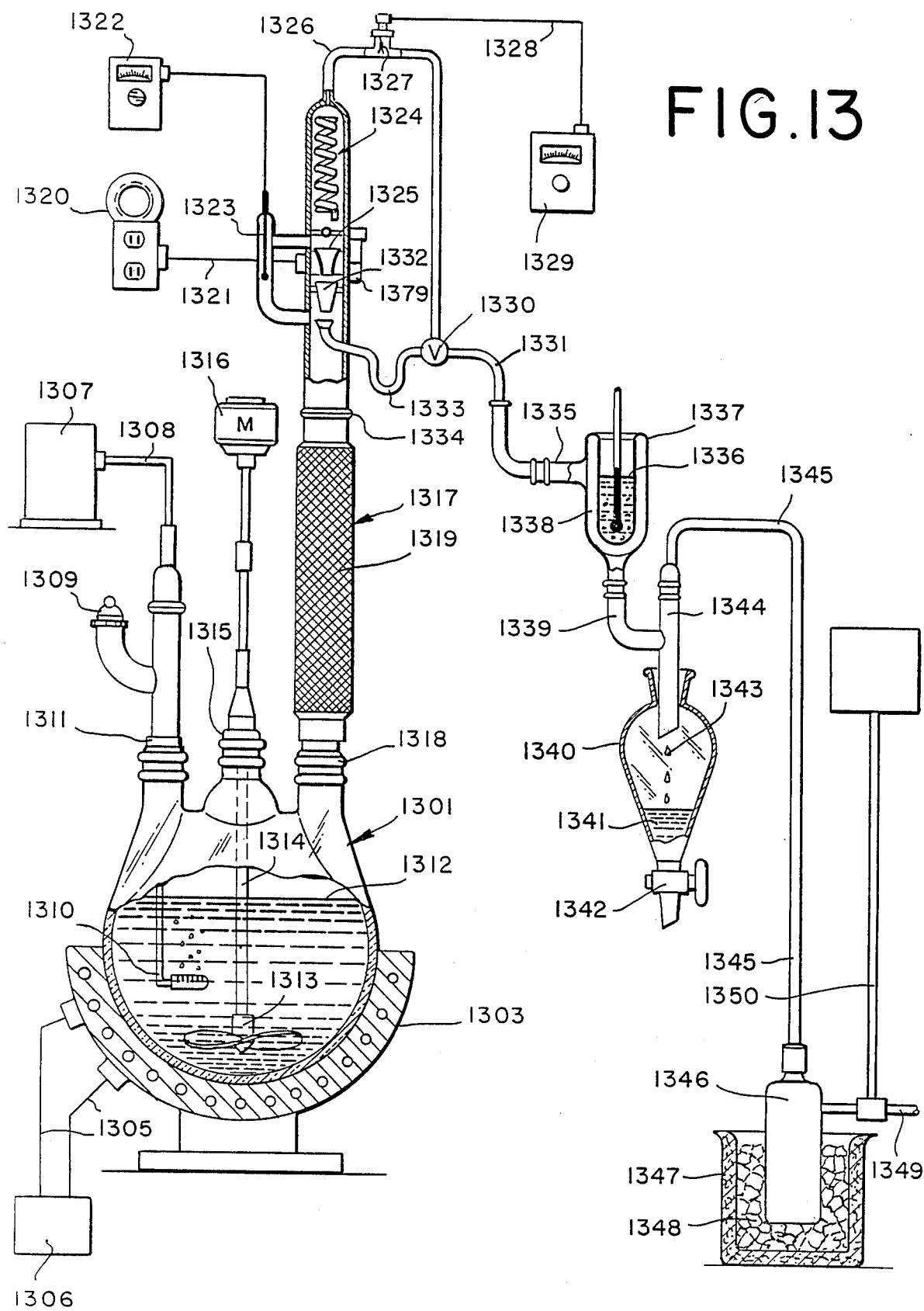

FIG. 13 is a diagram of a liquid-liquid phase reaction and recovery laboratory apparatus for carrying out the reaction:

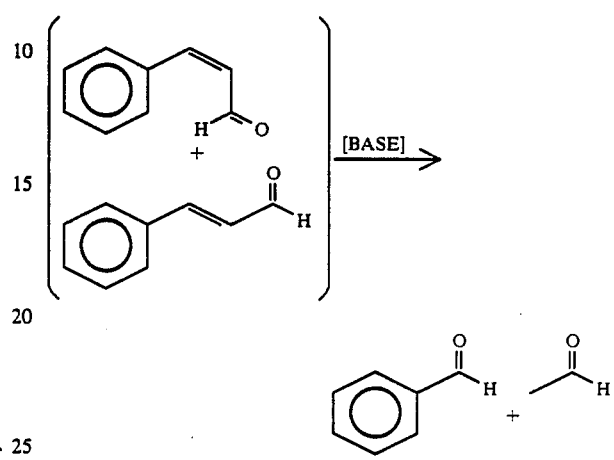

and recovering the natural benzaldehyde-containing composition and the natural acetaldehyde-containing composition of our invention (as employed in Example XXIV, infra).

Figure 14:
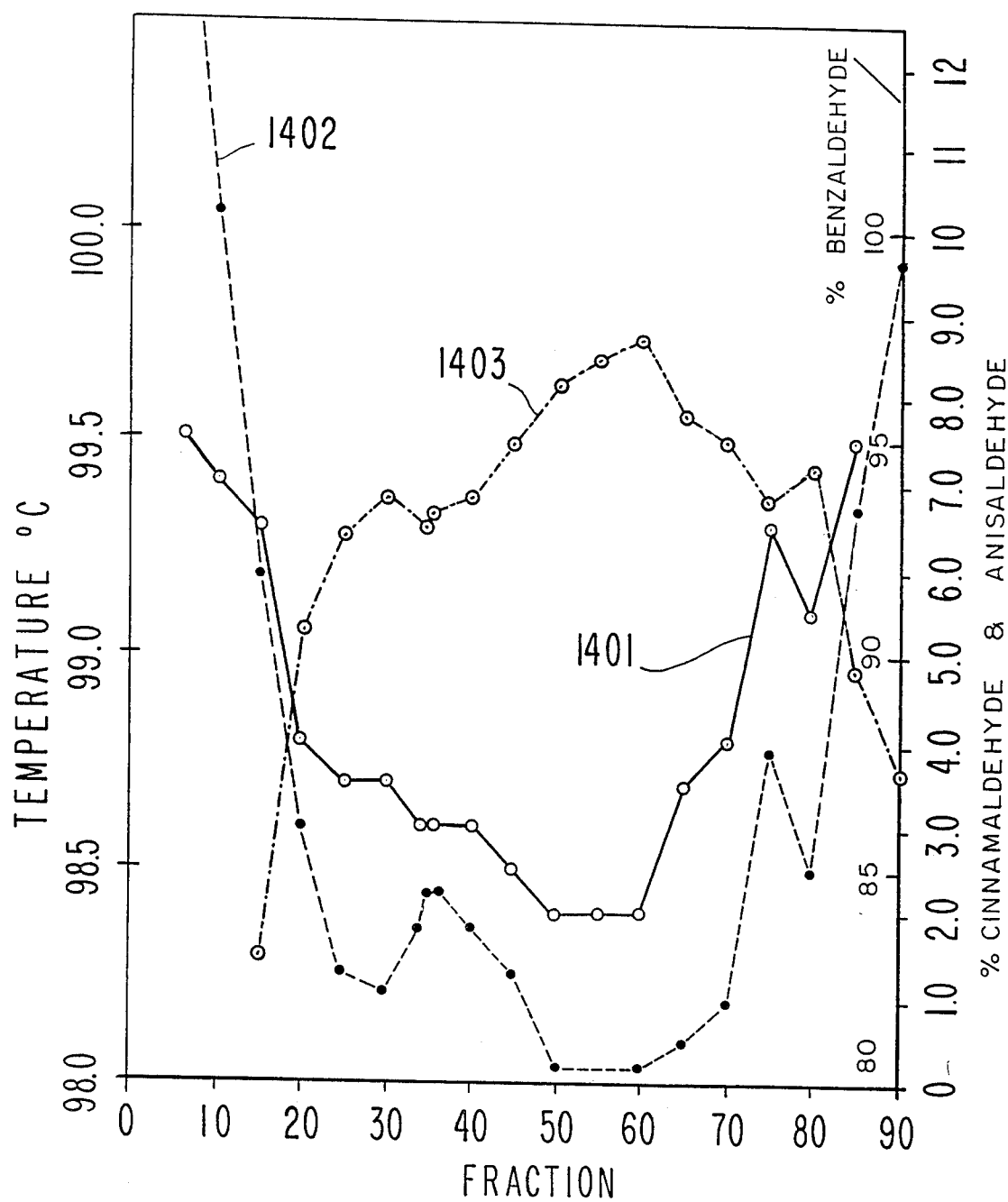

FIG. 14 is a graphic representation of temperature and composition changes during the carrying out of a fractional steam distillation operation on the reaction product of Example XXIV.

Figure 15:
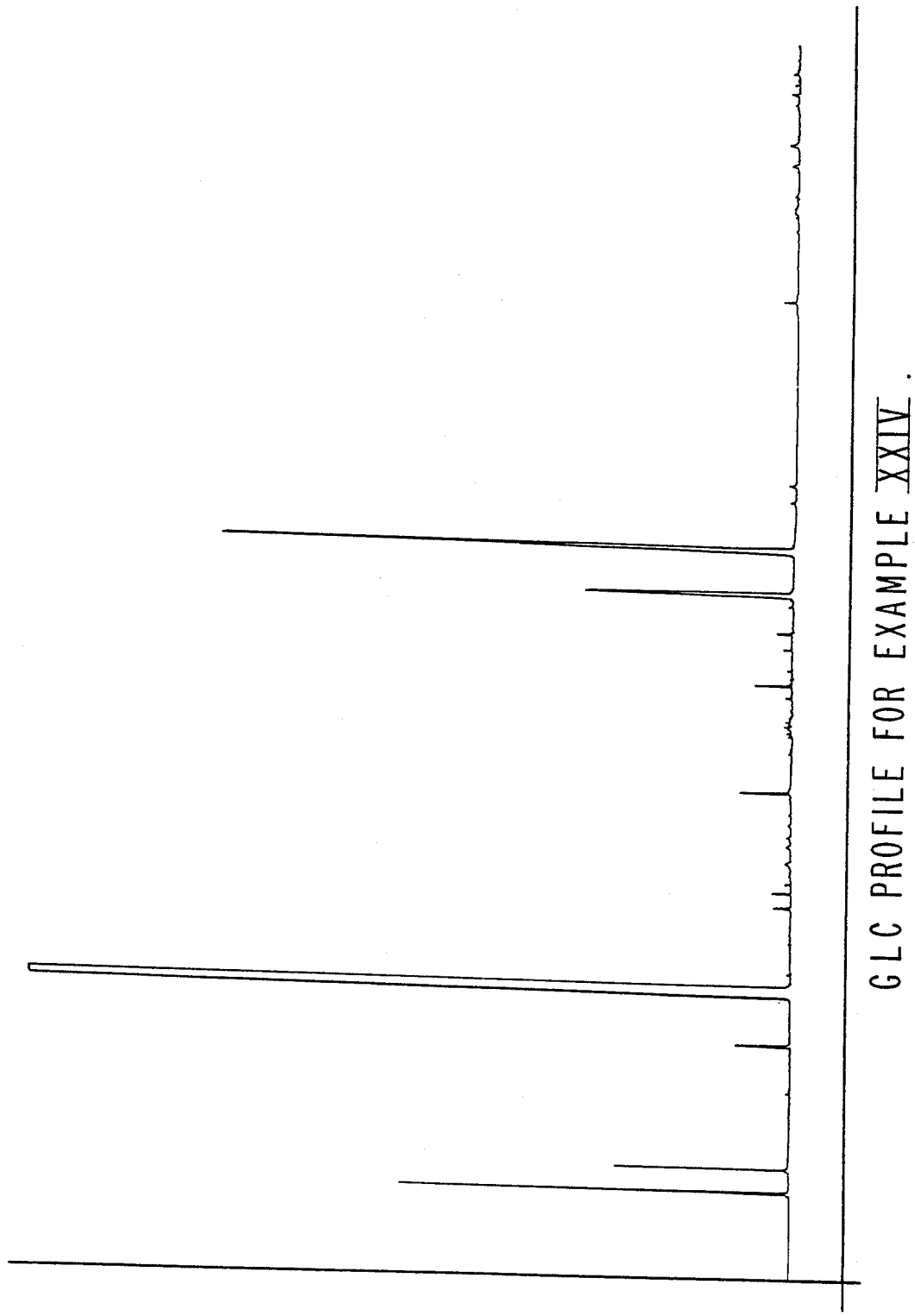

FIG. 15 is the GLC profile for the bulked first distillation product of the reaction product of Example XXIV immediately prior to redistillation (Conditions: Fused silica/methyl silicone column).

Figure 16:
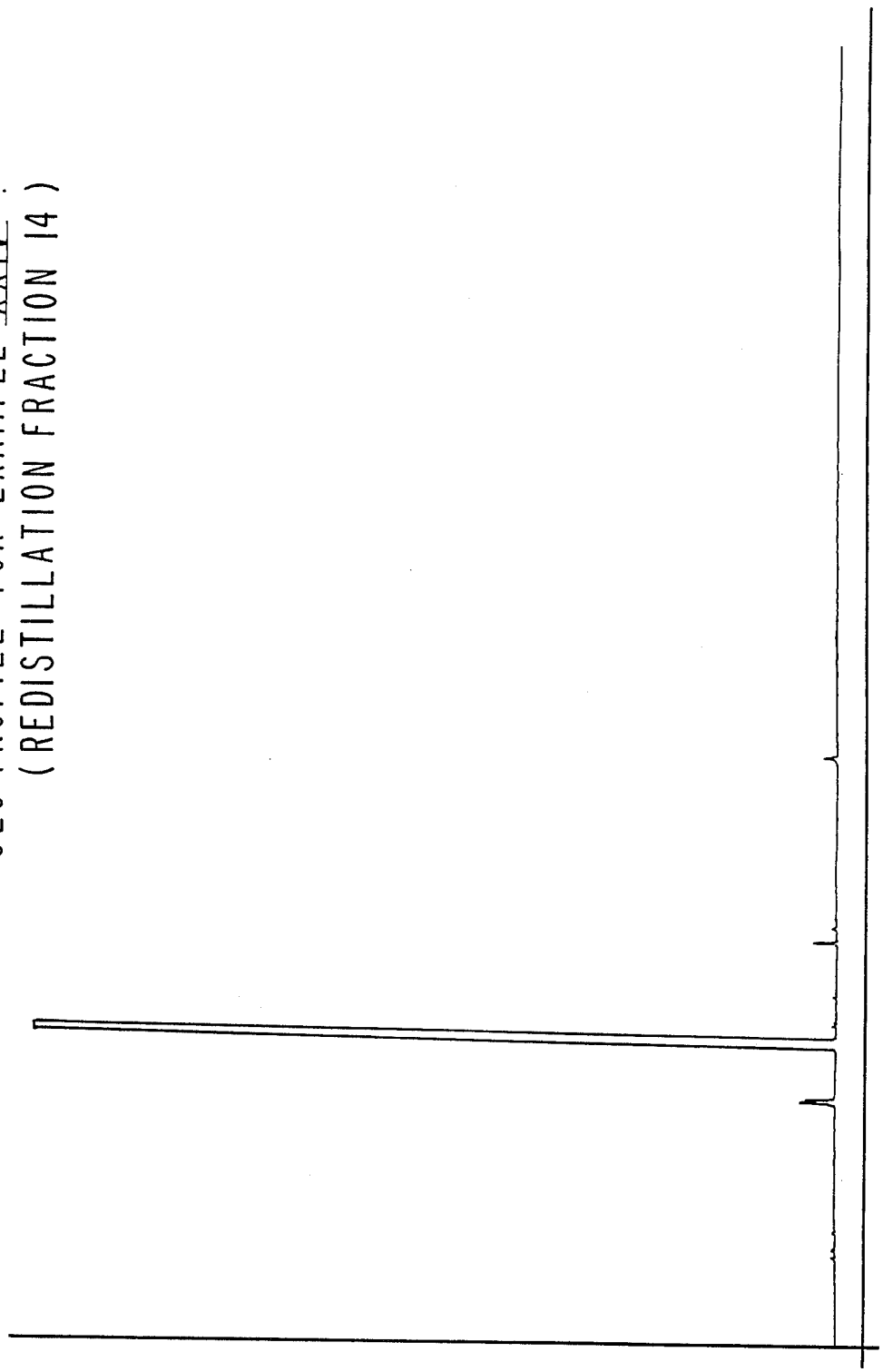

FIG. 16 is the GLC profile for redistillation Fraction 14 of the redistillation (second distillation) of the reaction product of Example XXIV (Conditions: Fused silica/methyl silicone column).

Figure 17:
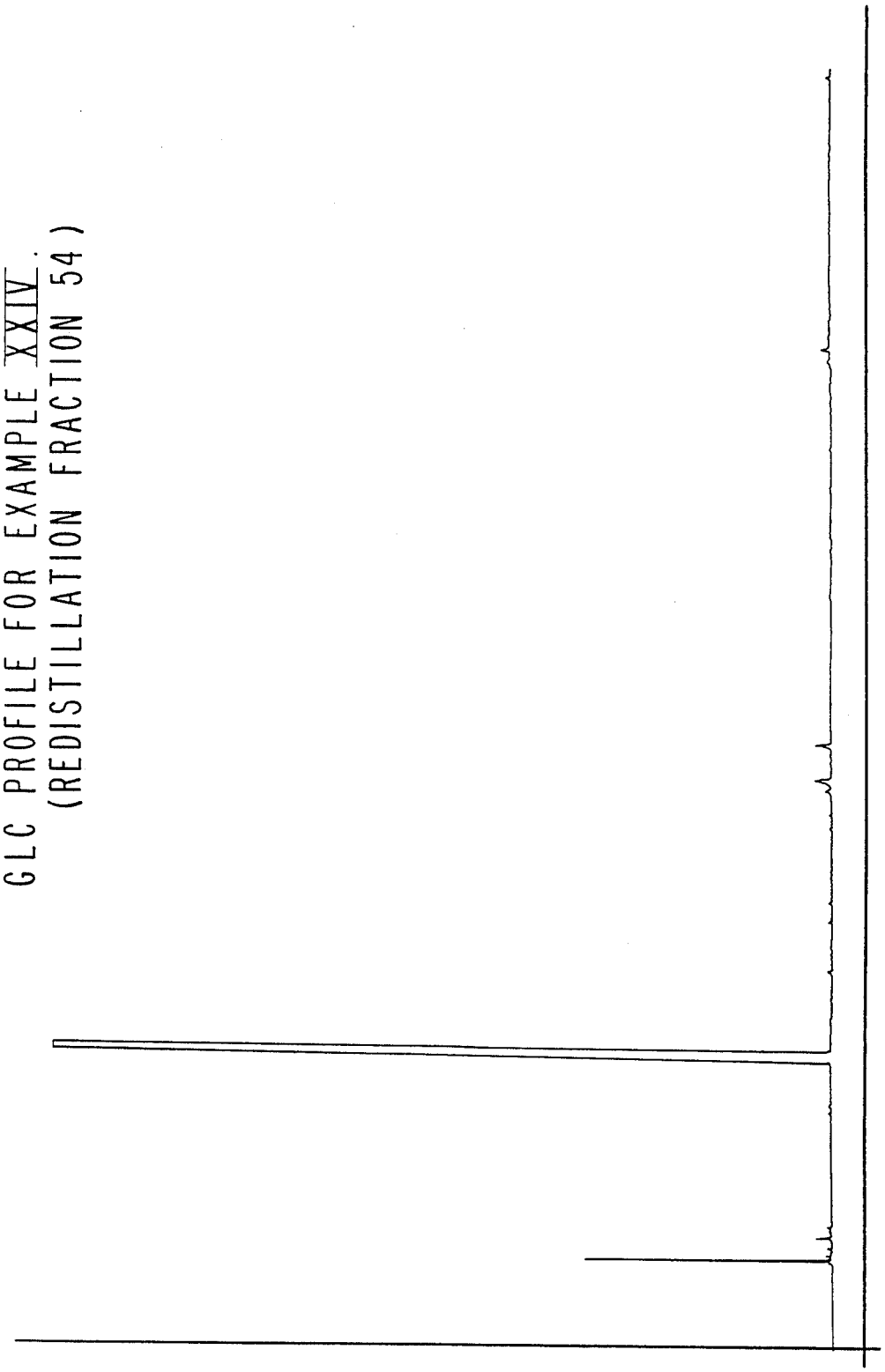

FIG. 17 is the GLC profile for redistillation Fraction 54 of the redistillation of the reaction product of Example XXIV (Conditions: Fused silica/methyl silicone column).

Figure 18:
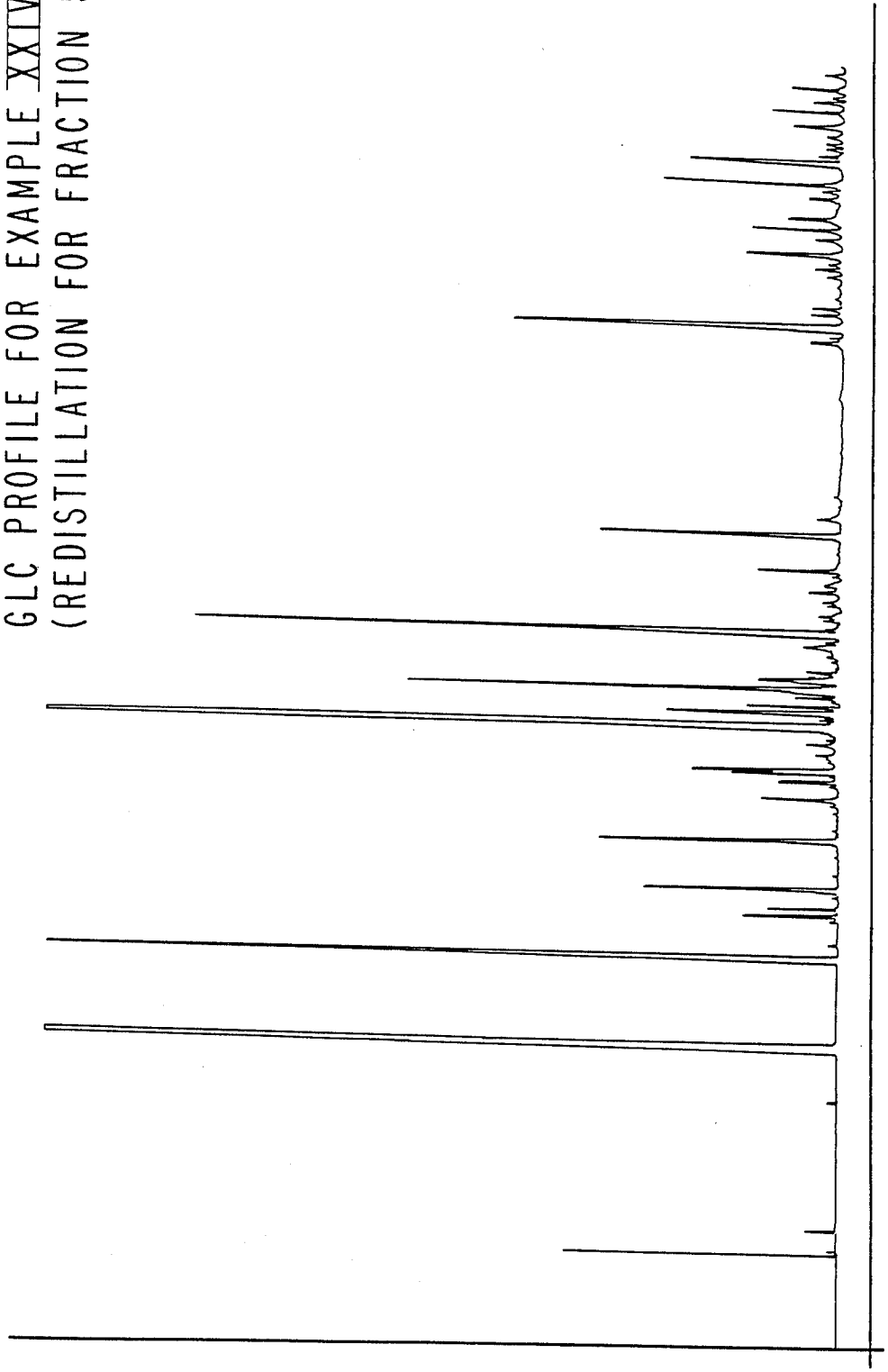

FIG. 18 is the GLC profile for redistillation Fraction 58 of the redistillation of the reaction product of Example XXIV (Conditions: Fused silica/methyl silicone column).

Figure 19:
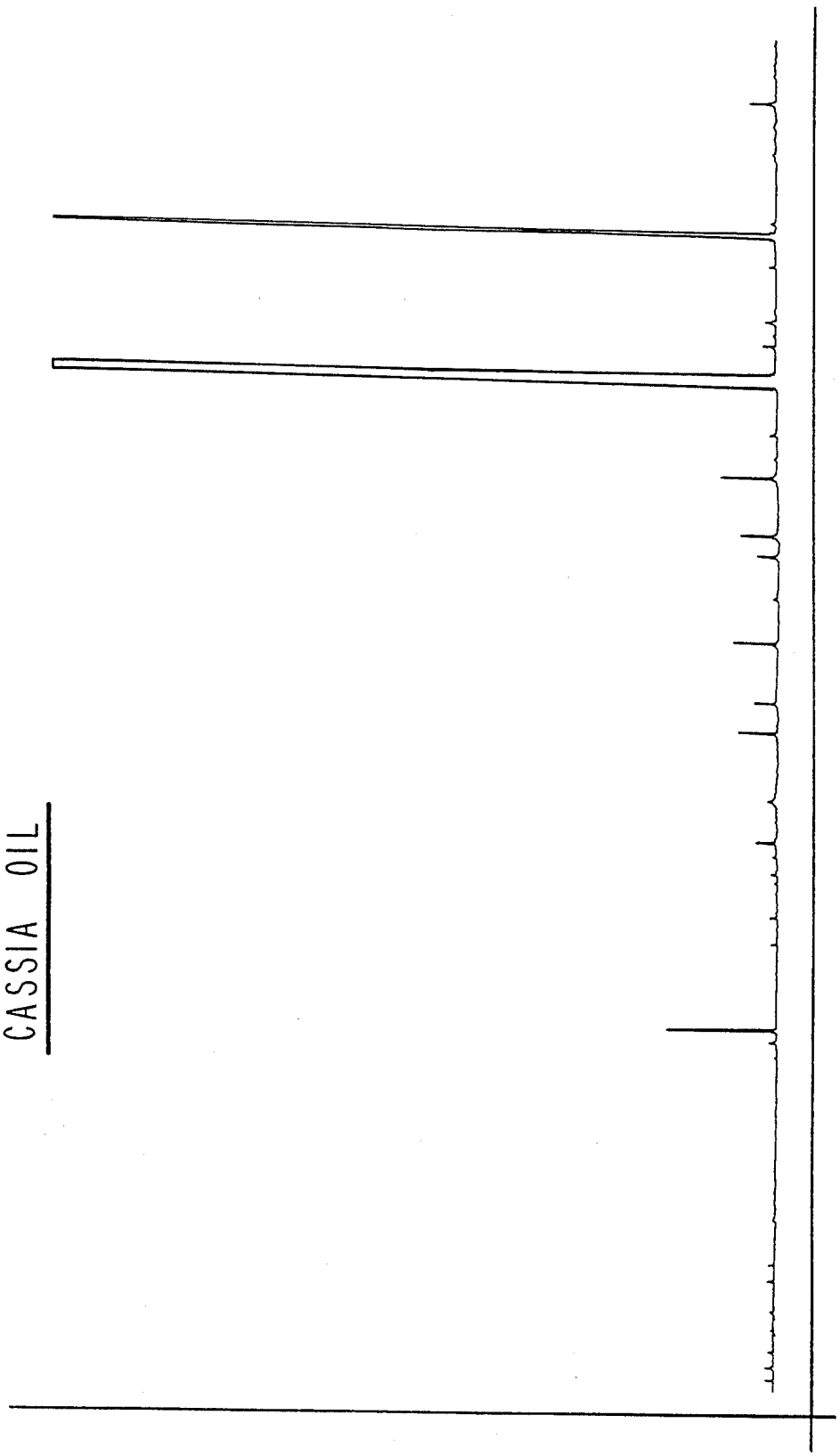

FIG. 19 is the GLC profile for the cassia oil used in Example XXIV (Conditions: Fused silica/carbowax 20M column).

Figure 20:
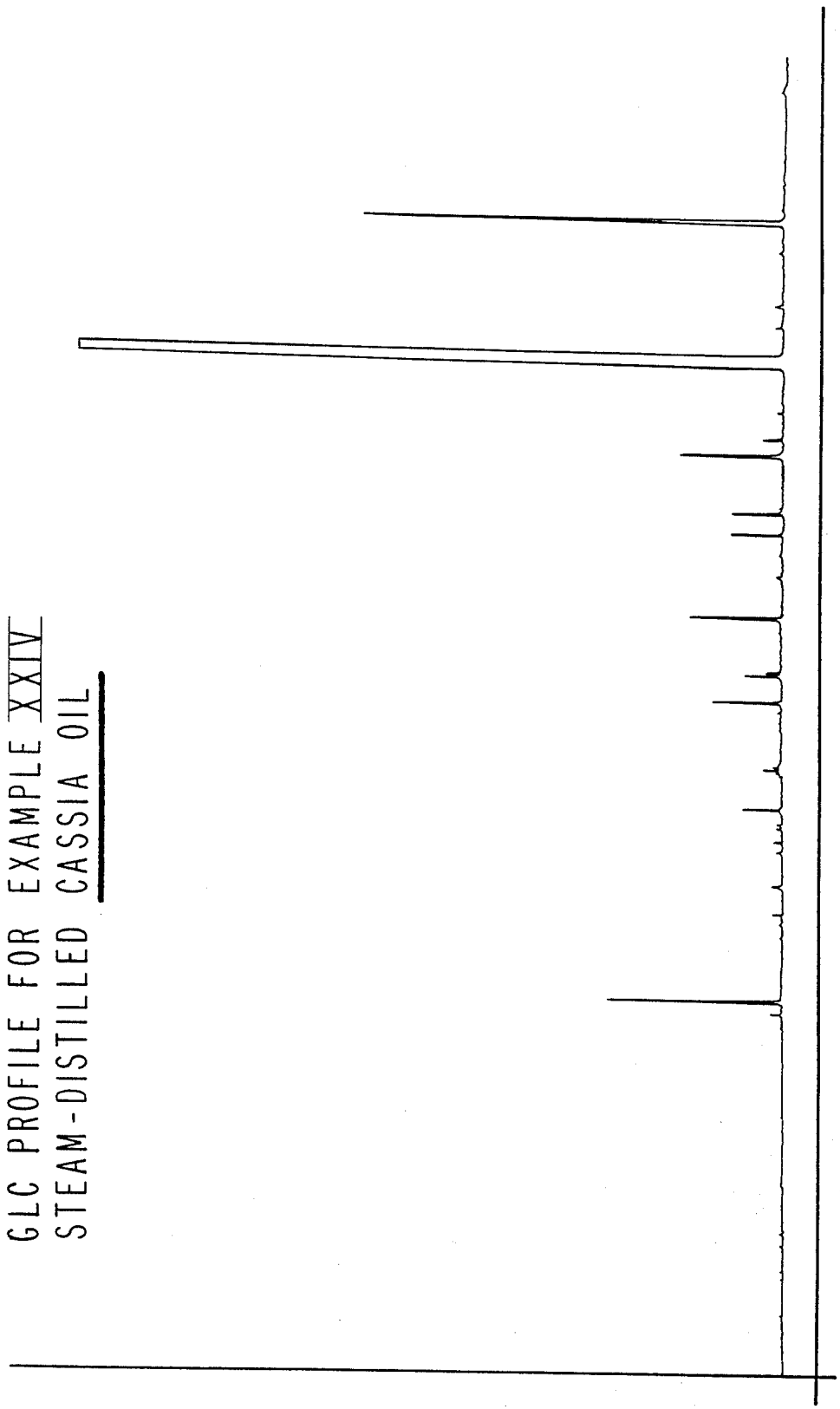

FIG. 20 is the GLC profile for the steam distilled cassia oil used in the reaction of Example XXIV (Conditions: Fused silica/carbowax 20M column, 10 meters×0.32 mm).

Figure 21:
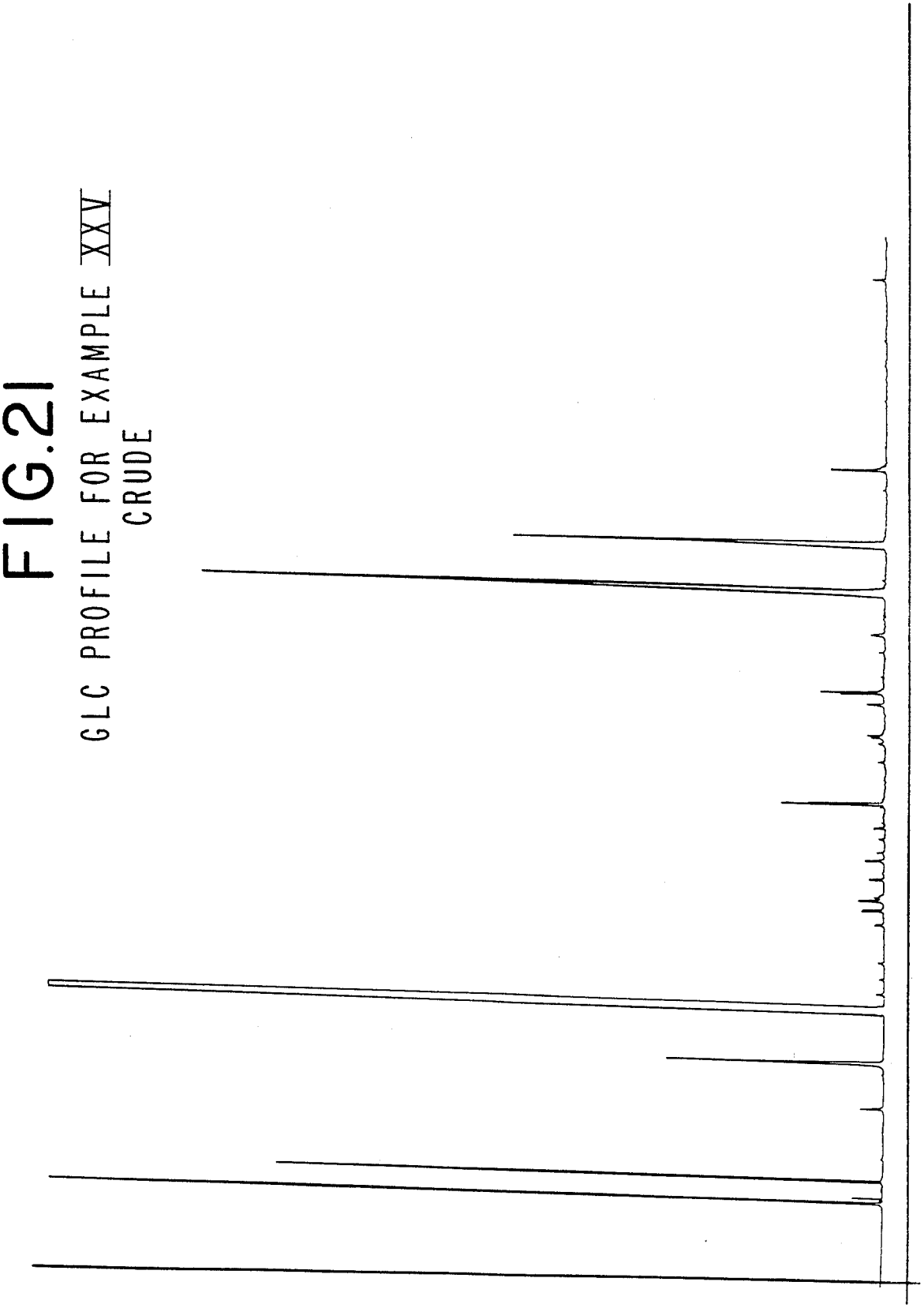

FIG. 21 is the GLC profile for the crude reaction product of Example XXV (Conditions: Fused silica/methyl silicone column).

Figure 22:
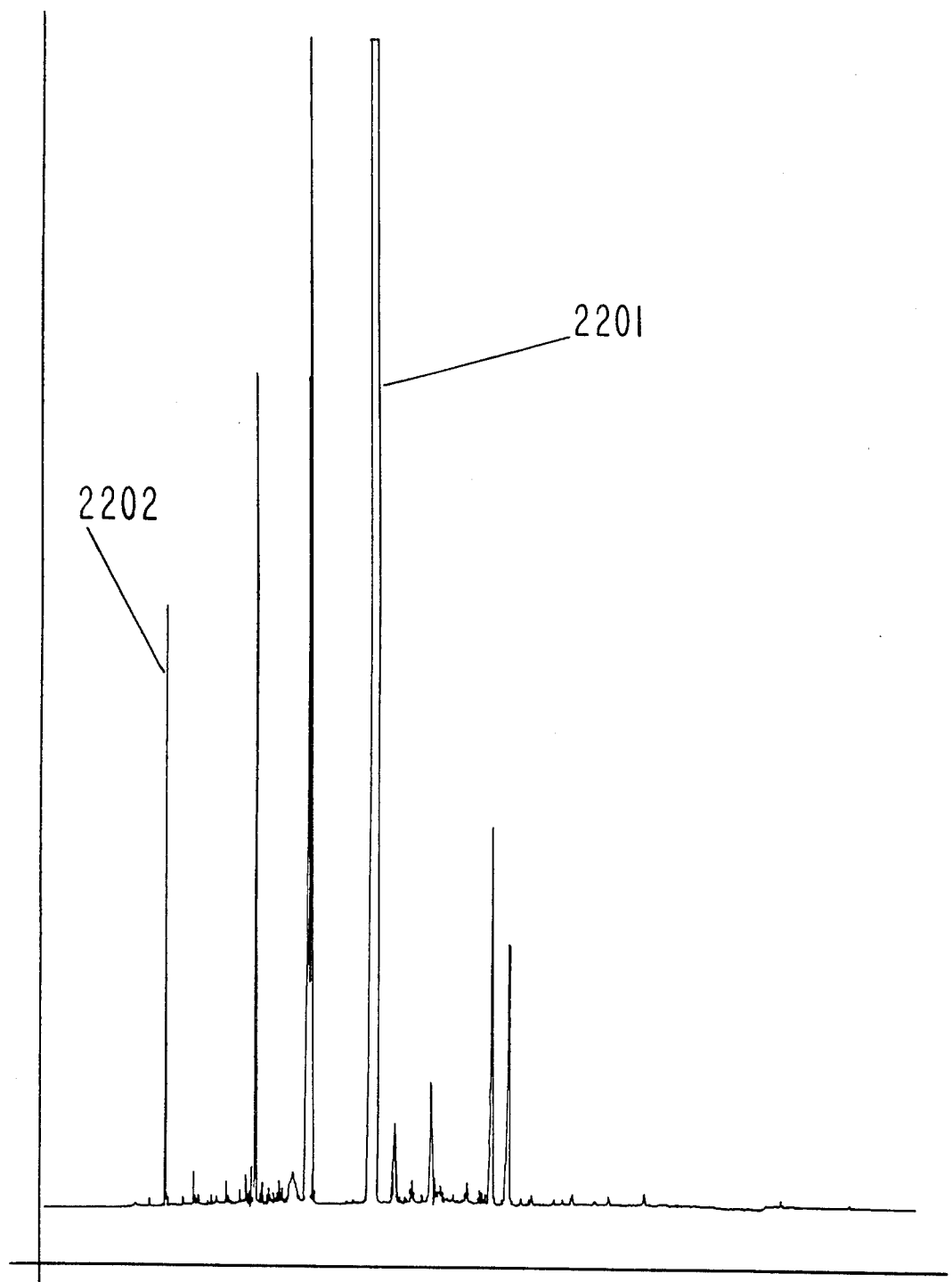

FIG. 22 is the GLC profile for the vacuum distillation product, Fraction 1 of the reaction product of Example XXV (Conditions: 58 meters×0.31 mm OV-1, fused silica/methyl silicone column).

Figure 23:
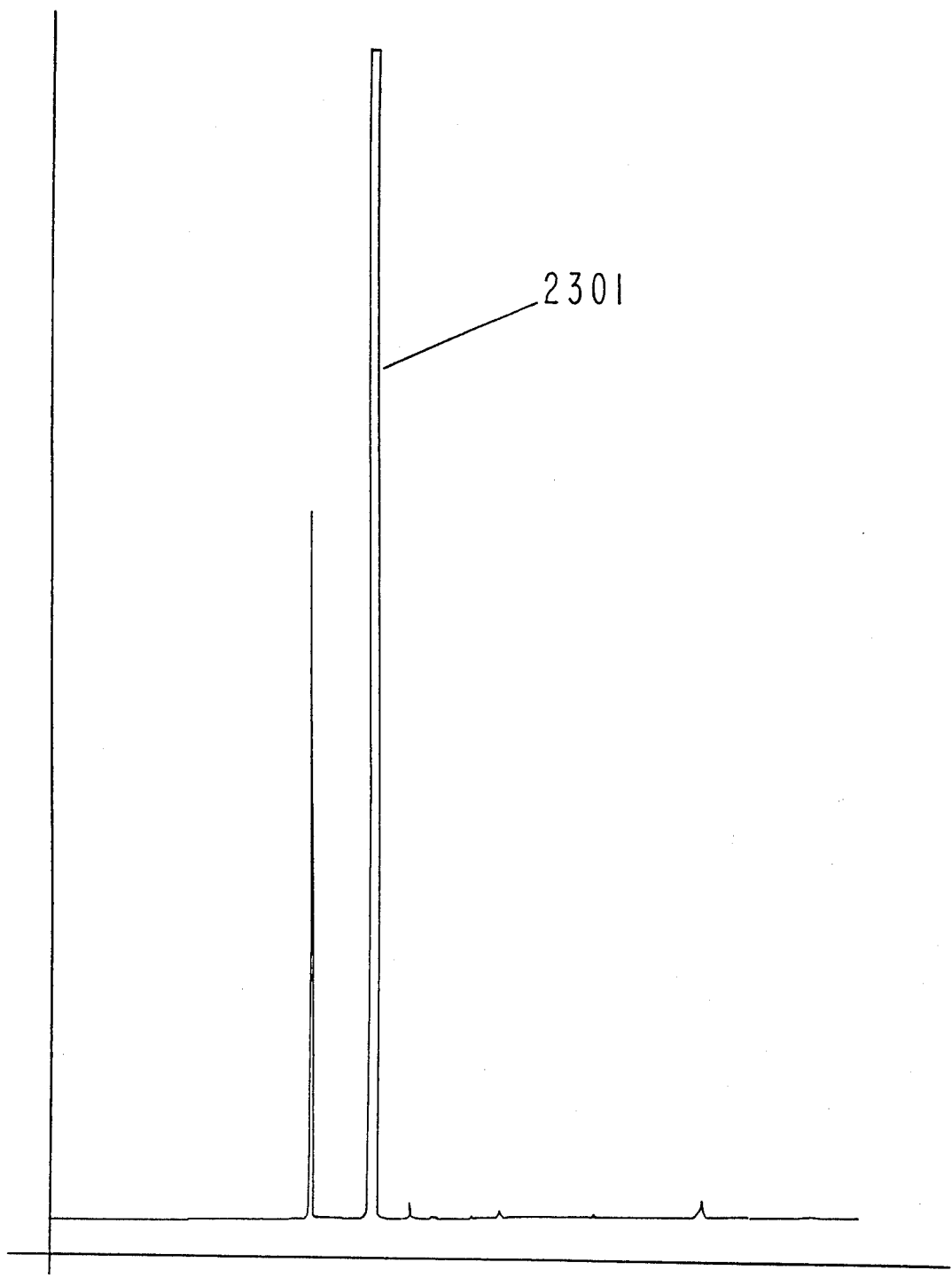

FIG. 23 is the GLC profile for vacuum distillation Fraction 9 of the reaction product of Example XXV (Conditions: 50 meters×0.31 mm OV-1, fused silica column progammed at 75°–225° C. at 2.0° C. per minute).

Figure 24:
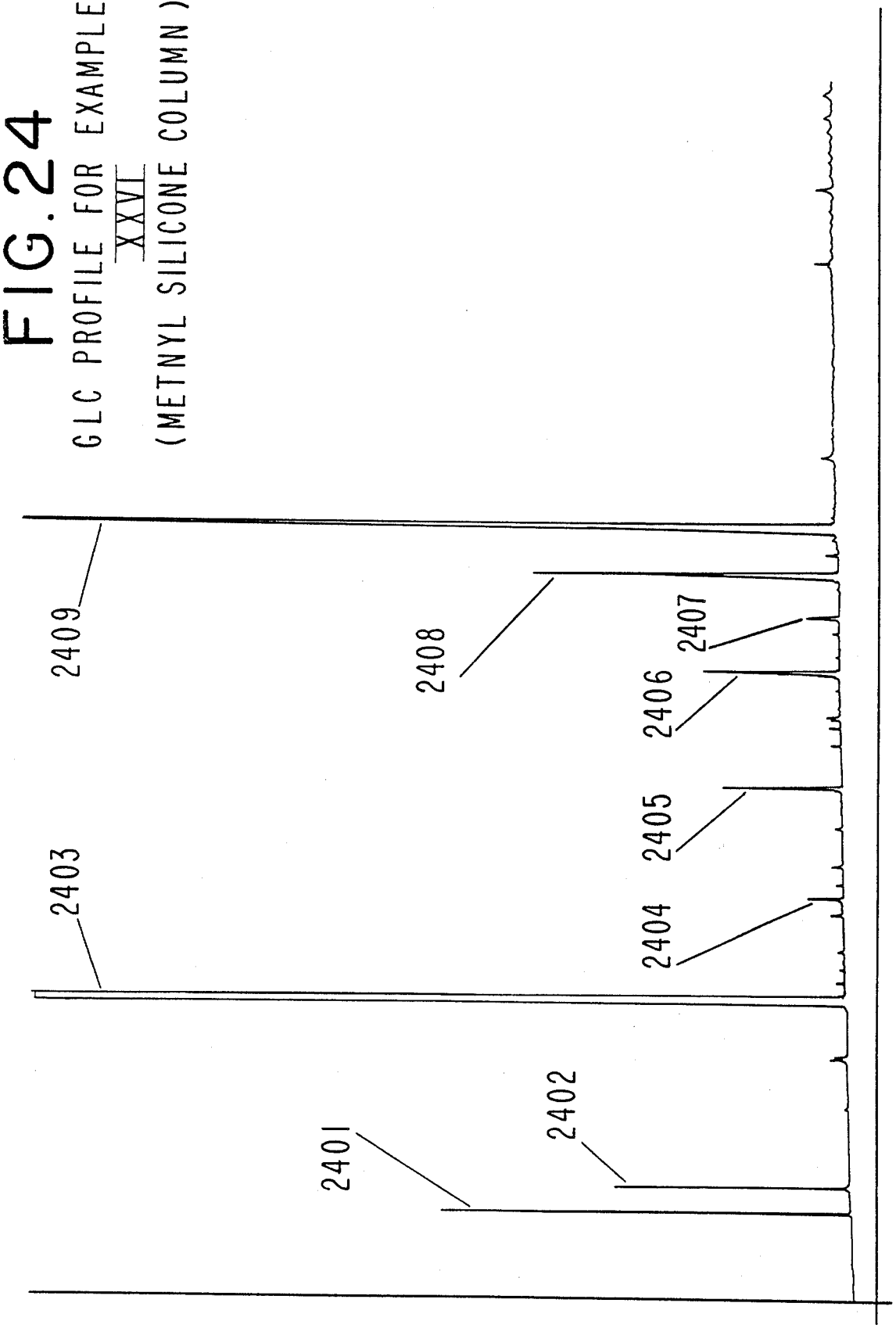

FIG. 24 is the GLC profile for the crude reaction product used in Example XXVI (Conditions: 50 meters×0.32 mm fused silica/methyl silicone column programmed at 75°–225° C. at 2.0° C. per minute).

Figure 25:
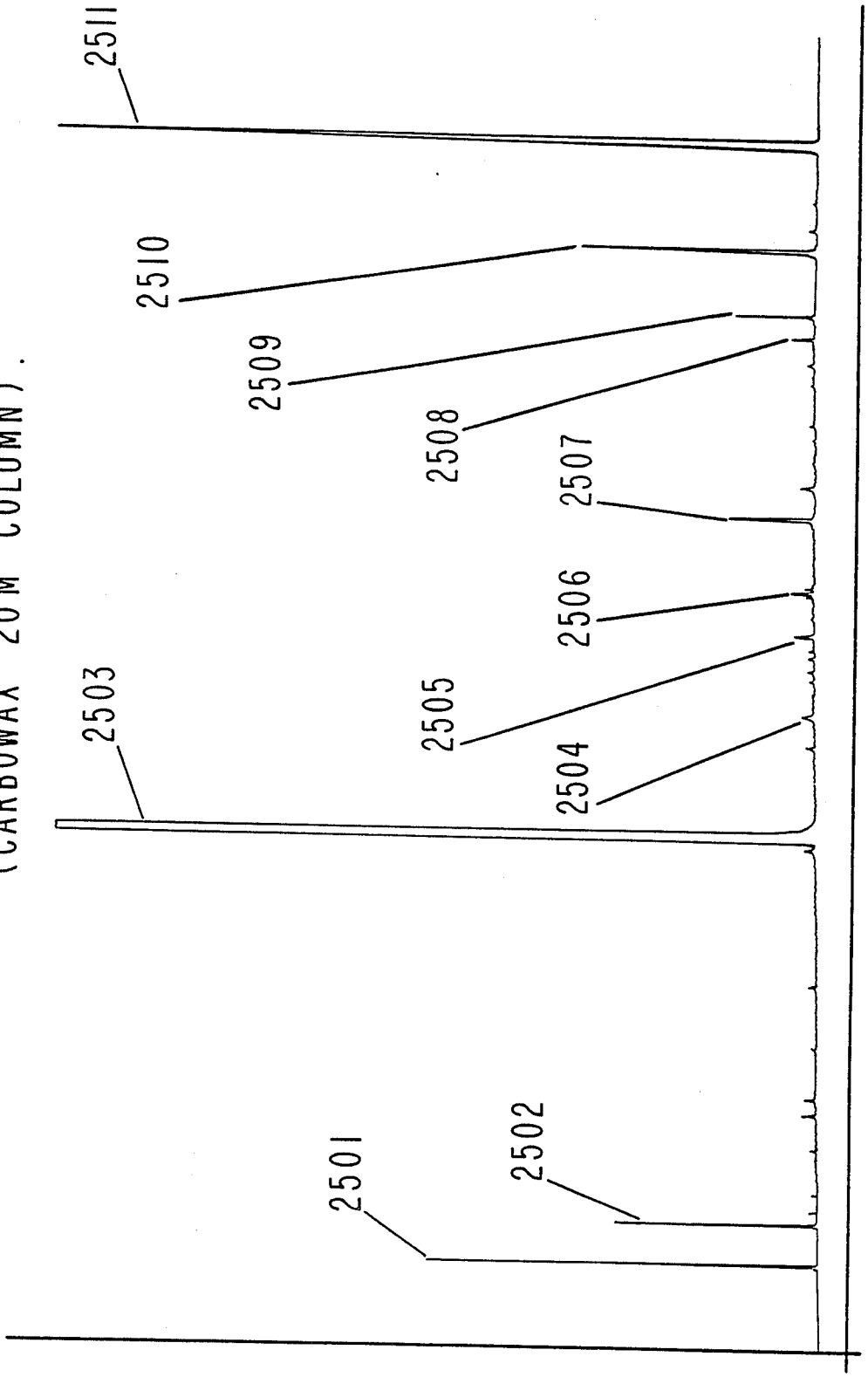

FIG. 25 is the GLC profile for the crude reaction product used in Example XXVI (Conditions: 50 meters×0.32 mm fused silica/carbowax 20M column programmed at 75°–225° C. at 2.0° C. per minute).

Figure 26:
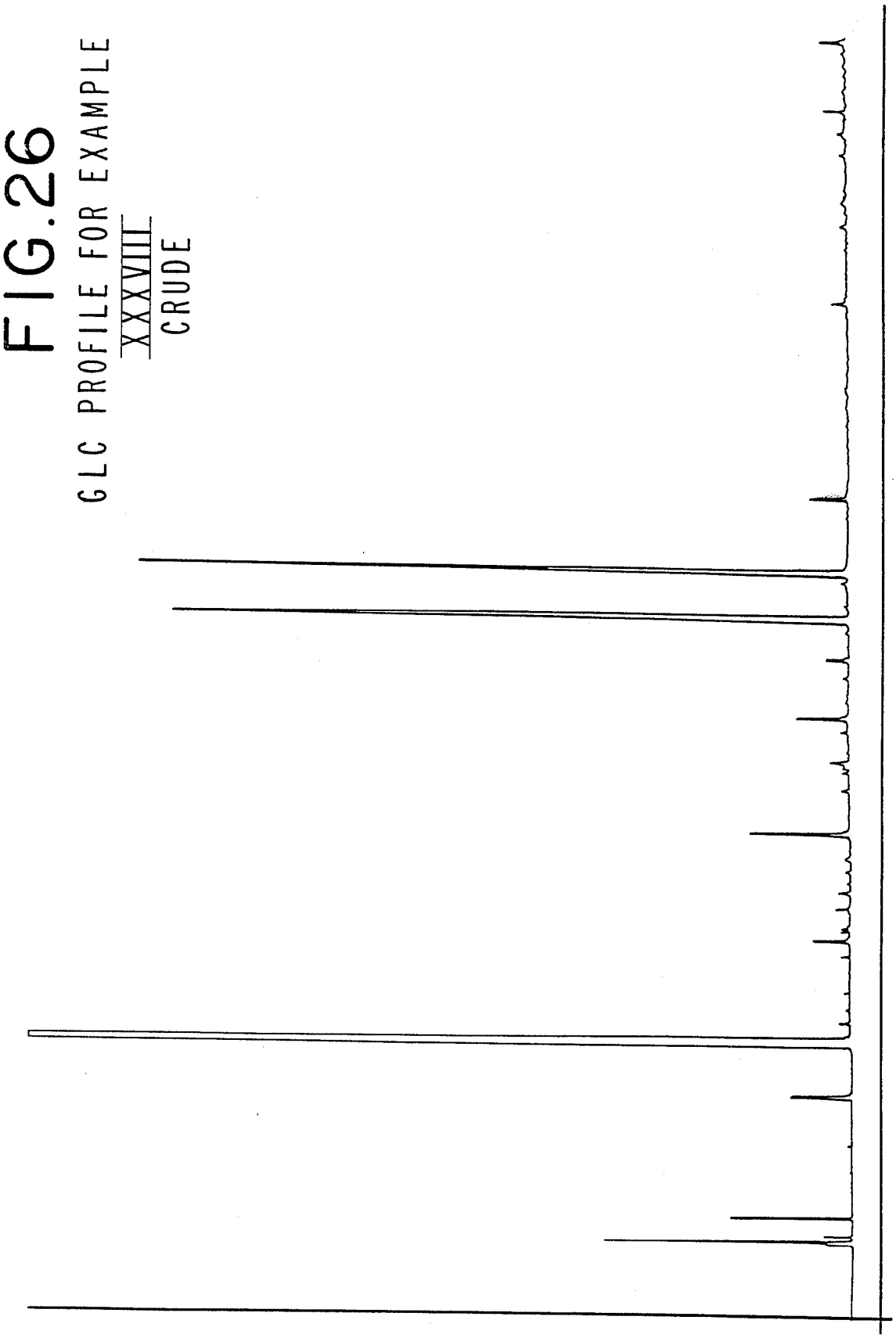

FIG. 26 is the GLC profile for the crude reaction product of Example XXXVIII (Conditions: 50 m×0.322 mm fused silica/methyl silicone column programmed at 75°–225° C. at 2.0° C. per minute).

Figure 27:
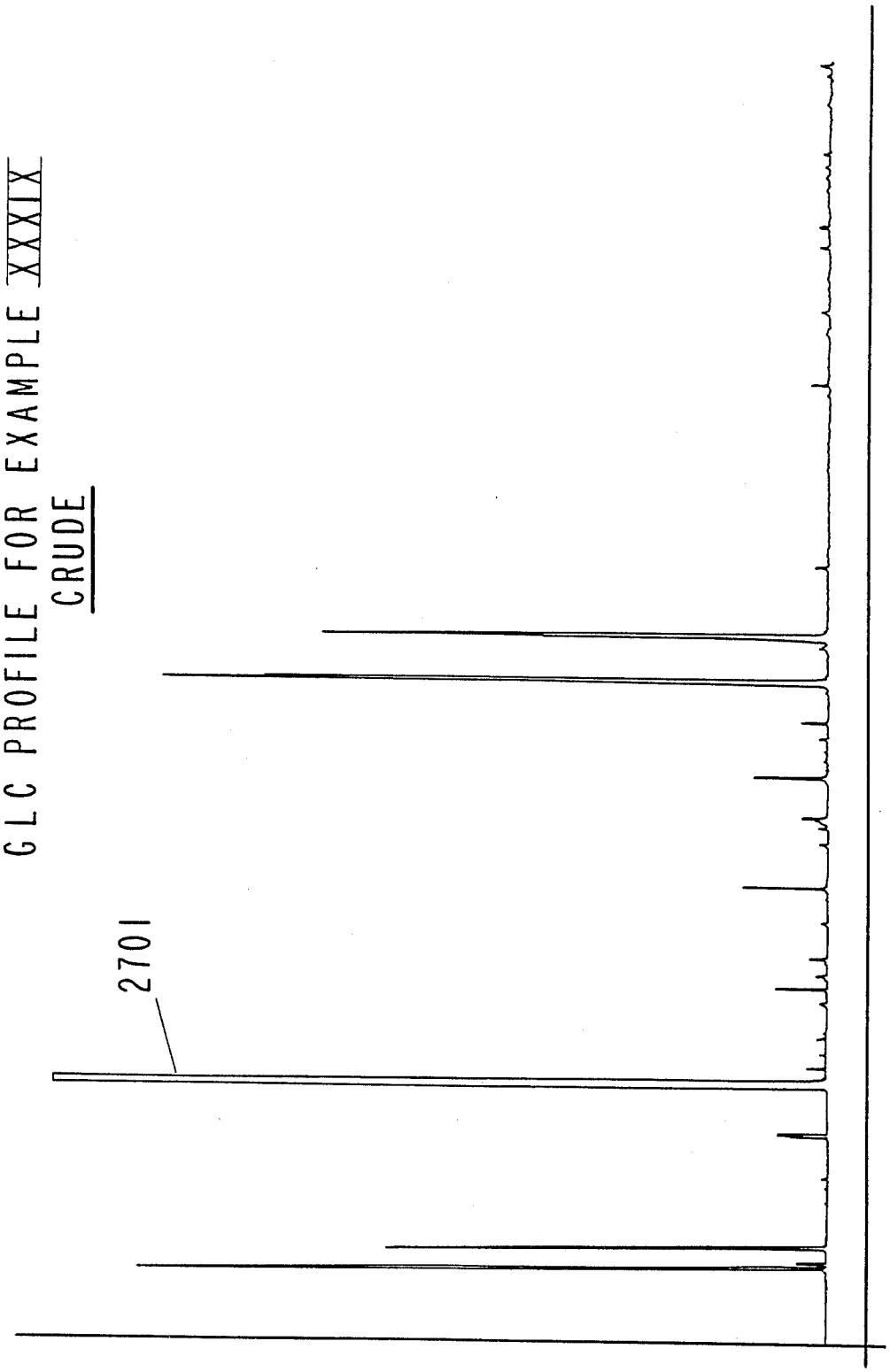

FIG. 27 is the GLC profile for the crude reaction product of Example XXXIX (Conditions: 50 m×0.32 mm fused silica/methyl silicone column programmed at 75°–225° C. at 2.0° C. per minute).

FIG. 28 is the GLC profile for bulked fractions 1–17 from the reaction product of Example XL (Conditions: 50 m×0.32 mm fused silica/methyl silicone column programmed at 75° C.–225° C. at 2.0° per minute).

DETAILED DESCRIPTION OF THE DRAWINGS

Figure 1:
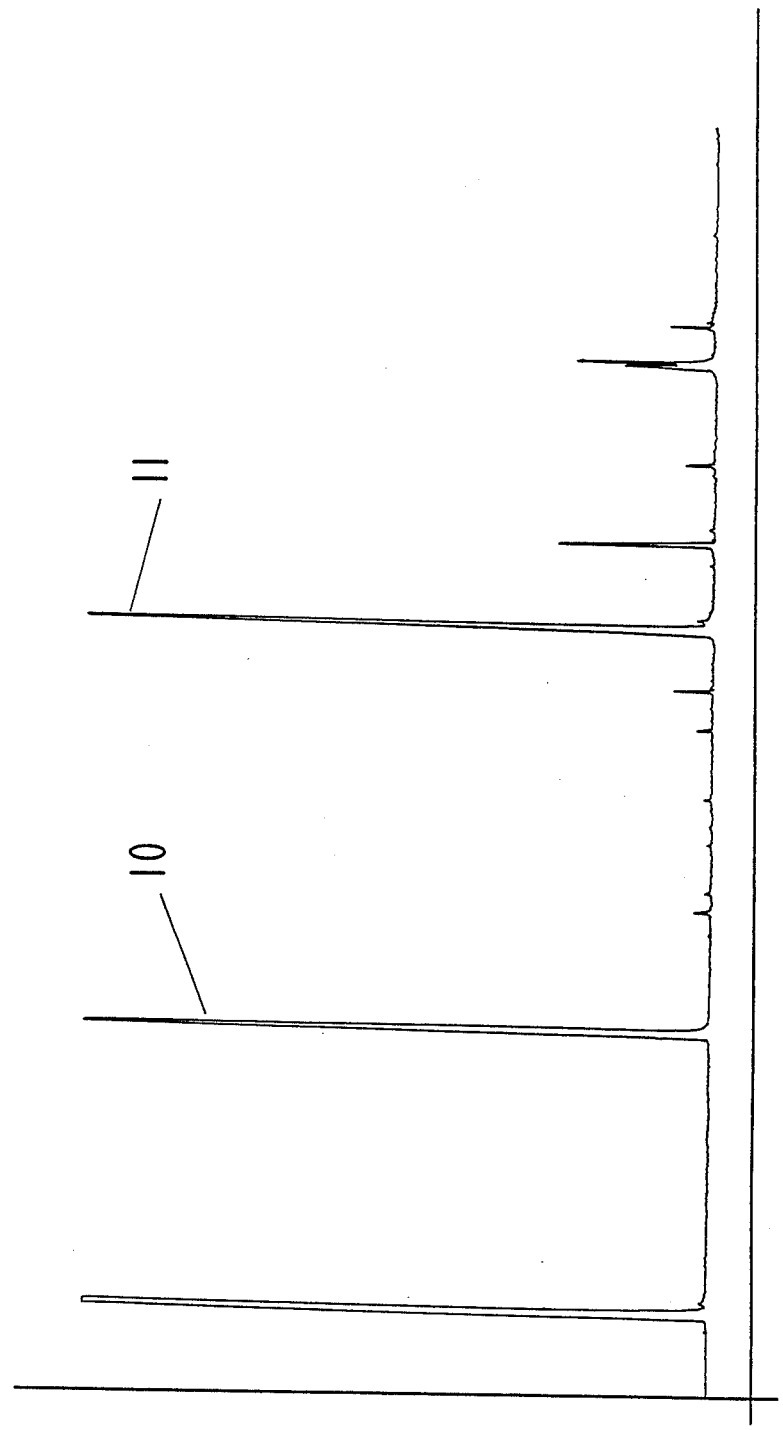
FIG. 1 is the GC-IR spectrum for the reaction product of Example I containing benzaldehyde and cinnamaldehyde.

FIG. 1 is the GC-IR spectrum for the crude reaction product of Example I. The peak indicated by reference numeral 10 is the peak for benzaldehyde in the reaction product. The peak indicated by reference numeral 11 is the peak for cinnamaldehyde having the structures:

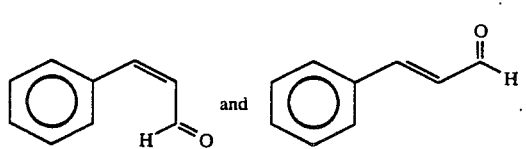

Figure 2:
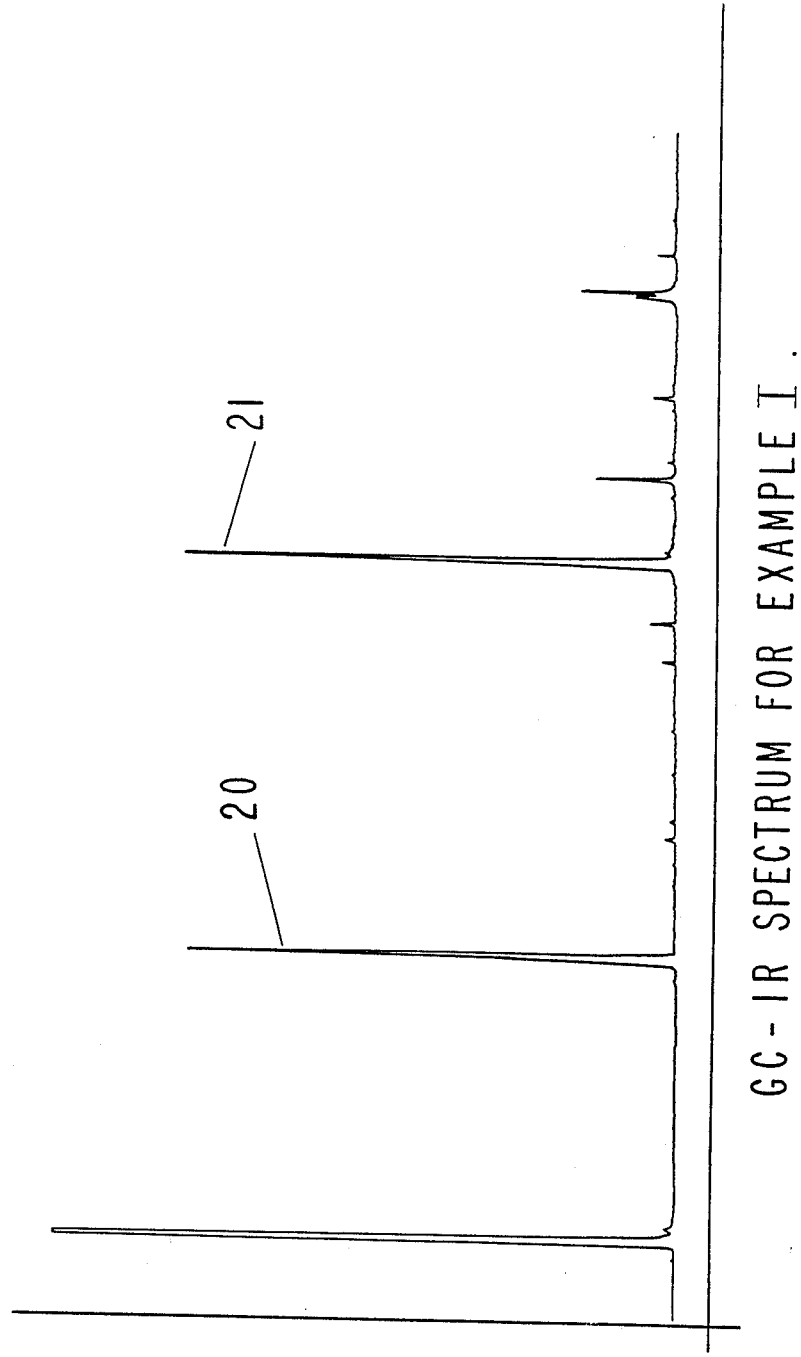
FIG. 2 is a GC-IR spectrum for the distillation residue of Example I containing cinnamaldehyde and benzaldehyde.

FIG. 2 is the GC-IR spectrum for the distillation residue of Example I containing benzaldehyde and cinnamaldehyde. The peak indicated by reference numeral 20 is the peak for benzaldehyde. The peak indicated by reference numeral 21 is the peak for the unreacted cinnamaldehyde having the structure:

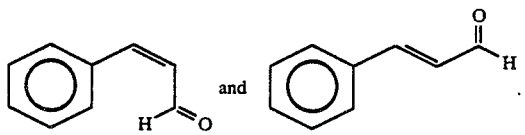

Figure 3:
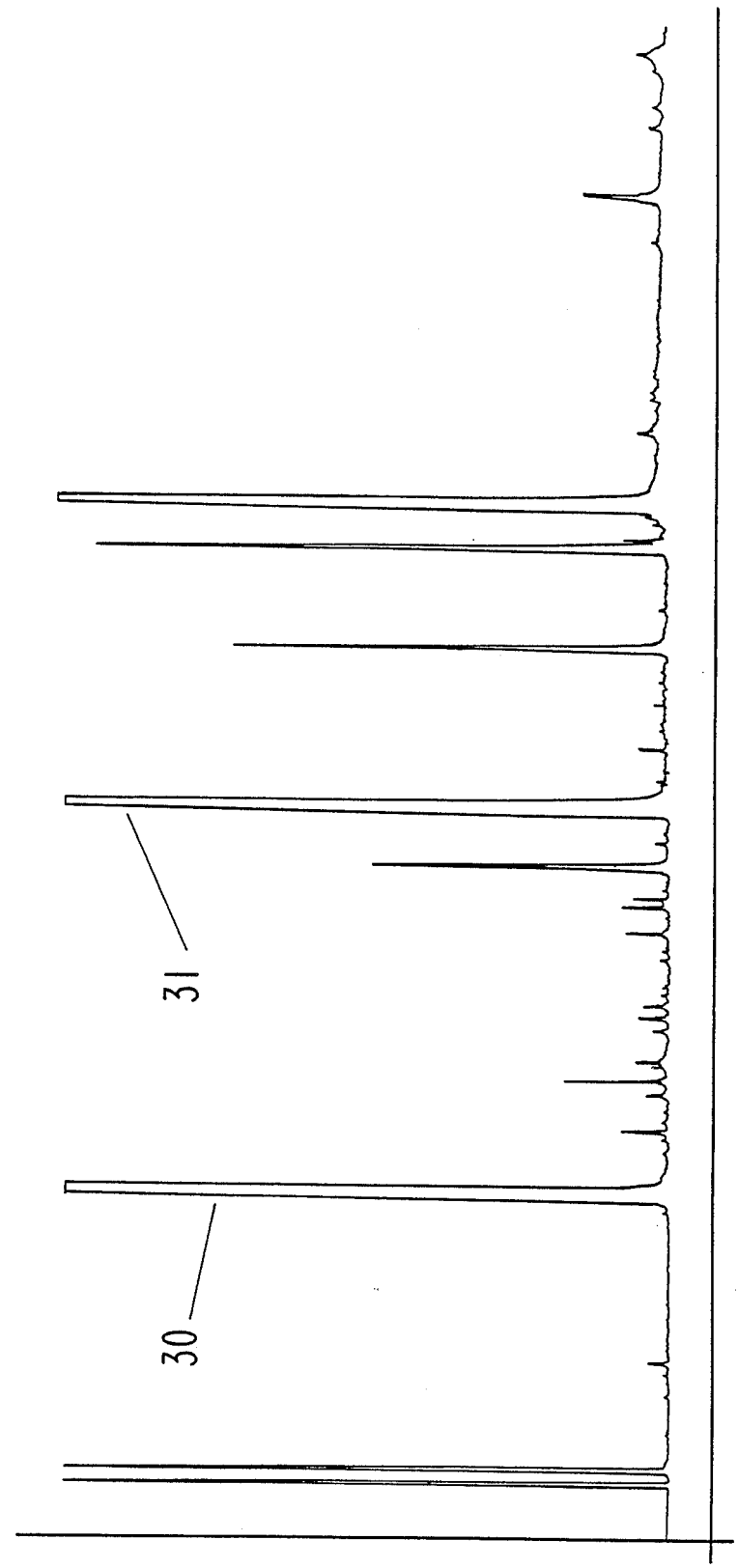
FIG. 3 is a GC-IR spectrum for the reaction product of Example II containing benzaldehyde and cinnamaldehyde (Conditions: Carbowax column programmed at 75°-225° C. at 3 C per minute).

FIG. 3 is the GC-IR spectrum for the crude reaction product of Example II. The peak indicated by reference numeral 30 is the peak for benzaldehyde. The peak indicated by reference numeral 31 is the peak for cinnamaldehyde.

The apparatus of FIG. 4 (the Soxhlet reaction apparatus) is used to effect the reaction:

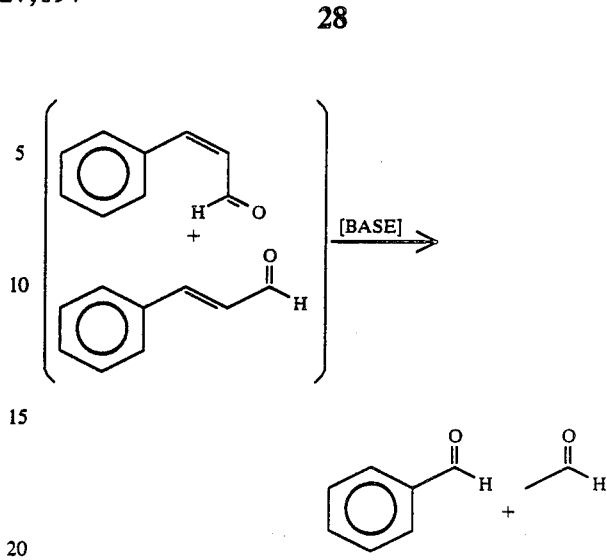

when the cinnamaldehyde is present in such solid materials as pulverized cinnamon bark and/or when using a solid base catalyst, e.g., Ca(OH)$_2$, limestone or Mg(OH)$_2$.

Thus, a mixture of cinnamaldehyde-bearing material (e.g., pulverized cinnamon bark Ceylon) and solid natural base, (for example, limestone Mg(OH)$_2$, Ca(OH)$_2$ or lecithin) 46 is placed in a porous thimble 45. The thus-filled porous thimble is placed in the inner tube 42 of the Soxhlet apparatus 47. The apparatus 47 is then fitted via stopper 48 at opening 50 to a bolt-head flask 41 containing a nonionic emulsifier (preferably a sorbitan derivative emulsifier as defined, supra) and water, or a mixture of at least 50% water and a $C_1$–$C_5$ lower alkanol, e.g., methanol, ethanol, isopropanol, n-propanol, n-butanol, isobutanol, t-butanol, t-amyl alcohol or n-amyl alcohol and to reflux condenser 57 having a cooling jacket 54 fitted with cooling liquid inlet tube 55 surrounding a condenser surface 53. The flask 41 includes a valve 79 and is fitted with steam tube 92 and steam sparger 93 for the purpose of steam distilling the benzaldehyde-containing reaction product from the reaction mass 40 using atmospheric or high pressure steam 94 evolved from steam source 90 through line 91 past valve 95 using, if desired, pump 96. The reflux condenser having outlet 56 is tightly fitted via stopper 52 to the inner tube 42 of the "Soxhlet" apparatus. The solvent, the nonionic emulsifier (preferably sorbitan derivative emulsifier), the water or the water-alkanol mixture is boiled at location 49 in flask 41. The vapor passes up through the tube 44 and is condensed by condenser 57 and the condensed solvent falls from 53 through opening 56 into the thimble 45 and slowly fills the body of the apparatus 47. When the water or the water-$C_1$–$C_5$ lower alkanol mixture contacts the mixture of pulverized cinnamaldehyde bearing material and solid base (e.g., Mg(OH)$_2$) in thimble 45, a retro-aldol reaction is effected, thusly:

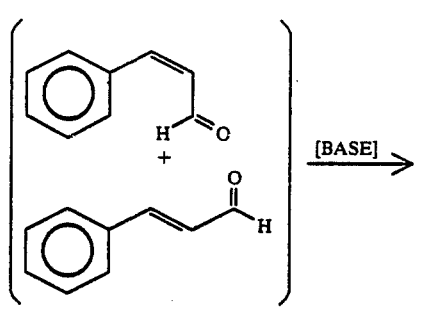

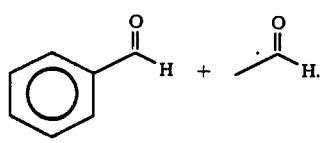

The result of this reaction is the formation of a water-cinnamaldehyde-benzaldehyde-acetaldehyde mixture or a water-cinnamaldehyde-benzaldehyde-acetaldehyde/$C_1$-$C_5$ lower alkanol mixture. The solid-liquid reaction mass residence time in the thimble must be sufficient to allow a final yield of benzaldehyde and acetaldehyde in amounts of 10% or more.

When the mixture reaches the top of tube 43, it siphons over through tube 43 into flask 41 and thus effects removal of that portion of the reaction product which is "extracted" in thimble 45. The process is repeated automatically as the reaction proceeds in thimble 45, that is, the retro-aldol reaction, to wit:

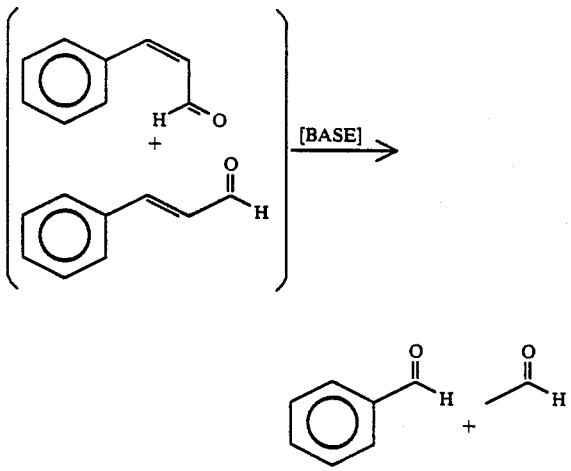

proceeds in thimble 45. The resulting "natural" benzaldehyde may be isolated as by fractional distillation.

In place of the solid base, e.g., Mg(OH)$_2$ at location 46, a lecithin-base mixture (lecithin is a choline precursor having the structure:

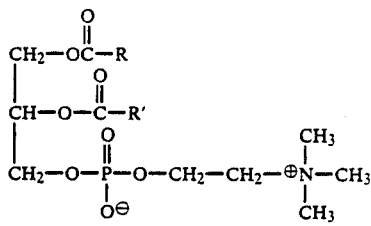

wherein the moieties:

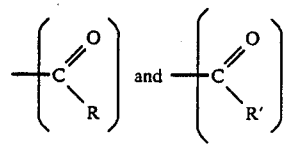

have been defined, supra) may be added at location 40 (with the reaction taking place at location 40 rather than at location 46 or a natural proline or chloline embedded in an inert polymer having a micropores such as microporous polyethylene may be admixed with the cinnamaldehyde-bearing solid, e.g., the pulverized cinnamon bark at location 46.

In the case of the reaction taking place at location 46, the siphon tube 43 has an outlet into the flask 41 at 51 wherein the reaction product containing large amounts of benzaldehyde together with water, or water/alkanol mixture is passed through the opening 51 of siphon tube 43 and then through the tube 49 of the "Soxhlet" apparatus 47 into flask 41.

The Soxhlet apparatus is firmly in place in a vapor-tight manner as a result of the placement of tube 49 in tightly-fitting stopper 48 located in the neck of flask 41 at location 50.

In the case of the reaction taking place at location 40, the siphon tube 43 has an outlet into the flask 41 at 51 wherein extracted cinnamaldehyde together with water or water/alkanol mixuture is passed through the opening 51 of siphon tube 43 and then through the opening of the Soxhlet apparatus into flask 41. The Soxhlet apparatus is firmly in place in a vapor-tight manner as a result of the placement of tube 49 in tightly-fitting stopper 48 located in the neck of flask 41 at location 50.

When the solid at location 46 is initially soley solid base, e.g., Mg(OH)$_2$, limestone or Lecithin, the solid natural base 46 is placed in porous thimble 45. The thus filled porous thimble 45 is placed in the inner tube 42 of the Soxhlet apparatus. The apparatus is then fitted via stopper 48 at opening 50 to a bolt-head flask 41 containing water or a mixture of at least 50% water and a $C_1$-$C_5$ lower alkanol, e.g., methanol, ethanol, isopropanol, n-propanol, n-butanol, isobutanol, t-butanol, t-amyl alcohol or n-amyl alcohol, a nonionic emulsifier (preferably sorbitan derivative emulsifier as defined, supra), and a natural cinnamaldehyde-containing oil, e.g., cinnamon leaf oil or cassia oil and to reflux condenser 57 having a cooling jacket 54 fitted with cooling liquid inlet tube 55 surrounding a condenser surface 53. The flask 41 includes a valve 79 and is fitted with a steam tube 92 and steam sparger 93 for the purpose of steam distilling the benzaldehyde-containing reaction product from the reaction mass 40 using atmospheric or high pressure steam 94 evolved from steam source 90 through line 91 past valve 95 using, if desired, pump 96.

Valve 79 is a safety valve. The reflux condenser having outlet 56 is tightly fitted via stopper 52 to the inert tube 42 of the Soxhlet apparatus. The solvent, the nonionic emulsifier (preferably a sorbitan derivative emulsifier), the cinnamaldehyde-containing oil, and the water or the water-alkanol mixture is boiled at location 40 in flask 41. The vapor passes up through the tube 44 and is condensed by condenser 57 and the condensed solvent falls from 53 through opening 56 into the thimble 45 and slowly fills the body of the apparatus 47. When the water or the water/$C_1$-$C_5$ lower alkanol mixture contacts the solid base (e.g., Mg(OH)$_2$ or limestone or Ca(OH)$_2$) in thimble 45, the OH$^-$ ions are transported into flask 41 and into the reaction mass at location 40 in flask 41 thereby causing the "retrol-aldol" reaction to be effected thusly:

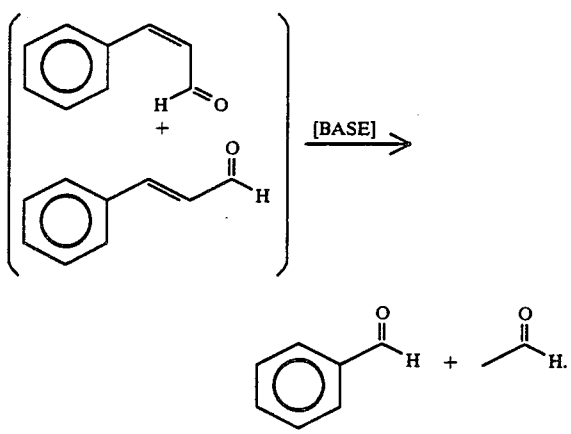

At the desired time for recovery of the resulting reaction product located at location 40 valve 96 is adjusted for product recovery. Thus, valve 74 is converted from a "closed" position to a "open" position in line 97 and steam from source 90 through line 91 past valve 95 using pump 95a through opening 77 using line 92 through sparger 93 is passed into the benzaldehyde-containing reaction product in flask 41 at location 40. The steam (shown by bubbles 94) carries or entrains benzaldehyde-rich vapors through line 44 past valve 96 through line 97 past valve 74 into condenser 98 which is cooled with cooling water entering or leaving from opening 99 using jacket 78. The resulting product which may contain a high proportion (e.g., 40%) of unreacted cinnamaldehyde may be replaced at location 40 in flask 41 with nonionic sorbitan derivative containing emulsifier and additional water soluable base, e.g., sodium bicarbonate to be redistilled using steam from source 90, the redistillation taking place using condenser 98 and cooling jacket 78.

In place of Soxhlet apparatus 47 and tube 42, the retro-aldol reaction can take place in an apparatus of the nature of FIG. 5.

Referring now to FIG. 5, solid cinnamaldehyde-containing material, for example, pulverized cinnamon bark may be placed on a sintered glass disc 70 of FIG. 5 and the entire apparatus may be fitted onto a reaction vessel which is also fitted with a distillation apparatus. Hot alkanol-water/non-ionic emulsifier (preferably sorbitan derivative emulsifier) mixture or hot water/nonionic emulsifer (preferably sorbitan derivative emulsifier) mixture may be added through opening 73 into tube 71 slowly past the pulverized cinnamaldehyde-containing material resting on sintered glass disc 70. The water-/emulsifier or the water/$C_1$-$C_5$ lower alkanol/emulsifier mixture may be admixed with a base such as proline, choline sodium bicarbonate, potassium bicarbonate, sodium carbonate, sodium bicarbonate, lithium carbonate, lithium bicarbonate or a mixture of lecithin and base. In the alternative, the cinnamaldehyde-yielding material may be admixed with solid base (e.g., Mg(OH)$_2$ limestone or Ca(OH)$_2$) while resting on sintered glass disc 70. The entire apparatus is fitted at 72 into a flask having fitted thereto a distillation apparatus. As the benzaldehyde-rich and acetaldehyde rich reaction mixture passes through disc 70 through opening 74 into the flask it may be simultaneously fractionally steam distilled or it may be recycled if it contains an excessive amount of cinnamaldehyde that has not reacted and if it is desired to create a more enriched benzaldehyde-containing product.

FIG. 6 is a schematic diagram of a solid-liquid phase reaction apparatus which can be used to carry out the retro-aldol reaction of our invention, to wit:

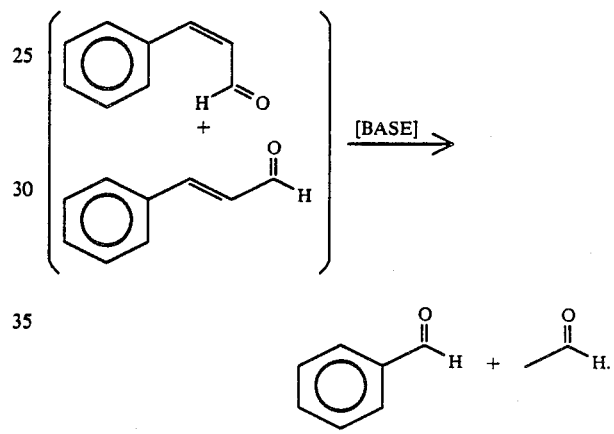

Set forth in FIG. 6 is a solid-liquid retro-aldol reaction apparatus which is specifically described in U.S. Pat. No. 1,636,550, the specification for which is incorporated herein by reference. Specifically, in FIG. 6, the numeral 2001 designates a holder for particularized cinnamaldehyde-bearing solid, for example, particularized cinnamon bark or cinnamon leaf which contains a large quantity of cinnamaldehyde having the structures:

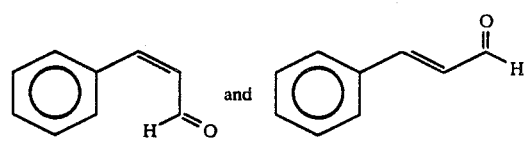

and/or a solid basic catalyst (e.g., Ca(OH)$_2$, limestone or Mg(OH)$_2$) which is shown at 2002 in the drawing. Arranged below the holder in vaporizing apparatus for natural cinnamaldehyde-containing oil (e.g., cassia oil), nonionic emulsifier (preferably sorbitan derivative emulsifier), and reaction solvent, e.g., water or a mixture of $C_1$-$C_5$ lower alkanol and water (such as a 50:50 mixture of ethanol and water), which apparatus consists preferably of a closed container 2003 arranged in a heating bath vessel 2004 which may be a hot oil bath. Heat may be applied to vessel 2004 either by gas flame, steam coils located in the vessel, solar energy or any other suitable means.

Atmospheric pressure or high pressure steam 2033 supplied from source 2030 through line 2031 past valve 2038 using pump 2039 may be supplied to the reaction solvent-emulsifier-cinnamaldehyde-containing oil system acting as:
 (i) energy of activation for the reaction;
 (ii) a heat source;
 (iii) agitation means; and/or
 (iv) distillation means (at the desired termination of carrying out the reaction).

Connected with the holder 2001 is a condenser 2005. The condenser 2005 may be of any suitable construction. It is shown as consisting of a vessel provided with two interior headers 2006 and 2007 having a plurality of condensing tubes 2008. The space between the headers is supplied with a cooling fluid by means, for example, of a cold water inlet pipe 2009. 2010 Is an outlet pipe for cooling fluid which fluid may, if desired, be artificially cooled before being introduced into the condenser to the extent necessary to completely condense the vaporized solvent to a temperature of 60°-80° C., for example, although this temperature will necessarily vary with the pressure in the holder.

Reference numeral 2011 indicates a pipe for conducting the vaporized water or mixture of water and lower alkanol from vessel 2003 into the upper portion of the holder 2001. Reference numeral 2012 indicates a pipe leading from the lower portion of the holder to the vessel 2003, preferably. It is desirable to form pipe 2012 with an upward bend 2013 whereby the water or mixture of water and lower alkanol will be accumulated in the holder to a certain level, that is to say, above the body of reaction or solid catalyst mass, that is, the pulverized cinnamaldehyde-bearing solid materials such as pulverized cinnamon bark ceylon which may be intimately admixed with natural basic catalyst, e.g., limestone, $Mg(OH)_2$ or $Ca(OH)_2$ before being discharged into vessel 2003. When the outflow from the holder is started, it is continued siphonically until the holder is emptied of liquid so that the action is intermittent. The solid-liquid reaction mass residence time in the thimble must be sufficient to allow a final yield of benzaldehyde and acetaldehyde in amounts of 10% or more.

An evacuating mechanism is provided for maintaining a constant sub-atmospheric pressure in the holder, condenser and vaporizing vessel 2003 during that period of time that the reaction is desired to take place. For example, a vacuum pump 2014 may be connected by pipe 2015 to the top of the condenser 2005. The method of the retro-aldol reaction applied to the treatment of the cinnamaldehyde-bearing solid, e.g., pulverized cinnamon bark or pulverized cinnamon leaf, and using the apparatus as above described is as follows:

The pulverized cinnamaldehyde-bearing solid, e.g., cinnamon bark ceylon is comminuted and placed in the 2001. At a 1:1 mole ratio (for example) the solid basic catalyst, e.g., limestone, $Mg(OH)_2$ or $MgO$ or $CaO$ or $Ca(OH)_2$ is added to the pulverized cinnamaldehyde-bearing material (the mole ratio is based on the cinnamaldehyde determined to be in the pulverized cinnamaldehyde-bearing material) and allowed to stand under water, or an aqueous alcohol mixture such as 50:50 mixture of ethyl alcohol and water for a period of time (e.g., 30–40 hours). The water or aqueous alcohol mixture may be used in an amount approximating 40–60% by volum of the pulverized cinnamaldehyde-bearing material, e.g., cinnamon bark Ceylon.

After the pulverized cinnamaldehyde-bearing solid, e.g., cinnamon bark has been macerated, in this manner, as long as necessary, a volume of water or aqueous alcohol, e.g., 50:50 ethanol:water preferably equal to the volumetric contents of the holder 2001 and, in addition, nonionic sorbitan derivative emulsifier (as described, supra) and, if desired, additional cinnamaldehyde-containing oil (e.g., cassia oil) is placed in vessel 2003 and the emulsifier/water or alcohol-water mixture in vessel 2004 is heated to a temperature in the range of 80°-100° C. (e.g., 85° C., for example, when a 50:50 mixture of ethanol and water is present) to bring about vaporization of the alcohol mixture or water. At the same time, the vacuum pump 2014 is started. The pump may be operated so as to maintain a constant vacuum in the apparatus of from approximately 250 mm/Hg pressure up to approximately 750 mm/Hg pressure.

The vaporized solvent passes from vessel 2003 through pipe 2011 into the space 2016 above the material 2002 in holder past multidirection valve 2040 and into the condenser and into the condenser 2005 at this point in time, 2041, 2042, and 2048 valves are kept in a "closed" position. Coming in contact with the water cooled tubes 2008, the vapor is condensed and is refluxed upon the pulverized cinnamaldehyde-bearing material (e.g., cinnamon bark) treated. As soon as the level of the liquid in the holder rises above the upper bend of siphon 2013, the solvent admixed with benzaldehyde and cinnamaldehyde is drawn from the bottom of the holder and discharged into vessel 2003 by the siphoning action described. The vaporization of the solvent and its condensation and precipitation on the pulverized cinnamaldehyde-bearing material, (e.g., cinnamon bark)—basic catalyst mixture (e.g., $Mg(OH)_2$) is continuous so that the extracting operation may be carried on as long as may be necessary in order to remove the reaction product, that is, the high benzaldehyde-containing reaction product from the pulverized cinnamaldehyde-bearing material, (e.g., cinnamon bark) to the extent desired. Ordinarily, the vaporization and condensation of the solvent will not keep pace with its discharge through the siphon so that the operation of the apparatus so far as withdrawal of the solvent and extraction is concerned, will be intermittent. That is, a certain amount of the solvent will collect and remain in contact for a time with the pulverized cinnamaldehyde-bearing material (e.g., pulverized cinnamon bark or pulverized cinnamon leaf) and then will be discharged, the holder being practically emptied of liquid before the siphoning action is stopped.

At the end of the desired time of reaction multidirectional valve 2040 is turned in a position such that vapors are transmitted through line 2043 into condenser 2044 rather than through condenser 2005. Thus, valves 2041, 2042 and 2048 are placed in a "open" position and the vapors then pass through line 2043 and line 2047 when steam from source 2030 is passed through line 2031 past valve 2038 using pump 2039 through sparger 2032 into vessel 2003 thereby causing benzaldehyde-containing reaction product to be vaporized (together with the steam 2033) through line 2011 through head space 2016 and through lines 2047 and 2043, past valves 2040, 2041, 2042 and 2048 using, if desired, pump 2045. The benzaldehyde-containing reaction product is condensed in heat exchanger 2044 and the condensate is passed through line 2051 into benzaldehyde reaction product receiving vessel 2046 from whence it may be recycled into vessel 2003 for further reaction using, for example, additional limestone catalyst at 2002 or additional water soluable sodium bicarbonate (and the like) catalyst which would be located at the vicinity 2032 together with additional nonionic sorbitan derivative containing emulsifier.

FIG. 7A is a schematic diagram of a liquid-liquid phase reaction apparatus which can be used to carry out the retro-aldol reaction of our invention, to wit:

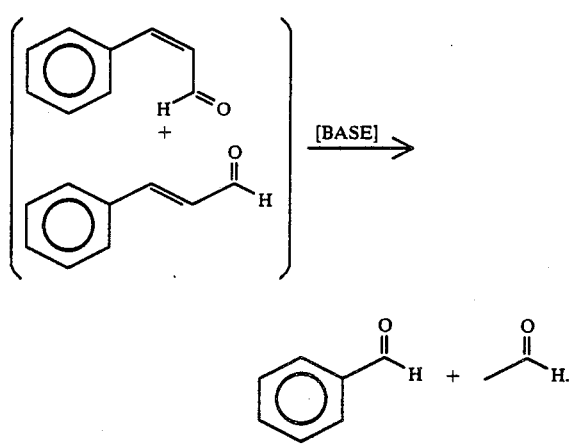

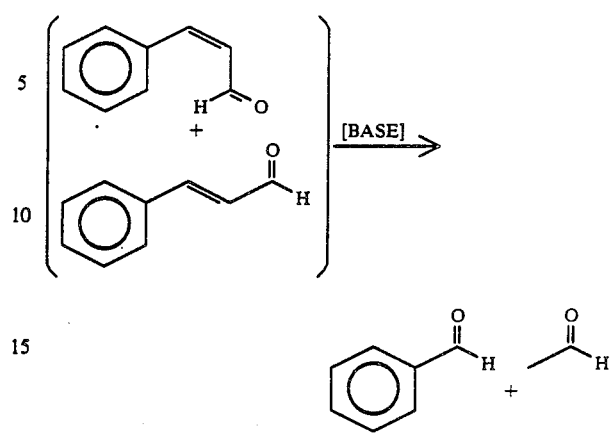

Set forth in FIG. 7A is a liquid-liquid retro-aldol reaction apparatus which is composed of a reaction vessle 169 attached to a packed refluxing column 181 containing packing (e.g., Raschig Rings or Berle Saddles) 182 up to level 183, which, in turn, is connected to the condenser/vapor line/product recovery-return system (hereinafter referred to as the "CVPR" system. The "CVPR" system consists of vapor line 185 containing thermometer or temperature gauge 186 connected back into the main column through line 188; at the very top of the column is condenser 199 surrounded by cooling liquid in jacket 202 with the cooling liquid entering at 201 and exiting at 203. Fixed funnel 187 is located below condenser 199 which has opening 200 leading into fixed funnel 187. Liquid from fixed funnel 187 is directed into movable funnel 189 which is caused to be moved by means of magnet 193 operated using magnetic coil 191 using electric timer 192. Movable funnel 189 can cause liquid to be directed back onto packing surface 183 or the liquid may be directed into tube 194 through opening 190. Hence, according to the way the electric timer is set, condensed liquid may intermittently be directed back into the packing or into recovery tube 194 past valve 197 through tube 205 past valve 207 through tube 216 and opening 217 into separatory funnel 218. Material having a higher vapor pressure such as acetaldehyde proceeds through tube 206 past valve 208 passed "T" joint 211 through valve 210 and tube 226 through opening 227 into cold trap 231 wherein the substantially pure acetaldehyde containing minor impurities is collected (shown by reference numeral 230).

In carrying out the reaction:

a liquid-bearing cinnamaldehyde substance, e.g., cassia oil or cinnamon oil or natural solvent-containing cassia oil or cinnamon oil 170 is placed in reaction vessel 169. Simultaneously, or subsequently base, e.g., sodium carbonate or sodium bicarbonate or proline or choline is placed in reaction vessel 169 with stirring by stirrer 173 powered by stirrer motor 175 through shaft 174. Simultaneously, a nitrogen blanket is maintained over the stirred reaction mass using nitrogen gas pumped in through opening 176 into the reaction vessel 169 at orifice 177. Reaction mass 170 also contains water or a mixture of water and a $C_1$–$C_5$ lower alkanol and a nonionic emulsifier (preferably a sorbitan derivative emulsifier as defined, supra). Steam 295 from source 290 may be continuously or intermittently feed through sparger 294 connected to line 293 into reaction mass 170. The steam line enters the reaction vessel 169 at 292 whereat line 291 is connected. Alternatively, or simultaneously, continuously or intermittently heating mantle 171 containing heating elements 172 is energized while the stirrer motor is in operation. The thus-induced energy causes the reaction mixture 170 to undergo a reaction whereby a mixture of cinnamaldehyde, acetaldehyde and benzaldehyde together with either of the $C_1$–$C_5$ alkanol solvent/water mixture or water is vaporized through opening 180, and reaction flask 179 into packed column 181 containing packing 182 and having a packing surface at 183. The vapor is partially condensed in the packing 182 and the condensed material returns through the packing back into the reaction flask for subsequent reaction. Simultaneously, part of the vapor proceeds through vapor tube 185 past thermometer or temperature gauge 186 through tube 188 back into the column and onto condenser 199. With valve 197 open with respect to tube 198, highly volatile mixture containing acetaldehyde proceeds past the condenser 199 through tube 198 past tube 205 through tube 206 (with valves 208 and 210 "open") through line tube 209 and through tube 226 into cold trap 231 through opening 227. Thus, substantially pure acetaldehyde is collected at 230 using dry ice trap 228 containing dry ice at location 229. Less volatile condensate (e.g., a mixture rich in cinnamaldehyde and benzaldehyde and containing smaller amounts of acetaldehyde) is condensed at 199 and the condensate passes back through opening 200 into fixed funnel 187. The condensate then proceeds into movable funnel 189 wherein part of the condensate is returned through space 184 into packing 182 and then back into the reactor 169 for subsequent reaction and part of the condensate is directed into tube 194 through opening 190 intermittently as a result of the setting of electric timer 192 which operates magnetic coil 191 which actuates magnet 193 causing movable funnel 189 to move laterally; at one point in the time interval causing fluid to enter opening 190 and at another point in the time interval causing fluid to enter the packed column 181 through packing 182. Hence with valve 197 open with respect to tube 194-196, benzaldehyde/cinnamaldehyde reaction product passes through the "U" tube 195 past valve 197 through tube 205 past valve 207 (in open position) through tube 216 through opening 217 into separatory funnel 218 wherein water or mixture of water and alkanol separates out. The benzaldehyde/cinnamaldehyde mixture is located at location 220 and the water or water/alkanol mixture is at location 219 separated at phase separation location 221. When the separatory funnel fills, valve 222 is opened permitting benzaldehyde/cinnamaldehyde mixture 200 to proceed into product container 224 at location 225.

When valve 207 is open, simultaneously, acetaldehyde vapors not condensing may still pass through tube 206 with valve 208 and valve 210 open and valve 212 and 213 closed with the acetaldehyde condensing in cold trap 231 cooled by dry ice 229 in container 228. Otherwise, vapors are vented to the atmosphere if valve 210 is closed and valves 208, 212 and 213 are open with the acetaldehyde passing through tube 206 and passed tube 214. In addition, other vapors may pass through tube 215 through valve 213 into the open atmosphere.

Referring to FIG. 7B, FIG. 7B shows magnetic coil 191 in the vicinity of magnet 193 whereby movable funnel 189 may be moved so that the funnel may be positioned to direct liquid coming into same from funnel 187 either into tube 190 for recovery purposes or back onto packed column 181 (on packing 182) for recycle purposes.

Referring to FIG. 7C, FIG. 7C is a "continuous apparatus" version of the batch type apparatus of FIG. 7A.

In actuality, FIG. 7C is a schematic diagram of a continuous liquid-liquid phase reaction-product recovery apparatus which can be used to carry out the retro-aldol reaction of our invention, to wit:

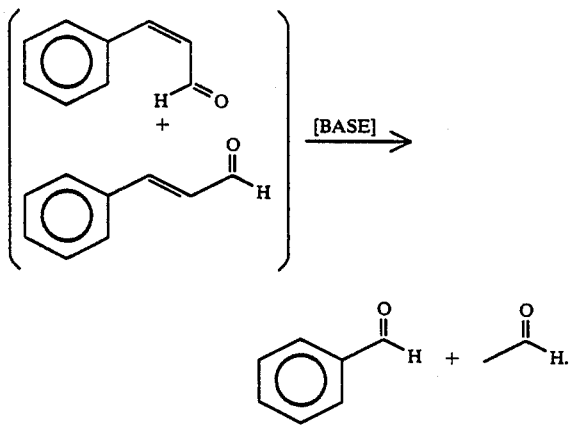

Set forth in FIG. 7C is a liquid-liquid retro-aldol reaction-product recovery apparatus which is composed of a reaction vessel 304 attached to a packed reflux column 305 containing packing 306 which, in turn, is connected to a cooling heat exchanger 321 containing heat exchange tubes 322 cooled using cooling liquid entering at 323 and exiting at 324, which, in turn, is connected to product recovery and recycle system composed of lines 325, 327, two-way valve 326, line 328, valve 329, pump 330 and line 331 and receiver 332.

In carrying out the reaction:

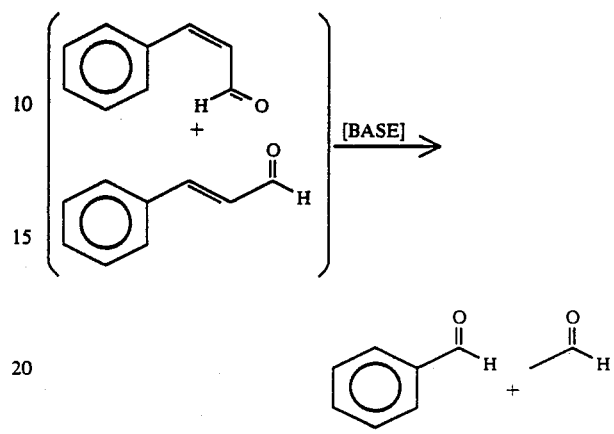

a liquid-bearing cinnamaldehyde substance, e.g., cassia oil or cinnamon oil or natural solvent-containing cassia oil or cinnamon oil 310 contained in container 309 is pumped through line 313 past valve 314 using pump 315 through line 316 into reactor 304. Simultaneously, or subsequently, base 312 such as aqueous sodium bicarbonate contained in holding tank 311 is pumped through line 317 past valve 318 using pump 319 through line 320 into reactor 304 at location 304a. Simultaneously, or subsequently, water or a mixture of $C_1$-$C_5$ alkanol and water in admixture with nonionic sorbitan derivative emulsifier 382 contained in holding tank 381 is pumped through line 385 past valve 383 using pump 384 into reactor 304 at location 304a. The resulting mixture 300 which contains water or a mixture of $C_1$-$C_5$ lower alkanol such as ethyl alcohol and water is heated to reflux and refluxed in packed column 305 having packing 306 (e.g., Raschig Rings or Berle Saddles) while being stirred by stirrer 303. Optionally, continuously or intermittently, atmospheric pressure or high pressure steam 393 is passed into the reaction mass 300 from source 390 through line 391 past valve 396 through sparger 392. The steam has the effect of:
  (i) agitation;
  (ii) imparting activation energy for the reaction; and/or
  (iii) operating to effect fractional steam distillation.

The refluxing substance is continued to be refluxed in packed column 305 having packing 306 until analysis indicates that desired amount of benzaldehyde and acetaldehyde has been formed in the reaction mass 300 whereupon the heat input into reactor 304 is increased whereby a significant portion of the reaction material is distilled (using steam distillation caused by the presence of boiling water at 300) overhead through heat exchanger 321 cooled using cooling liquid entering at 323 and exiting at 324. The resulting condensed material is passed through line 325 past reflux valve 326 through line 328 past valve 329 using pump 330 through line 331 into receiving vessel 332. A portion of the condensed material may be returned back into the reactor 304 past reflux valve 326 through line 327 through pipe 308 back into the packed column 305 containing packing 306 and then back into the reactor 304. In receiver 322, the lower phase is benzaldehyde and acetaldehyde-rich (indicated by reference number 334) and the upper phase is solvent-rich (e.g., water or a mixture of water and lower alkanol)(indicated by reference numeral 333).

If desired, and preferably, the upper phase 333 may be recycled either partially or totally through line 397 using pump 398 past valve 399 back into reactor 304.

The benzaldehyde and acetaldehyde-rich phase is then pumped into opening 338 through line 335 using pump 336 past valve 337 through line 339 into distillation column 340 at location 341 where overhead-rich material is distilled through line 342 past reflux valve 343 through line 345 past valve 346 using pump 347 through line 348 into receiver 350, the acetaldehyde-rich material being indicated by reference numeral 349. The bottoms which are benzaldehyde and cinnamaldehyde-rich are removed through line 351 past return valve 352 through line 354 past valve 355 using pump 356 through line 357 into receiver 358 with the benzaldehyde/cinnamaldehyde-rich phase indicated by reference numeral 359. With regard to distillation column 340, line 344 is the reflux line for the acetaldehyde-rich phase and line 353 is the reboiler line for the benzaldehyde/cinnamaldehyde-rich phase.

The benzaldehyde/cinnamaldehyde-rich phase 359 may then be redistilled in distillation column 365 by passing the contents of receiver 358 through line 360 past valve 361 using pump 362 through line 363 into distillation column 365 at location 364. Overhead distillate rich in benzaldehyde is then removed through line 366 past reflux valve 367 through line 370 past valve 368 using pump 369 into receiver 371 the benzaldehyde-rich material being indicated by reference numeral 372. The bottoms which are cinnamaldehyde-rich are removed through line 373 past return valve 374 through line 378 using pump 377 past valve 376 into receiver 379, the cinnamaldehyde-rich phase indicated by reference numeral 380. The bottom return line is indicated by reference numeral 375.

The entire apparatus is used in the practice of Example VI, infra.

FIG. 8 is the GLC profile for the reaction product of Example VI wherein the reaction:

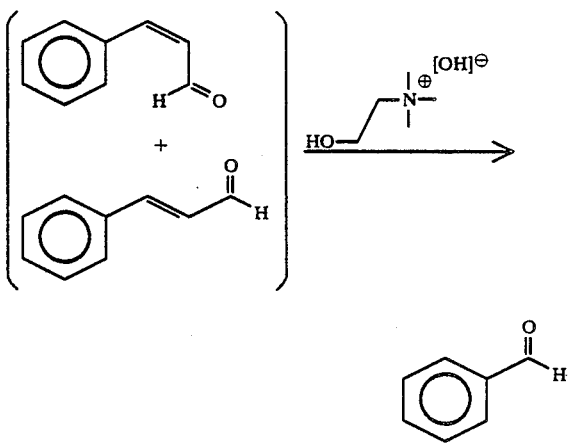

takes place. The peak indicated by reference numeral 800 is the peak for benzaldehyde. The peak indicated by reference numeral 810 is the peak for the cinnamaldehyde.

FIG. 9 is the GLC profile for a first distillation product of the reaction product of Example VI rich in benzaldehyde. The peak indicated by reference numeral 900 is the peak for benzaldehyde.

FIG. 10 is the GLC profile of a second distillation product of the reaction product of Example VI rich in benzaldehyde. The peak indicated by reference numeral 101 is the peak for benzaldehyde.

FIG. 11 is the GLC profile of a third distillation product of the reaction product of Example VI rich in benzaldehyde. The peak indicated by reference numeral 111 is the peak for the benzaldehyde.

FIG. 12 is the total ion current spectrum of a GC-MS analysis of the acetaldehyde-rich material condensed in the "cold trap" 231 as indicated by reference numeral 230 on FIG. 7A. The peak indicated by reference numeral 120 is the peak for acetaldehyde. The shoulder indicated by reference numeral 121 is for ethyl alcohol. The peak indicated by reference numeral 122 is the peak for acetic acid. The peak indicated by reference numeral 123 is the peak for crotonaldehyde. The peak indicated by reference numeral 124 is the peak for benzaldehyde.

FIG. 13 sets forth the apparatus used in the practice of Example XXIV and Example XXV as well as in producing the product used in Example XXVI.

Reaction flask 1301 is equipped with stirrer 1313 attached to stirrer 1314 through moveable sealed joint 1315 powered by motor 1316. Reaction flask 1301 is also fitted with nitrogen sparger 1310 through fitting 1311 with the nitrogen being supplied from source 1307 through line 1308 and apparatus 1309. Reaction flask 1301 is also fitted with heating mantle 1303 and packed Goodloe column 1317 containing packing 1319. The Goodloe column 1317 is fitted at 1334 with distillation head 1326 which is equipped with a magnetic timer 1332/1320. Heating mantle 1303 is powered through lines 1305 from electric power source 1306.

Natural cinnamaldehyde bearing oil (e.g., cassia oil) is admixed with nonionic sorbitan containing emulsifier (as defined, supra) and aqueous water soluable base (e.g., sodium bicarbonate and lithium bicarbonate) and water and the mixture is indicated by reference numeral 1312 to be located in flask 1301. The distillation head 1326 is connected to cold trap 1335/1338/1337 which, in turn, is connected to "Y" tube 1339 and 1344, which, in turn, is connected to line 1345 as well as separatory funnel 1340. Line 1345 (for delivery of the highly volatile acetaldehyde-rich mixture) is fitted to dry-ice/isopropenyl trap 1347/1348/1346 and this trap is fitted to vacuum line 1350 supplied with vacuum source 1349.

Thermometer 1322/1323 is capable of measuring to 0.1° C. and thermometer 1329/1328/1327 has a thermocouple situated immediately after condenser 1324 at 1327. The cold trap 1337/1335/1338 is maintained at −5° down to −10° C. The condensate 1343 is collected in separatory funnel 1340 as indicated by reference numeral 1341 and is periodically transferred to bottles for analysis through valve 1342. The overhead acetaldehyde-rich vapors are conveyed through line 1344 and 1345 to vessel 1346 (dry-ice trap) maintained in container 1347 using dry-ice/isopropenyl mixture 1348 which is vented to a vacuum line 1350 or to the atmosphere through line 1349. If a vacuum is maintained it is slighly less than atmospheric pressure.

It is preferable that the water soluable base (e.g., sodium bicarbonate) is dissolved in water and then a premixture of cinnamaldehyde-containing oil (e.g., cassia oil) and nonionic emulsifier (preferably sorbitan derivative emulsifier, e.g., TWEEN 20) is added to the solution 1312 stirred using stirrer 1313.

The mixture 1312 is heated to reflux using heating mantle 1303 powered through lines 1305 using electric source 1306 while maintaining a high nitrogen flow at 1310 through line 1308 from nitrogen source 1307.

The heating mantle 1303 has its heat adjusted through lines 1305 using electric source 1306 (e.g., "powerstats") whereby a boilup rate is maintained such that the condenser 1324 cools the vapors thereat to approximately 85° C. as indicated on the thermometer 1327/1328/1329 thereby condensing the major part of organics. However, low boilers (including acetaldehyde) water vapor and some benzaldehyde pass through tube 1380 to be condensed by cold traps containing ice at 1336 and containing dry ice at 1348.

Fractions are collected in vessel 1340 at 1341. The oil layer (the bottom layer) is periodically removed through valve 1342 and analyszed by means of gas chromatography.

As the water level falls in the flask 1301 water is added periodically.

The reflux ratio (amount of material taken off through line 1333 versus amount of material returned into reactor 1301) is controlled using magnetic controller 1320 through line 1321 and magnet 1332. Condensate from condenser 1324 is received in funnel 1325. Funnel 1332 can be adjusted in order to direct fluid flow into tube 1333 or back into the reactor 1301 using the magnet 1379 which is connected to power line 1321 which is connected to control device 1320. This determines the amount of benzaldehyde-rich substance which is collected in receiver 1340. The amount of heat input from power source 1306 will ultimately also determine the amount of benzaldehyde and rate of benzaldehyde collected at 1341 and the amount of acetaldehyde collected at 1346.

FIG. 14 is a graph showing temperature and composition changes during steam distillation of the product produced according to Example XXV. The graph indicated by reference numeral 1401 is the graph of temperature versus fraction (the fractions being on a scale of 0 to 90). The graph indicated by reference numeral 1402 is a graph of o-anisaldehyde and cinnamaldehyde versus fraction number with the percent of the combination of cinnamaldehyde and o-anisaldehyde being indicated on the "Y" axis at the right hand side of the graph. The temperature is indicated on the "Y" axis at the left hand side of the graph. The graph indicated by reference numeral 1403 is the graph of percent benzaldehyde versus fraction number with the percent benzaldehyde also being indicated numerically on the "Y" axis at the right hand side of the graph.

FIG. 22 is the GLC profile for vacuum distillation Fraction 1 of the distillation product of the reaction product of Example XXV (Conditions: 50 meter×0.31 mm OV-1 fused silica/methyl silicone column). The peak indicated by reference numeral 2201 is the peak for benzaldehyde. The peak indicated by reference numeral 2202 is the peak for acetaldehyde.

FIG. 23 is the GLC profile for vacuum distillation Fraction 9 of the vacuum distillation of the reaction product of Example XXV. (Conditions: 50 meter×0.31 mm OV-1 fused silica/methyl silicone column programmed at 75°-225° C. at 2° C. per minute). The peak indicated by reference numeral 2301 is the peak for benzaldehyde.

FIG. 24 is the GLC profile for the crude product prior to distillation used for the distillation in Example XXVI (Conditions: 50 meter×0.32 mm fused silica/methyl silicone column programmed at 75°-225° C. at 2.0° C. per minute). The peak indicated by reference numeral 2401 is the peak for acetaldehyde. The peak indicated by reference numeral 2402 is the peak for crotonaldehyde. The peak indicated by reference numeral 2403 is the peak for benzaldehyde. The peak indicated by reference numeral 2404 is the peak for salicyaldehyde, benzyle alcohol, and para cymene. The peak indicated by reference numeral 2405 is the peak for phenylethyl alcohol. The peak indicated by reference numeral 2406 is the peak for 2-methyl benzofuran and isoborneol. The peak indicated by reference numeral 2407 is the peak for cis-cinnamaldehyde. The peak indicated by reference numeral 2408 is the peak for 2-methoxy benzaldehyde. The peak indicated by reference numeral 2409 is the peak for trans cinnamaldehyde.

FIG. 25 is the GLC profile for the crude product prior to distillation used in the distillation of Example XXVI (Conditions: 50 meter×0.32 mm fused silica/carbowax 20M column programmed at 75°-225° C. at 2.0° C. per minute). The peak indicated by reference numeral 2501 is the peak for acetaldehyde. The peak indicated by reference numeral 2502 is the peak for croton aldehyde. The peak indicated by reference numeral 2503 is the peak for benzaldehyde. The peak indicated by reference numeral 2504 is the peak for beta caryofalene. The peak indicated by reference numeral 2505 is the peak for salisaldehyde. The peak indicated by reference numeral 2506 is the peak for isoborneol. The peak indicated by reference numeral 2507 is the peak for 2-methyl benzofuran. The peak indicated by reference numeral 2508 is the peak for cis-cinnamaldehyde. The peak indicated by reference numeral 2509 is the peak for phenylethyl alcohol. The peak indicated by reference numeral 2510 is the peak for 2-methoxy benzaldehyde. The peak indicated by reference numeral 2511 is the peak for trans cinnamaldehyde.

Acetaldehyde has the structure:

Cinnamaldehyde has the structure:

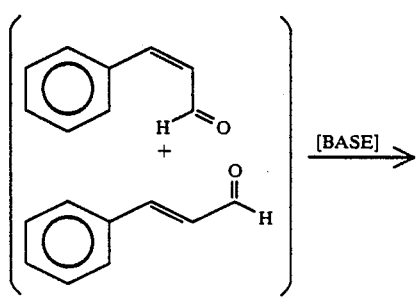

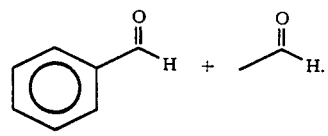

Benzaldehyde has the structure:

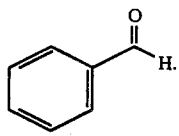

Beta caryophyllene has the structure:

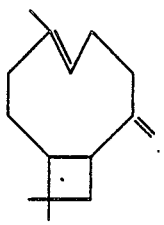

Salacylaldehyde has the structure:

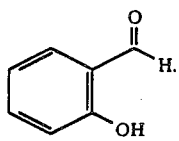

Isoborneol has the structure:

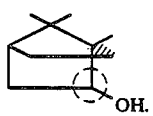

2-Methyl benzofuran has the structure:

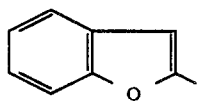

Cis-cinnamaldehyde has the structure:

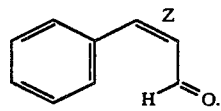

Phenylethyl alcohol has the structure:

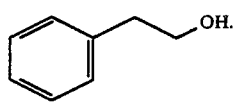

2-Methoxy benzaldehyde has the structure:

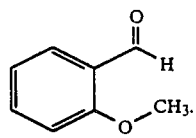

Trans cinnamaldehyde has the structure:

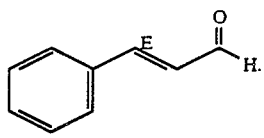

Benzyl alcohol has the structure:

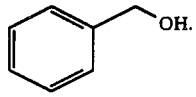

Para cymene has the structure:

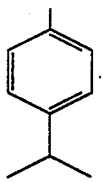

FIG. 27 is the GLC profile for the crude reaction product of Example XXXIX (Conditions: 50 m×0.32 mm fused silica/methyl silicone column programmed at 75°–225° C. at 2.0° C. per minute). The peak indicated by reference numeral 2701 is the peak for benzaldehyde.

In further illustration of this invention the following examples are given. The instant invention should not be limited to these examples but is only limited by the scope of the claims as set forth, infra.

EXAMPLE I

Preparation of Natural Benzaldehyde-Cinnamaldehyde Mixture

Reaction:

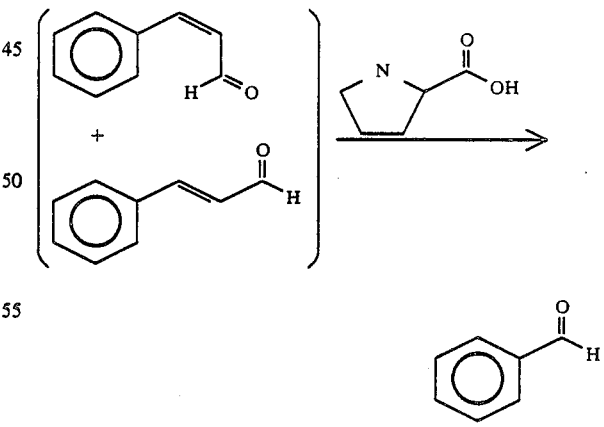

Into a 250 ml, three neck flask is placed 10 grams cassia oil, 50 ml ethanol (95% foodgrade), 50 ml distilled water and 2 grams of L-proline (natural). Boiling chips are added and a water-washed stream of nitrogen is past over the reaction mass to help prevent oxidation of the formed benzaldehyde. The mixture is heated to reflux and refluxed for a period of 18 hours at atmospheric pressure (82° C.).

The resulting product contains 40% benzaldehyde and 60% cinnamaldehyde.

FIG. 1 is the GC-IR spectrum for the resulting product. The peak indicated by reference numeral 10 is the peak for the benzaldehyde reaction product. The peak indicated by reference numeral 11 is the peak for the unreacted cinnamaldehyde.

The resulting material is fractionally distilled. The bottoms at the end of the fractional distillation are analyzed.

FIG. 2 is the GC-IR spectrum for the bottoms in the distillation pot. The peak indicated by reference numeral 20 is the peak for benzaldehyde. The peak indicated by reference numeral 21 is the peak for the cinnamaldehyde.

EXAMPLE II

Preparation of Natural Cinnamaldehyde and Natural Benzaldehyde

Reaction:

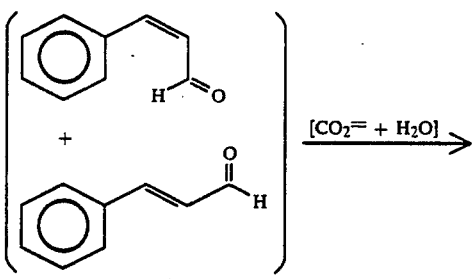

Into a three neck flask equipped with stirrer, thermometer and reflux condenser is placed 10 grams of cassia oil and 100 ml of a 3% aqueous sodium carbonate solution. Boiling chips are added and a water-washed stream of nitrogen is passed over the reaction mass to help prevent oxidation of the formed benzaldehyde. The mixture is heated to reflux and refluxed for a period of 7 hours (100° C.). The resulting material contains 70% benzaldehyde and 30% cinnamaldehyde.

FIG. 3 is the GC-IR spectrum for the crude reaction mass. The peak indicated by reference numeral 30 is the peak for benzaldehyde. The peak indicated by reference numeral 31 is the peak for the cinnamaldehyde. (Conditions: Carbowax column programmed at 75°-225° C. per minute).

EXAMPLE III

At the rate of 3% to two separate samples of natural cherry liquer the product of Example I and the product of Example II are added. In each of the cases the resulting cherry liqueur has a more natural, more aesthetically pleasing rich, ripe cherry aroma and taste nuance remeniscent of natural cherry flavor. A bench panel of five members not associated with the inventive entity of the instant application unanimously prefers the cherry liquer containing the products of Examples I and II to the products not containing such materials.

EXAMPLE IV

Each of the cherry liqueurs produced in Example III is intimately admixed with carbonated Perrier ® water at the weight ratios of 50:50 (Perrier water:cherry liqueur). The resulting "carbonated" beverage has an excellent, natural cherry aroma and taste. A bench panel of five members prefers the "resulting cherry soda" to a similar cherry soda produced without the use of the products of Examples I or II.

EXAMPLE V

A cherry fruit puree is produced (for the purpose of adding to an unflavored yogurt). At the level of 0.1%, each of the products of Examples I and II is added to separate samples of the cherry puree. At the rate of 10% each of the cherry puree samples is added to unflavored yogurt and intimately admixed therewith. A bench panel of five members not associated with the inventive entity of the instant application unanimously prefers the cherry flavored yogurt containing the products of Examples I and II to the same product not containing such materials.

EXAMPLE VI

Preparation of Natural Benzaldehyde-Cinnamaldehyde Mixture and Natural Acetaldehyde Composition Reaction:

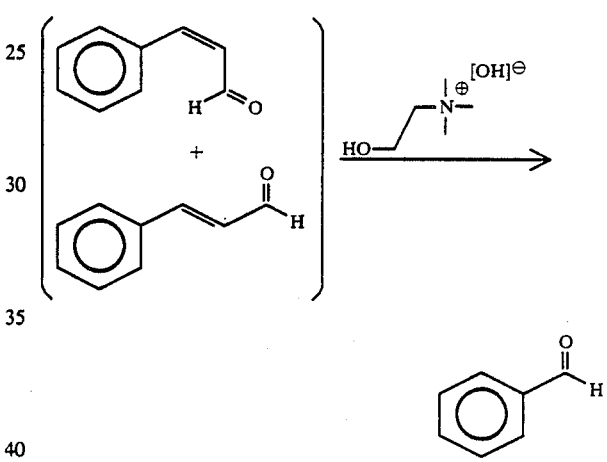

Into a reaction vessel in the apparatus as set forth in FIG. 7A, equipped with stirrer, thermometer and reflux packed column fitted with overhead condenser to which are connected receivers for benzaldehyde-rich materials and acetaldehyde-rich materials as specified, supra, are placed 1 liter of water, 50 grams cassia oil and 20 ml of a 45% solution of choline base in methyl alcohol.

The reaction mass is heated to reflux and maintained at reflux for a period of 0.5 hours, at which point in time, 20 ml of a 45% solution of choline base in methanol is added. The reaction mass is continued to be refluxed for a period of 4 hours. At the end of the 4 hours, slowly removing the methanol from the system through the overhead condenser with the reflux temperature rising from 65° C. to 99° C. At the end of the 4 hour period, 300 ml water is added to the reaction mass. The reaction mass is then refluxed for a period of 8 hours. At the end of the 8 hour refluxing period, additional heat is imparted to the reaction vessel whereby the reaction product begins to be distilled using the overhead condenser 199 and the controlled reaction product recovery apparatus shown in FIGS. 7A and 7B into (i) receiver 218 where the benzaldehyde-rich fraction 220 is collected and (ii) cold trap 231 where the acetaldehyde-rich material 230 is condensed and collected.

The original cassia oil utilized contained 88% cinnamaldehyde.

The yield of benzaldehyde based on 88% cinnamaldehyde-containing cassia oil is 65%. The third distillation fraction contained a ratio of benzaldehyde:-cinnamaldehyde of 13:1.

FIG. 8 is the GLC profile of the reaction product prior to the first distillation. The peak indicated by reference numeral 800 is the peak for benzaldehyde. The peak indicated by reference numeral 810 is the peak for cinnamaldehyde.

FIG. 9 is the GLC profile for the first distillation of the benzaldehyde-rich phase 89. The peak indicated by reference numeral 900 is the peak for benzaldehyde.

FIG. 10 is the GLC profile for the second distillation of the lower phase benzaldehyde-rich product. The peak indicated by reference numeral 101 is the peak for benzaldehyde.

FIG. 11 is the GLC profile for the third distillation of the benzaldehyde-rich phase. The peak indicated by reference numeral 111 is the peak for benzaldehyde.

FIG. 12 is the total ion current spectrum of a GC-MS analysis of the acetaldehyde-rich composition containing minor impurities 230 trapped in cold trap 231 of the apparatus of FIG. 7A. The peak indicated by reference numeral 120 is the peak for the acetaldehyde. The shoulder indicated by reference numeral 121 is for ethyl alcohol. The peak indicated by reference numeral 122 is the peak for acetic acid. The peak indicated by reference numeral 123 is the peak for crotonaldehyde. The peak indicated by reference numeral 124 is the peak for benzaldehyde.

EXAMPLE VII

The following sweet cherry flavor formulation is prepared:

| Ingredients | Parts by Weight |
|---|---|
| Allyl isovalerate | 15.0 |
| Amyl butyrate | 200.0 |
| Anisic aldehyde | 37.0 |
| Anisyl acetate | 25.0 |
| Anisyl butyrate | 12.0 |
| Anisyl propionate | 12.0 |
| Benzyl acetate | 50.0 |
| Third distillation product of the reaction product of Example VI (identified by the GLC profile of FIG. 11) | 4,658.0 |
| Eugenol | 7.0 |
| Cyclohexyl cinnamate | 5.0 |
| Cyclohexyl formate | 8.0 |
| Ethyl acetate | 680.0 |
| Ethyl butyrate | 152.0 |
| Ethyl methylglycidate | 100.0 |
| Rhodinol | 60.0 |
| Beta-ionone | 4.0 |
| Jasmine absolute | 13.0 |
| Citral | 1.0 |
| Maltol (5% in ethanol) | 1.0 |
| Orris butter | 30.0 |
| Orris resinoid | 160.0 |
| Rhodinyl formate | 1.0 |
| Rhodinyl isovalerate | 12.0 |
| Para-Toluic aldehyde | 500.0 |
| Vanillin | 400.0 |
| Propylene glycol | 2,920.0 |
| Total | 10,000.0 |

The resulting flavor is compared with the same flavor produced using a mixture of bitter almond essential oil and extracted Ceylon, cinnamon, cinnamaldehyde in a combined amount of 4658.0 parts by weight (grams). The cherry flavor containing the third distillation product of the reaction product of Example VI is unanimously preferred by a bench panel of five members independent of the inventive entity of the instant patent application due to the more natural nature of the overall flavor. The natural cherry nuances imparted using the third distillation product of the reaction product of Example VI gives rise to unexpected, unobvious and advantageous properties of the resulting cherry flavor formulation.

EXAMPLE VIII

A. Powder Flavor Formulation

Twenty grams of the flavor composition of Example VII is emulsified in a solution containing 300 grams gum acacia and 700 grams of water. The emulsion is spray dried with a Bowen Lab Model Drier utilizing 260 c.f.m. of air with an inlet temperature of 500° F. and an outlet temperature of 200° F. and a wheel speed of 50,000 rpm.

B. Sustained Release Flavor

The following mixture is prepared:

| Ingredients | Parts by Weight | |
|---|---|---|
| Liquid cherry flavor composition of Example VII | 20 | |
| Propylene glycol | 9 | |
| Cab-O-Sil ® M-5 (brand of silica produced by the Cabot Corp. of 125 High Street, Boston, Mass. 02110) | 5 | |
| Physical properties: | | |
| Surface area: | 200 | m²/gm |
| Nominal particle size: | 0.012 | microns |
| Density: | 2.3 | lbs/cu. ft. |

The Cab-O-Sil ® is dispersed in the liquid cherry flavor composition of Example VII with vigorous stirring thereby resulting in a viscous liquid. Seventy-one parts by weight of the powder flavor composition of Part A, supra, is then blended into said viscous liquid with stirring at 25° C. for a period of 30 minutes resulting in a dry, free-flowing sustained release flavor powder.

EXAMPLE IX

Ten parts by weight of 50 Bloom pigskin gelatin is added to ninety parts by weight of water at a temperature of 150° F. The mixture is agitated until the gelatin is completely dissolved and the solution is cooled to 120° F. Twenty parts by weight of the liquid flavor composition of Example VII is added to the solution which is then homogenized to form an emulsion having a particle size typically in the range of 5–40 microns. The material is kept at 120° F. under which conditions the gelatin will not gel.

Coacervation is induced by adding slowly and uniformly, forty parts by weight of a 20% aqueous solution of sodium sulphate. During coacervation of gelatin, molecules are deposited uniformly about each oil droplet as a nucleus.

Gelation is effected by pouring the heated coacervate mixture into 1,000 parts by weight of a 7% aqueous solution of sodium sulphate at 65° F. The resulting gelled coacervate may be filtered and washed with water at temperatures below the melting point of gelation, to remove the salt.

Hardening of the filter cake, in this example, is effected by washing with 200 parts by weight of 37% solution of formaldehyde in water. The cake is then washed to remove the residual formaldehyde.

EXAMPLE X

Chewing Gum

One hundred parts by weight of chicle are mixed with four parts by weight of the flavor prepared in accordance with Example VIII, Part B. Three hundred parts of sucrose and one hundred parts of corn syrup are added. Mixing is effected in a ribbon blender with jacketed side walls of the type manufactured by the Baker Perkins Co.

The resultant chewing gum blend is then manufactured into strips one inch in width and 0.1 inches in thickness. The strips are cut into lengths of three inches each. On chewing, the chewing gum has a pleasant, long-lasting natural cherry flavor.

EXAMPLE XI

One hundred parts by weight of chicle are mixed with eighteen parts by weight of the flavor prepared in accordance with Example IX. Three hundred parts of sucrose and one hundred parts of corn syrup are then added. Mixing is effected in a ribbon blender with jacketed side walls of the type manufactured by the Baker Perkins Co.

The resultant chewing gum blend is then manufactured into strips one inch in width and 0.1 inches in thickness. The strips are cut into lengths of 3" each. On chewing, the chewing gum has a pleasant, long-lasting natural cherry flavor.

EXAMPLE XII

Toothpaste Formulation

The following separate groups of ingredients are prepared:

| Parts by Weight | Ingredients |
|---|---|
| Group "A" | |
| 30.200 | Glycerine |
| 15.325 | Distilled water |
| 0.100 | Sodium benzoate |
| 0.125 | Saccharin sodium |
| 0.400 | Stannous fluoride |
| Group "B" | |
| 12.500 | Calcium carbonate |
| 37.200 | Dicalcium phosphate (dihydrate) |
| Group "C" | |
| 2.000 | Sodium n-lauroyl sarcosinate (foaming agent) |
| Group "D" | |
| 1.200 | Flavor material of Example VIII, Part B |
| 100.000 | (Total) |

Procedure:
1. The ingredients in Group "A" are stirred and heated in a steam jacketed kettle to 160° F.
2. Stirring is continued for an additional three to five minutes to form a homogeneous gel.
3. The powders of Group "B" are added to the gel, while mixing until a homogeneous paste is formed.
4. With stirring, the flavor of "D" is added and lastly, the sodium n-lauroyl sarcosinate.
5. The resultant slurry is then blended for one hour. The completed paste is then transferred to a three roller mill and then homogenized, and finally tubed.

The resulting toothpaste, when used in a normal toothbrushing procedure, yields a pleasant, sweet, cherry flavor of constant strong intensity throughout said procedure (1–1.5 minutes).

EXAMPLE XIII

Chewable Vitamin Tablets

The flavor material produced according to the process of Example VIII, Part B, is added to a chewable vitamin tablet formulation at a rate of 10 gm/kg which chewable vitamin tablet formulation is prepared as follows:

In a Hobart Mixer, the following materials are blended to homogeneity:

| Ingredients | Gms/1000 Tablets |
|---|---|
| Vitamin C (ascorbic acid as ascorbic acid-sodium ascorbate mixture 1:1) | 70.000 |
| Vitamin $B_1$ (thiamine mononitrate) as Rocoat ® thiamine mononitrate 33⅓% (Hoffman LaRoche) | 4.000 |
| Vitamin $B_2$ (riboflavin) as Rocoat ® riboflavin 33⅓% | 5.000 |
| Vitamin $B_6$ (pyridoxine hydrochloride) as Rocoat ® pyridoxine hydrochloride 33⅓% | 4.000 |
| Niacinamide as Rocoat ® niacinamide 33⅓% | 33.000 |
| Calcium pantothenate | 11.000 |
| Vitamin $B_{12}$ (cyanocobalamin) as Merck 0.1% in gelatin | 3.500 |
| Vitamin E (dl-alpha topcopheryl acetate) as dry Vitamin E acetate 33⅓% Roache | 6.600 |
| d-Biotin | 0.044 |
| Certified lake color | 5.000 |
| Flavor of Example VIII, Part B | as indicated above |
| Sweetener sodium saccharin | 1.000 |
| Magnesium stearate lubricant | 10.000 |
| Mannitol q.s. to make | 500.000 |

Preliminary tablets are prepared by slugging with flatfaced punches and grinding the slugs to 14 mesh. 13.5 Grams dry Vitamin A acetate and 0.6 grams Vitamin D are then added as beadlets. The entire blend is then compressed using concave punches at 0.5 grams each.

Chewing of the resultant tablets yields a pleasant, long-lasting, consistently strong, cherry flavor for a period of 12 minutes.

EXAMPLE XIV

Chewing Tobacco

Onto 100 pounds of tobacco for chewing (85% Wisconsin lead and 15% Pennsylvania lead) the following casing is sprayed at a rate of 30%:

| Ingredients | Parts by Weight |
| --- | --- |
| Corn syrup | 60.0 |
| Licorice | 10.0 |
| Glycerine | 20.0 |
| Fig juice | 4.6 |
| Prune juice | 5.0 |
| Flavor material of Example VIII of Part B | 0.4 |

The resultant product is redried to a moisture content of 20%. On chewing, this tobacco has an excellent substantially consistent, long-lasting, sweet, cherry nuance (20 minutes) in conjunction with the main fruity tobacco note.

EXAMPLE XV

Flavored Foodstuff 2.25 Ounces of a coconut macaroon mix distributed by Drake Bakeries, Division of Bordon, Inc. of Columbus, Ohio 43215 is intimately admixed at the level of 20 ppm with the benzaldehyde/cinnamaldehyde mixture (second distillation product) prepared according to Example VI.

The coconut macaroon composition contains corn syrup, coconut, sugar and egg whites.

The coconut macaroon composition is then baked at 325° F. at atmospheric pressure for a period of 20 minutes. The resultant coconut macaroon cookies have an excellent "natural coconut" notes with intense almond nuances not present in the cookies without the composition of Example VI.

When the composition of Example VI is replaced with the compositions of Examples I or II, a similar natural coconut almond nuance is created.

EXAMPLE XVI

Tobacco Flavor Formulation and Tobacco

A tobacco mixture is produced by admixing the following materials:

| Ingredients | Parts by Weight |
| --- | --- |
| Bright | 40.1 |
| Burley | 24.9 |
| Maryland | 1.1 |
| Turkish | 11.6 |
| Stem (flue-cured) | 14.2 |
| Glycerine | 2.8 |
| Water | 5.3 |

Cigarettes having cellulose acetate filters are prepared from this tobacco:

The following flavor formulation is prepared:

| Ingredients | Parts by Weight |
| --- | --- |
| Ethyl butyrate | .05 |
| Ethyl valerate | .05 |
| Maltol | 2.00 |
| Cocoa extract | 26.00 |
| Coffee extract | 10.00 |
| Ethyl alcohol (95% aqueous) | 20.00 |
| Water | 41.90 |

The above-stated tobacco flavor formulation is applied at the rate of 0.1% to all of the cigarettes produced using the above tobacco formulation. One-third of the cigarettes are then treated in the tobacco section thereof with 5 ppm of the benzaldehyde/cinnamaldehyde mixture produced by the third distillation of Example VI. One-third of the cigarettes are treated on the cellulose acetate filter with 1 microliter of a 0.1% ethanol solution of the cinnamaldehyde/benzaldehyde mixture of the third distillation of Example VI.

The above-stated tobacco formulation is applied at the rate of 0.1% to all of the cigarettes produced using the above tobacco formulation. One-third of the cigarettes are then treated in the tobacco section thereof with 5 ppm of benzaldehyde/cinnamaldehyde mixture produced by the third distillation of Example VI. One-third of the cigarettes are treated on the cellulose acetate filter with 1 microliter of a 0.1% ethanol solution of the cinnamaldehyde/benzaldehyde mixture of the third-distillation of Example VI.

The control cigarettes not containing the mixture of benzaldehyde and cinnamaldehyde produced according to the process of Example VI and the experimental cigarettes which do contain the mixture of benzaldehyde and cinnamaldehyde produced according to the process of Example VI are evaluated by three-way comparison, and the results are as follows:

In aroma, the cigarettes containing the benzaldehyde and cinnamaldehyde of Example VI in the tobacco or in the filter have been found to be sweeter and fruitier with faint aesthetically pleasing cherry nuances.

In smoke flavor, the cigarettes containing the benzaldehyde and cinnamaldehyde mixture are more aromatic, more sweet, fruitier and slightly less harsh in the mouth and throat. In addition, those cigarettes containing the benzaldehyde and cinnamaldehyde mixture of Example VI in the tobacco give rise to a fruity nuance in the taste and aroma on smoking.

EXAMPLE XVII

Apple Flavor Formulation

The following basic apple flavor formulation is prepared:

| Ingredients | Parts by Weight |
| --- | --- |
| Amyl acetate | 1.0 |
| Gamma decalactone | 1.5 |
| Caproic acid | 1.5 |
| n-Hexyl acetate | 2.5 |
| Coriander Oil | 0.5 |
| n-Hexyl iso-butyrate | 2.5 |
| n-Hexanal | 5.0 |
| Ethyl isovalerate | 5.0 |
| cis-3-Hexenol | 18.0 |
| Ethyl-2-methyl butyrate | 18.0 |
| trans-2-Hexenal | 18.0 |
| Apple Fusel Oil | 26.0 |
| Maltol | 0.5 |
| 95% Food grade ethanol | 100.0 |

This basic apple flavor is compared, in water, with and without the addition of natural acetaldehyde prepared according to Example XXV at the rate of 6 ppm and at the rate of 10 ppm in water. The flavor with the addition of the natural acetaldehyde composition has a fresh apple juice character with light fruity topnotes. Both notes are missing in the flavor that does not contain the natural acetaldehyde composition of Example XXV. For this reason, the flavor with the natural acetaldehyde composition of Example XXV is preferred unanimously by a three-member bench panel.

EXAMPLE XVIII

A. Powder Flavor Formulation

20 Grams of the flavor formulation of Example IV is emulsified in a solution containing 300 g gum acacia and 700 g water. The emulsion is spray-dried with a Bowen Lab Model Drier utilizing 260 c.f.m. of air with an inlet temperature of 500° F., an outlet temperature of 200° F. and a wheel speed of 50,000 rpm.

B. Sustained Release Flavor

The following mixture is prepared:

| Ingredients | Parts by Weight |
| --- | --- |
| Liquid Apple Flavor of Example IV | 20.00 |
| Propylene Glycol | 9.00 |
| Cab-O-Sil ® M-5 Brand of Silica produced by the Cabot Corporation of 125 High Street, Boston, Mass. 02110 | 5.00 |
| Physical Properties: | |
| Surface Area: | 200 m$^2$/gm |
| Nominal particle size: | 0.012 microns |
| Density: | 2.3 lbs/cu. ft. |

The Cab-O-Sil is dispersed in the liquid apple flavor composition of Example XVII with vigorous stirring, thereby resulting in a viscous liquid. 71 Parts by weight of the powder flavor composition of Part I, supra, is then blended into the said viscous liquid, with stirring at 25° C. for a period of 30 minutes, resulting in a dry, free-flowing sustained release powder.

EXAMPLE XIX

10 Parts by weight of 50 Bloom pigskin gelatin is added to 90 parts by weight of water at a temperature of 150° F. The mixture is agitated until the gelatin is completely dissolved and the solution is cooled to 120° F. 20 Parts by weight of the liquid apple flavor composition of Example XVII is added to the solution which is then homogenized to form an emulsion having particle size typically in the range of 5–40 microns. This material is kept at 120° F. under which conditions, the gelatin will not gel.

Coacervation is induced by adding slowly and uniformly, 40 parts by weight of a 20% aqueous solution of sodium sulphate. During coacervation the gelatin molecules are deposited uniformly about each oil droplet as a nucleus.

Gelation is effected by pouring the heated coacervate mixture into 1,000 parts by weight of 7% aqueous solution of sodium sulphate at 65° F. The resulting jelled coacervate may be filtered and washed with water at temperatures below the melting point of gelatin, to remove the salt.

Hardening of the filtered cake, in this example, is effected by washing with 200 parts by weight of 37% solution of formaldehyde in water. The cake is then washed to remove residual formaldehyde.

EXAMPLE XX

Chewing Gum

100 Parts by weight of chicle are mixed with 4 parts by weight of the flavor prepared in accordance with Example XVIII(B). 300 Parts of sucrose and 100 parts of corn syrup are added. Mixing is effected in a ribbon blender with jacketed walls of the type manufactured by the Baker Perkins Co.

The resultant chewing gum blend is then manufactured into strips 1″ in width and 0.1″ in thickness. The strips are cut into lengths of 3″ each. On chewing, the chewing gum has a pleasant, long-lasting apple flavor.

EXAMPLE XXI

Chewing Gum

100 Parts by weight of chicle are mixed with 18 parts by weight of the flavor prepared in accordance with Example XIX. 300 Parts of sucrose and 100 parts of corn syrup are then added. Mixing is effected in a ribbon blender with jacketed walls of the type manufactured by the Baker Perkins Co.

The resultant chewing gum blend is then manufactured into strips 1″ in width and 0.1″ in thickness. The strips are cut into lengths of 3″ each. On chewing, the chewing gum has a pleasant, long-lasting apple flavor.

EXAMPLE XXII

Toothpaste Formulation

The following separate groups of ingredients are prepared:

| Parts by Weight | Ingredient |
| --- | --- |
| Group "A" | |
| 30.200 | Glycerine |
| 15.325 | Distilled Water |
| .100 | Sodium Benzoate |
| .125 | Saccharin Sodium |
| .400 | Stannous Fluoride |
| Group "B" | |
| 12.500 | Calcium Carbonate |
| 37.200 | Dicalcium Phosphate (Dihydrate) |
| Group "C" | |
| 2.000 | Sodium N—Lauroyl Sarcosinate (foaming agent) |
| Group "D" | |
| 1.200 | Flavor Material of Example XVIII(B) |
| 100.00 - TOTAL | |

Procedure:
1. The ingredients in Group "A" are stirred and heated in a steam jacketed kettle to 160° F.
2. Stirring is continued for an additional three to five minutes to form a homogeneous gel.
3. The powders of Group "B" are added to the gel, while mixing, until a homogeneous paste is formed.
4. With stirring, the flavor of "D" is added and lastly the sodium-n-lauroyl sarcosinate.
5. The resultant slurry is then blended for one hour The completed paste is then transferred to a three roller mill and then homogenized, and finally tubes.

The resulting toothpaste, when used in a normal toothbrushing procedure yields a pleasant apple flavor, of constant strong intensity throughout said procedure (1–1.5 minutes).

EXAMPLE XXIII

Chewable Vitamin Tablets

The flavor material produced according to the process of Example XVIII(B) is added to a Chewable Vitamin Tablet Formulation at a rate of 10 mg/Kg, which Chewable Vitamin Tablet Formulation is prepared as follows.

In a Hobart Mixer, the following materials are blended to homogeneity:

| Ingredients | Gms/1000 Tablets |
|---|---|
| Vitamin C (ascorbid acid) as ascorbic acid-sodium ascorbate mixture 1:1 | 70.11 |
| Vitamin B₁ (thiamine mononitrate) as Rocoat ® thiamine mononitrate 33⅓% (Hoffman La Roche) | 4.00 |
| Vitamin B₂ (riboflavin as Rocoat ® roboflavin 33⅓% | 5.00 |
| Vitamin B₆ (pyridoxine hydrochloride) as Rocoat ® pyridoxine 33⅓% | 4.00 |
| Niacinamide as Rocoat ® niacinamide 33⅓% | 33.00 |
| Calcium pantothenate | 11.5 |
| Vitamin B₁₂ (cyanocobalamin) as Merck 0.1% in geltain | 3.5 |
| Vitamin E (dl-alpha tocopheryl acetate) as dry Vitamin E acetate 33⅓% | 6.6 |
| d-Biotin | 0.044 |
| Flavor of Example XVIII(B) | (as indicated above) |
| Certified lake color | 5.0 |
| Sweetener - sodium saccharin | 1.0 |
| Magnesium stearate lubricant | 10.0 |
| Mannitol q.s. to make | 500.0 |

Preliminary tablets are prepared by slugging with flatfaced punches and grinding the slugs to 14 mesh. 13.5 g Dry Vitamin A Acetate and 0.6 g Vitamin D are then added as beadlets. The entire blend is then compressed using concave punches at 0.5 g each.

Chewing of the resultant tablets yields a pleasant, long-lasting, consistently strong apple flavor for a period of 12 minutes.

EXAMPLE XXIV

Preparation of Natural Benzaldehyde-Cinnamaldehyde Mixture and Natural Acetaldehyde Composition Reaction:

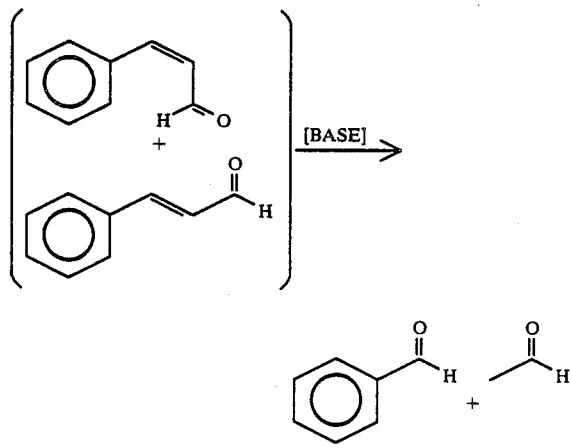

Into a reaction vessel in the apparatus as set forth in FIG. 13 (12 liter 3 neck flask) equipped with nitrogen sparge, electric stirrer, heating mantle and 4' Goodloe packed column with distillation head and magnetic timer are placed 600 grams of sodium bicarbonate dissolved in 6 liters of water. A premixture of 2.5 kilograms of cassia oil F. P. (containing 71% cinnamaldehyde) and 15 grams of TWEEN 20 having the structure:

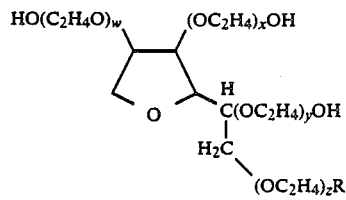

wherein $W+X+Y+Z=20$ and the R moiety represents 55% monolaurate moiety with the balance myristate, palmitate and stearate moieties is prepared. The premixture is added to the sodium bicarbonate solution.

The resulting mixture is heated to reflux while maintaining a 2125 ml/minute nitrogen fluorate. The reflux ratio is set at 19:1. After two hours, the nitrogen flourate is reduced to 650 ml/minute.

The heat input is adjusted to maintain the boilup rate such that the condenser cools the vapors to approximately 85° C. thereby condensing a major part of the organics. However, the low boiler, water vapor and some benzaldehyde pass down tube 1380 to be condensed in cold traps 1338 and 1346.

Fractions collected at 1341 are transferred to bottles and analyzed by means of GLC.

As the water level falls in the flask 1301, 1 liter of water is added approximately every ten hours.

The reaction is monitored (temperature and GC analysis) to determine the progress of conversion of conversion of cinnamaldehyde to benzaldehyde. The vapor temperature is an excellent indicator of the composition of the vapor and this is measured by thermometer 1322. FIG. 19 is the GLC profile for cassia oil used in this example (Conditions: Fused silica/carbowax 20M column). The cassia oil is steam distilled and FIG. 20 is the GLC profile for the steam distilled cassia oil used in this example (Conditions: 10 meter×0.32 mm fused silica/carbowax 20M column).

The reaction is monitored by GLC: Conditions: 0.125"×8' SE-30 column programmed at 100°-220° C. at 8° C. per minute.

The following Table I and II set forth changes in temperature and oil composition for two separate batches of cassia oil. The results of Table I are also set forth in FIG. 14:

TABLE I

| PRODUCTION OF BENZALDEHYDE FROM CASSIA OIL | | | | | |
|---|---|---|---|---|---|
| | | | Back Peaks | | |
| Fraction No. | Temp. (°C.) | Percent Benzaldehyde | Anis- alde- hyde | Cinna- mal- dehyde | Total |
| 5 | 97.2 | 27.4 | — | 44.9 | 44.9 |
| 6 | 99.5 | 41.1 | 0.5 | 22.8 | 23.3 |
| 7 | 99.5 | 56.6 | 0.5 | 19.1 | 19.6 |
| 10 | 99.4 | 72.7 | 0.4 | 9.8 | 10.2 |
| 15 | 99.3 | 83.8 | 0.3 | 5.6 | 5.9 |
| 20 | 98.8 | 90.7 | 0.2 | 2.8 | 3.0 |
| 25 | 98.7 | 92.8 | 0.2 | 1.1 | 1.3 |
| 30 | 98.7 | 93.7 | 0.2 | 0.9 | 1.1 |
| 34 | 98.6 | 93.0 | 0.3 | 1.5 | 1.8 |
| 35 | 98.6 | 91.8 | 0.3 | 1.9 | 2.2 |
| 36 | 98.6 | 93.3 | 0.4 | 1.8 | 2.2 |

TABLE I-continued

PRODUCTION OF BENZALDEHYDE FROM CASSIA OIL

| Fraction No. | Temp. (°C.) | Percent Benzaldehyde | Back Peaks Anisaldehyde | Back Peaks Cinnamaldehyde | Total |
|---|---|---|---|---|---|
| 40 | 98.6 | 93.7 | 0.3 | 1.5 | 1.8 |
| 45 | 98.5 | 95.0 | 0.3 | 1.0 | 1.3 |
| 50 | 98.4 | 96.3 | 0.1 | 0.1 | 0.2 |
| 55 | 98.4 | 96.9 | 0.1 | 0.1 | 0.2 |
| 60 | 98.4 | 97.3 | 0.1 | 0.1 | 0.2 |
| 65 | 98.7 | 95.5 | 0.5 | 0.0 | 0.5 |
| 70 | 98.8 | 95.0 | 0.5 | 0.5 | 1.0 |
| 75 | 99.3 | 93.5 | 2.4 | 1.5 | 3.9 |
| 80 | 99.1 | 94.4 | 2.1 | 0.4 | 2.5 |
| 85 | 99.5 | 89.7 | 6.2 | 0.5 | 6.7 |
| 90 | 98.0 | 87.3 | 9.4 | 0.2 | 9.6 |

TABLE II

| Fraction No | Temperature (°C.) Vapor Measured By Thermometer 1322 | Temperature (°C.) Non-Condensed Measured By Thermometer 1329 | % Benzaldehyde | % Back Peaks Anisaldehyde | % Back Peaks Cinnamaldehyde | Total |
|---|---|---|---|---|---|---|
| 1 | 96.3 | 84.5 | 21.8 | 0.7 | 35.2 | 35.9 |
| 2 | 99.0 | 79.0 | 40.9 | 0.6 | 24.2 | 24.8 |
| 3 | 98.8 | 80.0 | 66.0 | 0.6 | 11.7 | 12.3 |
| 4 | 98.7 | 80.0 | 78.9 | 0.5 | 7.9 | 8.4 |
| 6 | 98.4 | 80.0 | 88.7 | 0.3 | 3.4 | 3.7 |
| 8 | 98.4 | 81.0 | 93.0 | 0.2 | 1.5 | 1.7 |
| 10 | 98.4 | 84.5 | 94.6 | 0.2 | 0.9 | 1.1 |
| 12 | 98.4 | 84.0 | 95.5 | 0.3 | 0.7 | 1.0 |
| 14 | 98.1 | 84.5 | 94.3 | 0.8 | 2.3 | 3.1 |
| 16 | 98.0 | 84.0 | 95.1 | 0.8 | 1.8 | 2.6 |
| 18 | 98.2 | 83.5 | 94.5 | 1.2 | 2.2 | 3.4 |
| 20 | 98.4 | 84.0 | 91.7 | 2.5 | 3.7 | 6.2 |
| 22 | 98.3 | 84.0 | 88.6 | 4.1 | 5.3 | 9.4 |
| 24 | 98.7 | 83.0 | 88.0 | 5.2 | 4.6 | 9.8 |
| 26 | 99.1 | 84.0 | 80.0 | 11.0 | 6.5 | 17.5 |
| 28 | 99.3 | 83.5 | 64.3 | 22.1 | 10.4 | 32.5 |
| 30 | 99.2 | 83.5 | 54.6 | 31.4 | 10.3 | 41.7 |
| 32 | 99.5 | 42.5 | 68.1 | 22.9 | 4.1 | 27.0 |

FIG. 14 sets forth the graph of temperature and composition changes during steam distillation of cassia oil (as set forth in Table I). The graph indicated by reference numeral 1401 is the graph of temperature versus fraction number. The graph indicated by reference numeral 1402 is the graph of the composition of matter containing o-anisaldehyde and cinnamaldehyde verus faction number. The graph indicated by reference numeral 1403 is a graph of percent benzaldehyde versus fraction number. Percent benzaldehyde is set forth on the Y axis at the right-hand side of the graph. The percent of the combination of cinnamaldehyde and anisaldehyde is set forth at the right-hand side of the graph. The temperature is set forth on the Y axis at the left-hand side of the graph.

Second steam distillation. 3854 Grams of crude benzaldehyde, 1000 grams of sodium carbonate, 10 liters of water and 20 grams of TWEEN 20 are admixed and placed in a 22 liter flask.

The nitrogen flow rate is minimal. The mixture is heated to reflux and maintained on total reflux for two hours. The reflux ratio is progressively changed as follows:

(i) 2:1 for period of one hour;
(ii) 1:1 for the next six hours;
(iii) 2:1 for the next five hours;
(iv) 4:1 for the next six hours; and
(v) 9:1 for the remaining time.

The distillation is continued until no more oil is present in the distillate. The total weight of recovered organics is 3286 grams (85% of charge).

The distillation fractions for this second steam distillation are as follows:

| Fraction No. | Vapor Temp. (°C.) | Time | Reflux Ratio |
|---|---|---|---|
| 1 | 95/ | 0730 | Total Reflux |
| 2 | 95 | 0850 | Total Reflux |
| 3 | 95 | 0940 | Total Reflux |
| 4 | 95 | 1030 | 2:1 |
| 5 | 97 | 1115 | 1:1 |
| 6 | 97 | 1145 | 1:1 |
| 7 | 97 | 1215 | 1:1 |
| 8 | 97 | 1245 | 1:1 |
| 9 | 97 | 1315 | 1:1 |
| 10 | 97 | 1345 | 1:1 |
| 11 | 97 | 1415 | 1:1 |
| 12 | 97 | 1500 | 1:1 |
| 13 | 98 | 1530 | 1:1 |
| 14 | 98 | 1600 | 1:1 |
| 15 | 98 | 1630 | 1:1 |
| 16 | 97 | 1700 | 1:1 |
| 17 | 98 | 1730 | 1:1 |
| 18 | 98 | 1800 | 2:1 |
| 19 | 98 | 1830 | 2:1 |
| 20 | 98 | 1900 | 40% Take-Off |
| 21 | 98 | 1930 | 40% Take-Off |
| 22 | 98 | 2000 | 40% Take-Off |
| 23 | 98 | 2030 | 2:1 |
| 24 | 98 | 2100 | 2:1 |
| 25 | 98 | 2130 | 2:1 |
| 26 | 98 | 2200 | 2:1 |
| 27 | 98 | 2230 | 2:1 |
| 27 | 98 | 2300 | 2:1 |
| 29 | 98 | 2330 | 2:1 |
| 30 | 98 | 0000 | 4:1 |
| 31 | 98 | 0100 | 4:1 |
| 32 | 98 | 0200 | 4:1 |
| 33 | 98 | 0300 | 4:1 |
| 34 | 98 | 0400 | 4:1 |
| 35 | 98 | 0600 | 9:1 |
| 36 | 98 | 0800 | 9:1 |
| 37 | 98 | 1000 | 9:1 |
| 38 | 98 | 1200 | 9:1 |
| 39 | 98 | 1400 | 9:1 |
| 40 | 98 | 1600 | 9:1 |
| 41 | 98 | 1800 | 9:1 |
| 42 | 98 | 2000 | 9:1 |
| 43 | 98 | 2200 | 9:1 |
| 44 | 98 | 0000 | 9:1 |
| 45 | 98 | 0200 | 9:1 |
| 46 | 98 | 0400 | 9:1 |
| 47 | 98 | 0600 | 9:1 |
| 48 | 98 | 0800 | 9:1 |
| 49 | 98 | 1000 | 9:1 |
| 50 | 98 | 1200 | 9:1 |
| 51 | 98 | 1400 | 9:1 |
| 52 | 98 | 1600 | 9:1 |
| 53 | 98 | 1800 | 9:1 |
| 54 | 98 | 2000 | 9:1 |
| 55 | 98 | 2200 | 9:1 |
| 56 | 98 | 0000 | 9:1 |
| 57 | 99 | 0200 | 9:1 |
| 58 | 99 | 0400 | 9:1 |
| 59 | 99 | 0600 | 9:1 |
| 60 | 99 | 0830 | 19:1 |
| 61 | 98 | 1040 | 19:1 |
| 62 | 98 | 1200 | 19:1 |

FIG. 15 is the GLC profile for the product subjected to the second distillation (Conditions: Fused silica/methyl silicone column).

FIG. 16 is the GLC profile for redistillation Fraction 14 of the foregoing distillation (Conditions: Fused silica/methyl silicone column).

FIG. 17 is the GLC profile for redistillation Fraction 54 of the foregoing redistillation (Conditions: Fused silica/methyl silicone column).

FIG. 18 is the GLC profile for redistillation Fraction 58 of the foregoing distillation (Conditions: Fused silica/methyl silicone column).

Example XXV

Preparation of Natural Benzaldehyde-Cinnamaldehyde Mixture and Natural Acetaldehyde Composition Reaction:

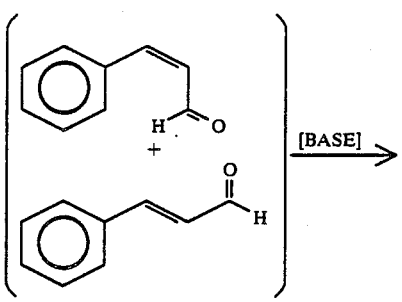

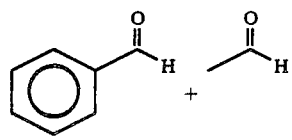

Using the same equipment as in Example XXIV (12 liter reaction flask equipped with electric stirrer, 4' Goodloe column, large distillation head, 2 cold traps and nitrogen purge), the following materials are added to the 12 liter reaction vessel:

| | |
|---|---|
| 1,150 grams | cassia oil (steam distilled) |
| 500 grams | water |
| 276 grams | sodium bicarbonate |
| 10 grams | TWEEN 80 having the structure: |

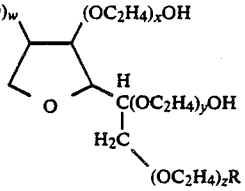

wherein $W+X+Y+Z=20$ and the R moiety represents 75% monooleate residue with the balance being linoleate residue, palmitate residue and stearate residue.

The water and sodium bicarbonate are first added to the reaction vessel with stirring. The cassia oil and SPAN 80 are then combined and added to the reaction vessel. The reaction mass, with stirring is heated to reflux maintaining a 19:1 reflux ratio. The reaction at a 19:1 reflux ratio is continued for a period of 72 hours, after which time the reaction mass is steam distilled yielding the following fractions:

| Fraction No. | Vapor Temp. (°C.) | Time | Reflux Ratio | Boil Up Rate at #/Hr. | Weight of Fraction |
|---|---|---|---|---|---|
| 1 | 98/ | 1635 | | 95.3 | 43 |
| 2 | 97½ | 1815 | 19:1 | 95.6 | 81 |
| 3 | 97½ | 1940 | 19:1 | 96.0 | 64 |
| 4 | 98 | 2100 | 19:1 | 95.8 | 64 |
| 5 | 98 | 2225 | 19:1 | 95.5 | 55 |
| 6 | 98 | 2305 | 19:1 | 96.0 | 50 |
| 7 | 96 | 1045 | 19:1 | 95.0 | 47 |
| 8 | 96 | 1145 | 19:1 | 96.0 | 36 |
| 9 | 96 | 1320 | 19:1 | 96.0 | 36 |
| 10 | 96 | 1415 | 19:1 | 96.0 | 21 |
| 11 | 96 | 1600 | 19:1 | 96.0 | 26 |
| 12 | 99 | 1815 | 19:1 | 88.0 | 27 |
| 13 | 99 | 2235 | 19:1 | 84.6 | 18 |
| 14 | 99 | 1235 | 19:1 | 92.0 | 21 |
| 15 | 99 | 1330 | 19:1 | 94.0 | 15 |
| 16 | 98 | 1900 | 19:1 | 93.3 | 30 |
| 17 | 98 | 2230 | 19:1 | 92.4 | 30 |

Fractions 1–17 are bulked and redistilled using a 2 liter distillation flask, 1' Goodloe column, large distillation head, fraction cutter and heating mantle. 657 Grams of bulked Fractions 1–17 from the first distillation are combined with 25 grams of pryenel. The material is vacuum distilled at 40 mm/Hg pressure using a reflux ratio of 9:1 yielding the following fractions:

| Fraction No. | Vapor Temp. (°C.) | Liquid Temp. (°C.) | Vacuum mm/Hg. Pressure | Reflux Ratio | Weight of Fraction |
|---|---|---|---|---|---|
| 1 | 75/ | 82/ | 40 | 9:1 | 24 |
| 2 | 73 | 81 | 40 | 9:1 | 24 |
| 3 | 75 | 82 | 40 | 9:1 | 21 |
| 4 | 75 | 82 | 40 | 9:1 | 22 |
| 5 | 75 | 82 | 40 | 9:1 | 19 |
| 6 | 75 | 82 | 40 | 9:1 | 19 |
| 7 | 75 | 82 | 40 | 9:1 | 20 |
| 8 | 75 | 83 | 40 | 9:1 | 21 |
| 9 | 75 | 84 | 40 | 9:1 | 20 |
| 10 | 75 | 83 | 40 | 9:1 | 31 |
| 11 | 75 | 83 | 40 | 9:1 | 30 |
| 12 | 74 | 84 | 40 | 9:1 | 25 |
| 13 | 74 | 85 | 40. | 9:1 | 25 |
| 14 | 73 | 85 | 40 | 9:1 | 28 |
| 15 | 75 | 90 | 40 | 9:1 | 30 |
| 16 | 74 | 92 | 40 | 9:1 | 26 |
| 17 | 74 | .97 | 40 | 9:1 | 26 |
| 18 | 74 | 105 | 40 | 9:1 | 20 |
| 19 | 73 | 115 | 40 | 9:1 | 20 |
| 20 | 73 | 127 | 40 | 9:1 | 16 |
| 21 | 73 | 133 | 40 | 9:1 | 11 |
| 22 | 79 | 140 | 40 | 9:1 | 15 |
| 23 | 92 | 142 | 40 | 9:1 | 11 |
| 24 | 96 | 143 | 40 | 9:1 | 4 |
| 25 | 122 | 220 | 30 | 9:1 | 28 |

FIG. 21 is the GLC profile for the crude first distillation product (Conditions: Fused silica/methyl silicone column).

FIG. 22 is the GLC profile for the second (vacuum) distillation Fraction 1 (Conditions: 50 meter×0.31 mm fused silica/methyl silicone column). The peak indicated by reference numeral 2201 is the peak for benzaldehyde. The peak indicated by reference numeral 2202 is the peak for acetaldehyde.

FIG. 23 is the GLC profile for the second (vacuum) distillation Fraction 9 of the foregoing distillation (Conditions: 50 m×0.31 mm OV 1 fused silica/methyl silicone OV-1 column programmed at 75°–225° C. at 2.0° C. per minute). The peak indicated by reference numeral 2301 is the peak for the benzaldehyde.

EXAMPLE XXVI

Analyses of First Steam Distillation Product of Example XXIV

GLC analyses for the crude distillation product prior to the second steam distillation for Example XXIV were carried out first using a 50 m×0.32 mm fused silica/methyl silicone column programmed at 75°–225° C. at 2.0° C. per minute and then using a 50 m×0.32 mm fused silica/carbowax 20M column programmed at 75°–225° C. at 2.0° C. per minute.

FIG. 24 is the GLC profile for this product using the fused silica/methyl silicone column.

FIG. 25 is the GLC profile for this product using the fused silica/carbowax 20M column.

With respect to FIG. 24, the peak indicated by reference numeral 2401 is the peak for acetaldehyde. The peak indicated by reference numeral 2402 is the peak for crotonaldehyde. The peak indicated by reference numeral 2403 is the peak for benzaldehyde. The peak indicated by reference numeral 2404 is the peak for salicylaldehyde, benzyl alcohol and para Cymene. The peak indicated by reference numeral 2405 is the peak for phenyl ethyl alcohol. The peak indicated by reference numeral 2406 is the peak for 2-methyl benzofuran and isoborneol. The peak indicated by reference numeral 2407 is the peak for cis cinnamaldehyde. The peak indicated by reference numeral 2408 is the peak for 2-methoxy benzaldehyde. The peak indicated by reference numeral 2409 is the peak for trans cinnamaldehyde.

With reference to FIG. 25, the peak indicated by reference numeral 2501 is the peak for acetaldehyde. The peak indicated by reference numeral 2502 is the peak for crotonaldehyde. The peak indicated by reference numeral 2503 is the peak for benzaldehyde. The peak indicated by reference numeral 2504 is the peak for beta caryophyllene. The peak indicated by reference numeral 2505 is the peak for salicyladehyde. The peak indicated by reference numeral 2506 is the peak for isoborneol. The peak indicated by reference numeral 2507 is the peak for 2-methyl benzofuran. The peak indicated by reference numeral 2508 is the peak for cis cinnamaldehyde. The peak indicated by reference numeral 2509 is the peak for phenyl ethyl alcohol. The peak indicated by reference numeral 2510 is the peak for 2-methoxy benzaldehyde. The peak indicated by reference numeral 2511 is the peak for trans cinnamaldehyde.

The acetaldehyde has the structure:

The crotonaldehyde has the structure:

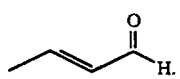

The benzaldehyde has the structure:

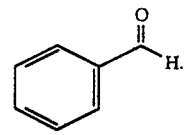

Beta caryophyllene has the structure:

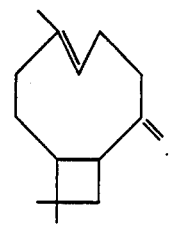

Salicylaldehyde has the structure:

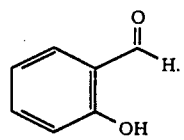

Isoborneol has the structure:

2-Methyl benzofuran has the structure:

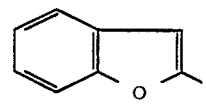

Cis cinnamaldehyde has the structure:

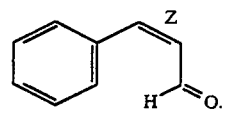

Phenyl ethyl alcohol has the structure:

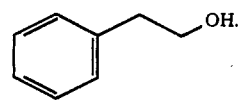

2-Methoxy benzaldehyde has the structure:

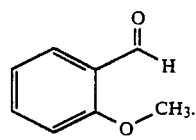

Trans cinnamaldehyde has the structure:

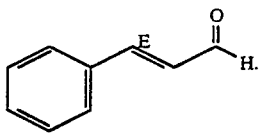

Benzyl alcohol has the structure:

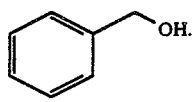

Para Cymene has the structure:

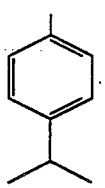

EXAMPLE XXVII

The following sweet cherry flavor formulation is prepared:

| Ingredients | Parts by Weight |
| --- | --- |
| Allyl isovalerate | 15.0 |
| Amyl butyrate | 200.0 |
| Anisic aldehyde | 37.0 |
| Anisyl acetate | 25.0 |
| Anisyl butyrate | 12.0 |
| Anisyl propionate | 12.0 |
| Benzyl acetate | 50.0 |
| Second vacuum distillation product of the reaction product of Example XXV (bulked Fractions 8-16) | 4,658.0 |
| Eugenol | 7.0 |
| Cyclohexyl cinnamate | 5.0 |
| Cyclohexyl formate | 8.0 |
| Ethyl acetate | 680.0 |
| Ethyl butyrate | 152.0 |
| Ethyl methylglycidate | 100.0 |
| Rhodinol | 60.0 |
| Beta-ionone | 4.0 |
| Jasmine absolute | 13.0 |
| Citral | 1.0 |
| Maltol (5% in ethanol) | 1.0 |
| Orris butter | 30.0 |
| Orris resinoid | 160.0 |
| Rhodinyl formate | 1.0 |
| Rhodinyl isovalerate | 12.0 |
| Para-Toluic aldehyde | 500.0 |
| Vanillin | 400.0 |
| Propylene glycol | 2,920.0 |
| Total: | 10,000.0 |

The resulting flavor is compared with the same flavor produced using a mixture of bitter almond essential oil and extracted Ceylon, cinnamon, cinnamaldehyde in a combined amount of 4658.0 parts by weight (grams). The cherry flavor containing the second distillation product of the reaction product of Example XXV is unanimously preferred by a bench panel of five members independent of the inventive entity of the instant patent application due to the more natural nature of the overall flavor. The natural cherry nuances imparted using the second distillation product of the reaction product of Example XXV give rise to unexpected, unobvious and advantageous properties of the resulting cherry flavor formulation.

EXAMPLE XXVIII

A. Powder Flavor Formulation

Twenty grams of the flavor composition of Example XXVII is emulsified in a solution containing 300 grams gum acacia and 700 grams of water. The emulsion is spray dried with a Bowen Lab Model Drier utilizing 260 c.f.m. of air with an inlet temperature of 500° F. and an outlet temperature of 200° F. and a wheel speed of 50,000 rpm.

B. Sustained Release Flavor

The following mixture is prepared:

| Ingredients | Parts by Weight |
| --- | --- |
| Liquid cherry flavor composition of Example VII | 20 |
| Propylene glycol | 9 |
| Cab-O-Sil ® M-5 (brand of silica produced by the Cabot Corp. of 125 High Street, Boston, Mass. 02110) | 5 |
| Physical properties: | |
| Surface area: | 200 m²/gm |
| Nominal particle size: | 0.012 microns |
| Density: | 2.3 lbs/cu. ft. |

The Cab-O-Sil ® is dispersed in the liquid cherry flavor composition of Example XXVII with vigorous stirring thereby resulting in a viscous liquid. Seventy-one parts by weight of the powder flavor composition of Part A, supra, is then blended into said viscous liquid with stirring at 25° C. for a period of 30 minutes resulting in a dry, free-flowing sustained release flavor powder.

EXAMPLE XXIX

Ten parts by weight of 50 Bloom pigskin gelatin is added to ninety parts by weight of water at a temperature of 150° F. The mixture is agitated until the gelatin is completely dissolved and the solution is cooled to 120° F. Twenty parts by weight of the liquid flavor composition of Example XXVII is added to the solution which is then homogenized to form an emulsion having a particle size typically in the range of 5-40 microns. The material is kept at 120° F. under which conditions the gelatin will not gel.

Coacervation is induced by adding slowly and uniformly, forty parts by weight of a 20% aqueous solution of sodium sulphate. During coacervation of gelatin, molecules are deposited uniformly about each oil droplet as a nucleus.

Gelation is effected by pouring the heated coacervate mixture into 1,000 parts by weight of a 7% aqueous solution of sodium sulphate at 65° F. The resulting gelled coacervate may be filtered and washed with water at temperatures below the melting point of gelation, to remove the salt.

Hardening of the filter cake, in this example, is effected by washing with 200 parts by weight of 37% solution of formaldehyde in water. The cake is then washed to remove the residual formaldehyde.

EXAMPLE XXX

Chewing Gum

One hundred parts by weight of chicle are mixed with four parts by weight of the flavor prepared in accordance with Example XXVIII, Part B. Three hundred parts of sucrose and one hundred parts of corn syrup are added. Mixing is effected in a ribbon blender with jacketed side walls of the type manufactured by the Baker Perkins Co.

The resultant chewing gum blend is then manufactured into strips one inch in width and 0.1 inches in thickness. The strips are cut into lengths of three inches each. On chewing, the chewing gum has a pleasant, long-lasting natural cherry flavor.

EXAMPLE XXXI

One hundred parts by weight of chicle are mixed with eighteen parts by weight of the flavor prepared in accordance with Example XXIX. Three hundred parts of sucrose and one hundred parts of corn syrup are then added. Mixing is effected in a ribbon blender with jacketed side walls of the type manufactured by the Baker Perkins Co.

The resultant chewing gum blend is then manufactured into strips one inch in width and 0.1 inches in thickness. The strips are cut into lengths of 3" each. On chewing, the chewing gum has a pleasant, long-lasting natural cherry flavor.

EXAMPLE XXXII

Toothpaste Formulation

The following separate groups of ingredients are prepared:

| Parts by Weight | Ingredients |
|---|---|
| Group "A" | |
| 30.200 | Glycerine |
| 15.325 | Distilled water |
| 0.100 | Sodium benzoate |
| 0.125 | Saccharin sodium |
| 0.400 | Stannous fluoride |
| Group "B" | |
| 12.500 | Calcium carbonate |
| 37.200 | Dicalcium phosphate (dihydrate) |
| Group "C" | |
| 2.000 | Sodium n-lauroyl sarcosinate (foaming agent) |
| Group "D" | |
| 1.200 | Flavor material of Example XXVIII, Part B |
| 100.000 | (Total) |

Procedure:
1. The ingredients in Group "A" are stirred and heated in a steam jacketed kettle to 160° F.
2. Stirring is continued for an additional three to five minutes to form a homogeneous gel.
3. The powders of Group "B" are added to the gel, while mixing until a homogeneous paste is formed.
4. With stirring, the flavor of "D" is added and lastly, the sodium n-lauroyl sarcosinate.
5. The resultant slurry is then blended for one hour. The completed paste is then transferred to a three roller mill and then homogenized, and finally tubed.

The resulting toothpaste, when used in a normal toothbrushing procedure, yields a pleasant, sweet, cherry flavor of constant strong intensity throughout said procedure (1–1.5 minutes).

EXAMPLE XXXIII

Chewable Vitamin Tablets

The flavor material produced according to the process of Example XXVIII, Part B, is added to a chewable vitamin tablet formulation at a rate of 10 gm/kg which chewable vitamin tablet formulation is prepared as follows:

In a Hobart Mixer, the following materials are blended to homogeneity:

| Ingredients | Gms/1000 Tablets |
|---|---|
| Vitamin C (ascorbic acid as ascorbic acid-sodium ascorbate mixture 1:1) | 70.000 |
| Vitamin $B_1$ (thiamine mononitrate) as Rocoat ® thiamine mononitrate 33⅓% (Hoffman LaRoche) | 4.000 |
| Vitamin $B_2$ (riboflavin) as Rocoat ® riboflavin 33⅓% | 5.000 |
| Vitamin $B_6$ (pyridoxine hydrochloride) as Rocoat ® pyridoxine hydrochloride 33⅓% | 4.000 |
| Niacinamdie as Rocoat ® niacinamide 33⅓% | 33.000 |
| Calcium pantothenate | 11.000 |
| Vitamin $B_{12}$ (cyanocobalamin) as Merck 0.1% in gelatin | 3.500 |
| Vitamin E (dl-alpha topcopheryl acetate) as dry Vitamin E acetate 33⅓% Roache | 6.600 |
| d-Biotin | 0.044 |
| Certified lake color | 5.000 |
| Flavor of Example XXVIII, Part B | as indicated above |
| Sweetener sodium saccharin | 1.000 |
| Magnesium stearate lubricant | 10.000 |
| Mannitol q.s. to make | 500.000 |

Preliminary tablets are prepared by slugging with flatfaced punches and grinding the slugs to 14 mesh. 13.5 Grams dry Vitamin A acetate and 0.6 grams Vitamin D are then added as beadlets. The entire blend is then compressed using concave punches at 0.5 grams each.

Chewing of the resultant tablets yields a pleasant, long-lasting, consistently strong, cherry flavor for a period of 12 minutes.

EXAMPLE XXXIV

Chewing Tobacco

Onto 100 pounds of tobacco for chewing (85% Wisconsin lead and 15% Pennsylvania lead) the following casing is sprayed at a rate of 30%:

| Ingredients | Parts by Weight |
|---|---|
| Corn syrup | 60.0 |
| Licorice | 10.0 |
| Glycerine | 20.0 |
| Fig juice | 4.6 |
| Prune juice | 5.0 |
| Flavor material of | 0.4 |

-continued

| Ingredients | Parts by Weight |
|---|---|
| Example XXVIII of Part B | |

The resultant product is redried to a moisture content of 20%. On chewing, this tobacco has an excellent substantially consistent, long-lasting, sweet, cherry nuance (20 minutes) in conjunction with the main fruity tobacco note.

EXAMPLE XXXV

Flavored Foodstuff 2.25 Ounces of a coconut macaroon mix distributed by Drake Bakeries, Division of Borden, Inc. of Columbus, Ohio 43215 is intimately admixed at the level of 20 ppm with the benzaldehyde/cinnamaldehyde mixture (second distillation product) prepared according to Example XXV.

The coconut macaroon composition contains corn syrup, coconut, sugar and egg whites.

The coconut macaroon composition is then baked at 325° F. at atmospheric pressure for a period of 20 minutes. The resultant coconut macaroon cookies have an excellent "natural coconut" notes with intense almond nuances not present in the cookies without the composition of Example XXV.

When the composition of Example XXV is replaced with the compositions of Examples XXIV, second steam distillation product, a similar "natural coconut" almond nuance is created.

EXAMPLE XXXVI

Tobacco Flavor Formulation and Tobacco

A tobacco mixture is produced by admixing the following materials:

| Ingredients | Parts by Weight |
|---|---|
| Bright | 40.1 |
| Burley | 24.9 |
| Maryland | 1.1 |
| Turkish | 11.6 |
| Stem (flue-cured) | 14.2 |
| Glycerine | 2.8 |
| Water | 5.3 |

Cigarettes having cellulose acetate filters are prepared from this tobacco:
The following flavor formulation is prepared:

| Ingredients | Parts by Weight |
|---|---|
| Ethyl butyrate | .05 |
| Ethyl valerate | .05 |
| Maltol | 2.00 |
| Cocoa extract | 26.00 |
| Coffee extract | 10.00 |
| Ethyl alcohol (95% aqueous) | 20.00 |
| Water | 41.90 |

The above-stated tobacco flavor formulation is applied at the rate of 0.1% to all of the cigarettes produced using the above tobacco formulation. One-third of the cigarettes are then treated in the tobacco section thereof with 5 ppm of the benzaldehyde/cinnamaldehyde mixture produced by the second distillation of Example XXV. One-third of the cigarettes are treated on the cellulose acetate filter with 1 microliter of a 0.1% ethanol solution of the cinnamaldehyde/benzaldehyde mixture produced by the second distillation of Example XXIV.

The control cigarettes not containing the mixture of benzaldehyde and cinnamaldehyde produced according to the process of Example XXIV or XXV and the experimental cigarettes which do contain the mixture of benzaldehyde and cinnamaldehyde produced according to the process of Example XXV and XXIV are evaluated by three-way comparison, and the results are as follows:

In aroma, the cigarettes containing the benzaldehyde and cinnamaldehyde of Example XXV and XXIV in the tobacco or in the filter have been found to be sweeter and fruitier with faint aesthetically pleasing cherry nuances.

In smoke flavor, the cigarettes containing the benzaldehyde and cinnamaldehyde mixture are more aromatic, more sweet, fruitier and slightly less harsh in the mouth and throat. In addition, those cigarettes containing the benzaldehyde and cinnamaldehyde mixture of Example XXV and XXIV in the tobacco give rise to a fruity nuance in the taste and aroma on smoking.

EXAMPLE XXXVII

Apple Flavor Formulation

The following basic apple flavor formulation is prepared:

| Ingredients | Parts by Weight |
|---|---|
| Amyl acetate | 1.0 |
| Gamma decalactone | 1.5 |
| Caproic acid | 1.5 |
| n-Hexyl acetate | 2.5 |
| Coriander Oil | 0.5 |
| n-Hexyl iso-butyrate | 2.5 |
| n-Hexanal | 5.0 |
| Ethyl isovalerate | 5.0 |
| cis-3-Hexenol | 18.0 |
| Ethyl-2-methyl butyrate | 18.0 |
| trans-2-Hexenal | 18.0 |
| Apple Fusel Oil | 26.0 |
| Maltol | 0.5 |
| 95% Food grade ethanol | 100.0 |

This basic apple flavor is compared, in water, with and without the addition of natural acetaldehyde prepared according to Example XXV at the rate of 6 ppm and at the rate of 10 ppm in water. The flavor with the addition of the natural acetaldehyde composition has a fresh apple juice character with light fruity topnotes. Both notes are missing in the flavor that does not contain the natural acetaldehyde composition of Example XXV. For this reason, the flavor with the natural acetaldehyde composition of Example XXV is preferred unanimously by a three-member bench panel.

EXAMPLE XXXVIII

Preparation of Natural Benzaldehyde-Cinnamaldehyde Mixture and Natural Acetaldehyde Composition Reaction:

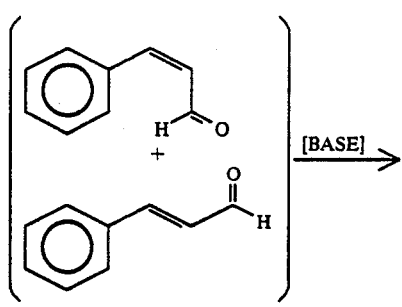

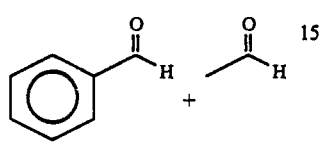

Using the same equipment as in Example XXIV (12 liter reaction flask equipped with electric stirrer, 4' Goodloe column, large distillation head, 2 cold traps and nitrogen purge), the following materials are added to the 12 liter reaction vessel:

| | |
|---|---|
| 1,160 grams | cassia oil (steam distilled)(contains 75.2% cinnamaldehyde) |
| 2,760 grams | water |
| 276 grams | sodium bicarbonate |
| 5 grams | T-MAZ 65K ® (registered trademark of Mazer Chemicals, Inc. of Gurnee, Illinois) having the structure: $R_4O(C_2H_4O)_w$ ... $(OC_2H_4)_xOR_3$ ... $C(OC_2H_4)_yOR_2$ ... $(OC_2H_4)_zR_1$ | wherein $W+X+Y+Z=20$ and
three of $R_1$, $R_2$, $R_3$ and $R_4$ represents stearate and one of $R_1$, $R_2$, $R_3$ and $R_4$ represents hydrogen).

The water and sodium bicarbonate are first added to the reaction vessel with stirring. The cassia oil and T-MAZ 65K ® are then combined and added to the reaction vessel. The reaction mass, with stirring is heated to reflux maintaining a 19:1 reflux ratio. The reaction at a 19:1 reflux ratio is continued for a period of 72 hours, after which time the reaction mass is steam distilled yielding the following fractions:

| Fraction No. | Vapor Temp. (°C.) | Liquid Temp. (°C.) | Time | Reflux Ratio |
|---|---|---|---|---|
| 1 | 97/97 | —/— | 1515 | 19:1 |
| 2 | 97 | | 1815 | 19:1 |
| 3 | 97 | | 2150 | 19:1 |
| 4 | 97 | | 2300 | 19:1 |
| 5 | 96 | | 1200 | 19:1 |
| 6 | 97 | | 1513 | 19:1 |
| 7 | 97 | | 1730 | 19:1 |
| 8 | 97 | | 1940 | 19:1 |
| 9 | 98 | | 2330 | 19:1 |
| 10 | 98 | | 1110 | 19:1 |
| 11 | 96 | | 1730 | 19:1 |
| 12 | 96 | | 1940 | 19:1 |
| 13 | 96 | | 2140 | 19:1 |

-continued

| Fraction No. | Vapor Temp. (°C.) | Liquid Temp. (°C.) | Time | Reflux Ratio |
|---|---|---|---|---|
| 14 | 96 | | 2305 | 19:1 |

FIG. 26 is the GLC profile for the crude reaction product (Conditions: 50 m×0.32 mm fused silica/methyl silicone column programmed at 75°–225° C. at 2.0° C. per minute).

EXAMPLE XXXIX

Preparation of Natural Benzaldehyde/Cinnamaldehyde Mixture and Natural Acetaldehyde Composition Reaction:

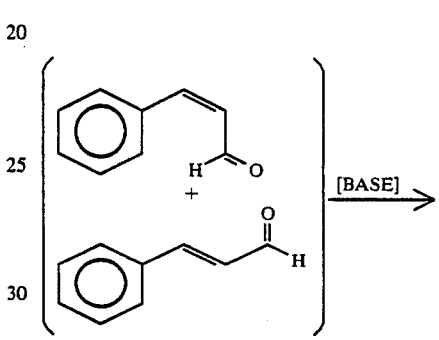

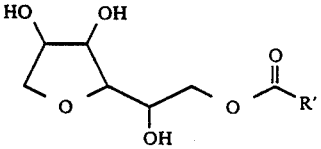

Using the same equipment as in Example XXIV (12 liter reaction flask equipped with electric stirrer, 1' Goodloe column, large distillation head, 2 cold traps and nitrogen purge), the following materials are added to the 12 liter reaction vessel:

| | |
|---|---|
| 1,150 grams | Cassia oil (containing 75.2% cinnamaldehyde) |
| 2,760 grams | Water |
| 276 grams | sodium bicarbonate |
| 10 grams | SPAN 80 which is a mixture of compounds defined according to the structures: |

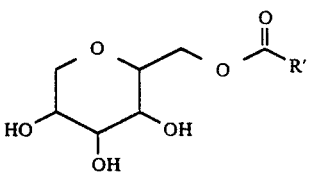

and

-continued

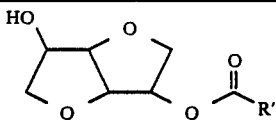

wherein R' moiety is the monooleate residue.

The water and sodium bicarbonate are first added to the reaction vessel with stirring. The cassia oil and SPAN 80 are then combined and added to the reaction vessel. The reaction mass with stirring is heated to reflux maintaining a 19:1 reflux ratio. The reaction at a 19:1 reflux ratio is continued for a period of 48 hours after which time the reaction mass is steam distilled yielding the following fractions:

| Fraction No. | Vapor Temp. (°C.) | Time | Reflux Ratio |
|---|---|---|---|
| 1 | 97 | 1845 | 19:1 |
| 2 | 97 | 2100 | 19:1 |
| 3 | 97 | 2300 | 19:1 |
| 4 | 97 |  | 19:1 |
| 5 | 97 | .1545 | 19:1 |
| 6 | 97 | 1825 | 19:1 |
| 7 | 97 | 2100 | 19:1 |
| 8 | 97 | 1145 | 19:1 |
| 9 | 97 | 1445 | 19:1 |
| 10 | 97 | 2030 | 19:1 |
| 11 | 97 | 2300 | 19:1 |

FIG. 27 is the GLC profile for the crude reaction product (Conditions: 50 m×0.32 mm fused silica/methyl silicone column programmed at 75°-225° C. at 2.0° C. per minute). The peak indicated by reference numeral 2701 is the peak for benzaldehyde.

EXAMPLE XL

Preparation of Natural Benzaldehyde-Cinnamaldehyde Mixture and Natural Acetaldehyde Composition Reaction:

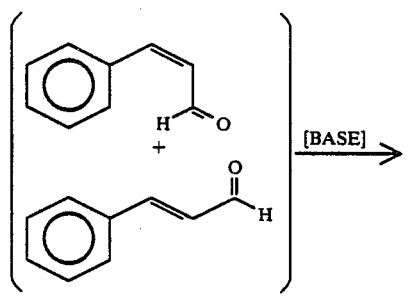

Using the same equipment as in Example XXIV (12 liter reaction flask equipped with electric stirrer, 2' Goodloe column, large distillation head, 2 cold traps and nitrogen purge), the following materials are added to the 12 liter reaction vessel:

| 1,150 grams | cassia oil |
| 276 grams | sodium bicarbonate |
| 5,000 grams | water |
| 5 grams | T-MAZ 60-K ® (registered trademark of the Mazer Chemicals, Inc. of Gurnee, Illinois) having the structure: |

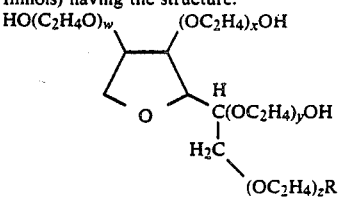

wherein W+X+Y+Z=20 and
the R moiety represents monooleate.

The water and sodium bicarbonate are first added to the reaction vessel with stirring. The cassia oil and T-MAZ 80 ® are then combined and added to the reaction vessel. The reaction mass with stirring is heated to reflux maintaining a 19:1 reflux ratio. The reaction at a 19:1 reflux ratio is continued for a period of 72 hours after which time the reaction mass is steam distilled yielding the following fractions:

| Fraction No. | Vapor Temp. (°C.) | Time | Reflux Ratio |
|---|---|---|---|
| 1 | /95 | — | 19:1 |
| 2 |  | 1600 | 19:1 |
| 3 | 95 | 1750 | 19:1 |
| 4 | 95 | 1940 | 19:1 |
| 5 | 95 | 2155 | 19:1 |
| 6 | 95 | 2300 | 19:1 |
| 7 | 95 | 1200 | 19:1 |
| 8 |  | 1449 | 19:1 |
| 9 | 96 | 1722 | 19:1 |
| 10 | 96 | 1950 | 19:1 |
| 11 | 96 | 2300 | 19:1 |
| 12 | 96 | 1400 | 19:1 |
| 13 | 98 | 1915 | 19:1 |
| 14 | 98 | 2300 | 19:1 |
| 15 | 96 | 1030 | 19:1 |
| 16 | 96 | 1130 | 19:1 |
| 17 | 96 | 1245 | 19:1. |

FIG. 28 is the GLC profile for bulked fractions 1-17 of the foregoing distillation (Conditions: 50 m×0.32 mm fused silica/methyl silicone column programmed at 75°-225° C. at 2° C. per minute).

EXAMPLE XLI

Tobacco Flavor Formulation and Tobacco

A tobacco mixture is produced by admixing the following materials:

| Ingredients | Parts by Weight |
|---|---|
| Bright | 40.1 |
| Burley | 24.9 |
| Maryland | 1.1 |
| Turkish | 11.6 |
| Stem (flue-cured) | 14.2 |
| Glycerine | 2.8 |
| Water | 5.3 |

Cigarettes having cellulose acetate filters are prepared from this tobacco:

The following flavor formulation is prepared:

| Ingredients | Parts by Weight |
| --- | --- |
| Ethyl butyrate | .05 |
| Ethyl valerate | .05 |
| Maltol | 2.00 |
| Cocoa extract | 26.00 |
| Coffee extract | 10.00 |
| Ethyl alcohol (95% aqueous) | 20.00 |
| Water | 41.90 |

The above-stated tobacco flavor formulation is applied at the rate of 0.1% to all of the cigarettes produced using the above tobacco formulation. One-third of the cigarettes are then treated in the tobacco section thereof with 5 ppm of the benzaldehyde/cinnamaldehyde mixture produced by the distillation of Example XXXVIII. One-third of the cigarettes are treated on the cellulose acetate filter with 1 microliter of a 0.1% ethanol solution of the cinnamaldehyde/benzaldehyde mixture produced according to the distillation of Example XXXIX. One-third of the cigarettes remain untreated.

The control cigarettes not containing the mixture of benzaldehyde and cinnamaldehyde produced according to the process of Example XXXVIII or XXXIX and the experimental cigarettes which do contain the mixture of benzaldehyde and cinnamaldehyde produced according to the process of Example XXXVIII or XXXIX are evaluated by three-way comparison, and the results are as follows:

- In aroma, the cigarettes containing the benzaldehyde and cinnamaldehyde of Example XXXVIII and XXXIX in the tobacco or in the filter have been found to be sweeter and fruiter with faint aesthetically pleasing cherry nuances.
- In smoke flavor, the cigarettes containing the benzaldehyde and cinnamaldehyde mixture are more aromatic, sweet, fruitier and slightly less harsh in the mouth and throat. In addition, those cigarettes containing the benzaldehyde and cinnamaldehyde mixture of Example XXXVIII and XXXIX in the tobacco give rise to a fruity nuance in the taste and aroma on smoking.

EXAMPLE XLII

Apple Flavor Formuluation

The following basic apple flavor formulation is prepared:

| Ingredients | Parts by Weight |
| --- | --- |
| Amyl acetate | 1.0 |
| Gamma decalactone | 1.5 |
| Caproic acid | 1.5 |
| n-Hexyl acetate | 2.5 |
| Coriander Oil | 0.5 |
| n-Hexyl iso-butyrate | 2.5 |
| n-Hexanal | 5.0 |
| Ethyl isovalerate | 5.0 |
| cis-3-Hexenol | 18.0 |
| Ethyl-2-methyl butyrate | 18.0 |
| trans-2-Hexenal | 18.0 |
| Apple Fusel Oil | 26.0 |
| Maltol | 0.5 |
| 95% Food grade ethanol | 100.0 |

This basic apple flavor is compared in water, with and without the addition of natural acetaldehyde prepared according to Example XL at the rate of 6 ppm and at the rate of 10 ppm in water. The flavor with the addition of the natural acetaldehyde composition has a fresh apple juice character with light fruity topnotes. Both notes are missing in the flavor that does not contain the natural acetaldehyde composition of Example XL. For this reason, the flavor with the natural acetaldehyde composition of Example XL is preferred unanimously by a three-member bench panel.

What is claimed is:

1. A composition of matter containing a substantial quantity of natural benzaldehyde and/or acetaldehyde produced according to the process comprising the step of carrying out a retro-aldol reaction on naturally occurring cinnamaldehyde in the presence of base, a natural or food grade nonionic emulsifier and an inert solvent selected from the group consisting or water and mixtures of water and $C_1$–$C_5$ alkanols and in the absence of any other reagents according to the reaction:

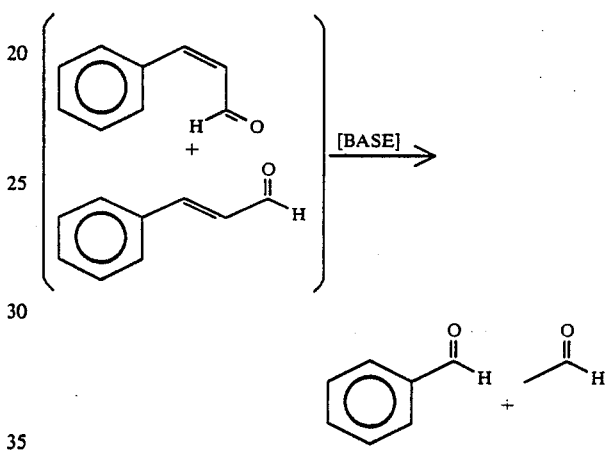

and simultaneously or subsequently steam distilling the reaction product from the reaction mass, the reaction being carried out in the presence of a nonionic sorbitan derivative emulsifier selected from the group consisting of compositions defined according to the structures:

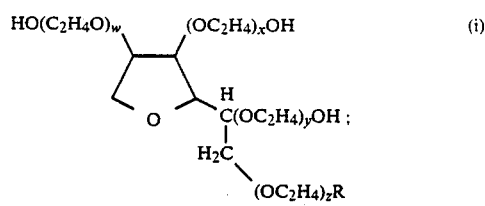

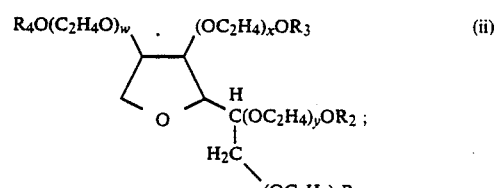

(iii) mixtures of materials having the structures:

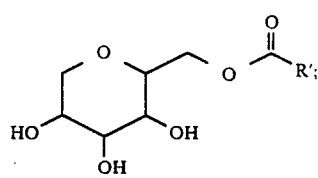

-continued
and

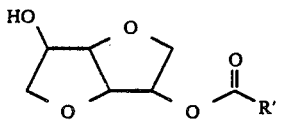

and (iv) mixtures of materials having the structures:

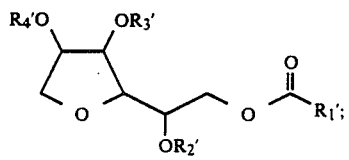

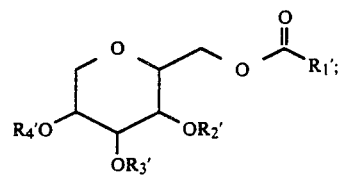

and

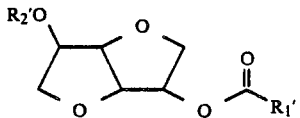

wherein R represents a fatty acid moiety selected from the group consisting of laurate, palmitate, stearate, oleate and tallate;

wherein R' represents a fatty acid moiety selected from the group consisting of laurate, palmitate, stearate, oleate and tallate;

wherein one, two, three or four of $R_1$, $R_2$, $R_3$ and $R_4$ represents the same or different laurate, palmitate, stearate, oleate or tallate and the other of $R_1$, $R_2$, $R_3$ and $R_4$ represents hydrogen; and wherein one, two, three or four of $R_1'$, $R_2'$, $R_3'$ and $R_4'$ represents the same or different laurate, palmitate, stearate, oleate or tallate; and wherein $W+X+Y+Z$ is in the range of from 4 up to 80, and wherein the reaction is carried out at from about 0.2 up to about 10 atmospheres; at a temperature of from about 40° C. up to about 150° C. and for a period of time of from about 5 hours up to about 80 hours.

2. The product of claim 1 wherein in the process for producing said product the base is selected from the group consisting of sodium carbonate, sodium bicarbonate, potassium carbonate, potassium bicarbonate, lithium carbonate, lithium bicarbonate, proline, choline, magnesium hydroxide, calcium hydroxide, magnesium carbonate, calcium carbonate and mixtures of lecithin and base.

3. The product of claim 1 wherein in the process for producting said product the naturally occurring cinnamaldehyde is in the form of a substance selected from the group consisting of:
  (i) cinnamon bark;
  (ii) cinnamon bark oil;
  (iii) cinnamon leaf; and
  (iv) cinnamon leaf oil.

4. The product of claim 1 wherein in the process for producing said product the concentration in the reaction mass of nonionic emulsifier is between about 1% up to about 6% by weight of the reaction mass and the percentage of water in the reaction mass is from about 50% up to about 90% by weight.

* * * * *